US008846401B2

(12) United States Patent  (10) Patent No.: US 8,846,401 B2
Harats et al.  (45) Date of Patent: *Sep. 30, 2014

(54) PROMOTERS EXHIBITING ENDOTHELIAL CELL SPECIFICITY AND METHODS OF USING SAME

(75) Inventors: Dror Harats, Ramat-Gan (IL); Eyal Breitbart, Hashmonaim (IL); Nira Bloom, Hod-HaSharon (IL)

(73) Assignee: Vascular Biogenics Ltd., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/454,171

(22) Filed: Apr. 24, 2012

(65) Prior Publication Data

US 2012/0201790 A1  Aug. 9, 2012

Related U.S. Application Data

(60) Division of application No. 13/094,900, filed on Apr. 27, 2011, now abandoned, which is a division of application No. 12/457,200, filed on Jun. 3, 2009, which is a division of application No. 10/975,619, filed on Oct. 29, 2004, now Pat. No. 7,579,327, which is a division of application No. 10/135,447, filed on May 1, 2002, now Pat. No. 7,067,649, which is a continuation-in-part of application No. PCT/IL01/01059, filed on Nov. 15, 2001.

(60) Provisional application No. 60/248,582, filed on Nov. 17, 2000.

(51) Int. Cl.
C12N 15/85 (2006.01)
C07H 21/04 (2006.01)

(52) U.S. Cl.
USPC .......................................... 435/455; 536/24.1

(58) Field of Classification Search
None
See application file for complete search history.

(56) References Cited

U.S. PATENT DOCUMENTS

| | | |
|---|---|---|
| 4,866,042 A | 9/1989 | Neuwelt |
| 5,464,764 A | 11/1995 | Capecchi et al. |
| 5,635,385 A | 6/1997 | Leopold et al. |
| 5,686,281 A | 11/1997 | Roberts |
| 5,734,039 A | 3/1998 | Calabretta et al. |
| 5,747,340 A | 5/1998 | Harats et al. |
| 5,792,453 A | 8/1998 | Hammond et al. |
| 5,830,880 A | 11/1998 | Sedlacek et al. |
| 5,882,893 A | 3/1999 | Goodearl |
| 5,906,827 A | 5/1999 | Khouri et al. |
| 5,916,763 A | 6/1999 | Williams et al. |
| 6,027,743 A | 2/2000 | Khouri et al. |
| 6,066,624 A | 5/2000 | Woo et al. |
| 6,110,480 A | 8/2000 | Chu et al. |
| 6,180,355 B1 | 1/2001 | Alexander et al. |
| 6,183,737 B1 | 2/2001 | Zaleske et al. |
| 6,200,751 B1 | 3/2001 | Gu et al. |
| 6,204,055 B1 | 3/2001 | Dean et al. |
| 6,206,917 B1 | 3/2001 | Williams et al. |
| 6,239,151 B1 | 5/2001 | Broadhurst et al. |
| 6,265,216 B1 | 7/2001 | Bennett et al. |
| 6,300,127 B1 | 10/2001 | Hair et al. |
| 6,300,490 B1 | 10/2001 | Huber et al. |
| 6,348,209 B2 | 2/2002 | Placke et al. |
| 6,376,244 B1 | 4/2002 | Atala |
| 6,438,802 B1 | 8/2002 | Beeman et al. |
| 6,444,803 B1 | 9/2002 | Hair et al. |
| 6,479,064 B1 | 11/2002 | Atala |
| 6,497,725 B2 | 12/2002 | Williams et al. |
| 6,503,886 B1 | 1/2003 | Baird et al. |
| 6,521,750 B2 | 2/2003 | Hair et al. |
| 6,545,048 B1 | 4/2003 | Patterson et al. |
| 6,576,265 B1 | 6/2003 | Spievack |
| 6,579,697 B1 | 6/2003 | Wallach et al. |
| 6,627,189 B1 | 9/2003 | Roth et al. |
| 6,652,583 B2 | 11/2003 | Hopkins et al. |
| 6,783,776 B2 | 8/2004 | Spievack |
| 6,866,864 B2 | 3/2005 | Mousa |
| 7,067,649 B2 | 6/2006 | Harats |
| 7,579,327 B2 | 8/2009 | Harats et al. |
| 7,585,666 B2 | 9/2009 | Harats et al. |
| 7,625,558 B2 | 12/2009 | Greene et al. |
| 7,989,427 B2 | 8/2011 | Harats et al. |
| 8,039,261 B2 | 10/2011 | Harats et al. |
| 8,071,740 B2 | 12/2011 | Harats et al. |
| 8,206,743 B2 | 6/2012 | Harats et al. |
| 8,415,318 B2 | 4/2013 | Harats et al. |
| 2003/0124100 A1 | 7/2003 | Harats |
| 2003/0194802 A1 | 10/2003 | Itskovitz-Eldor et al. |

(Continued)

FOREIGN PATENT DOCUMENTS

| | | |
|---|---|---|
| DE | 19838837 | 3/2000 |
| EP | 1302539 | 4/2003 |
| EP | 2174668 | 4/2010 |
| JP | 09-504784 | 5/1997 |
| JP | 2002/516568 | 6/2002 |
| JP | 2003-501367 | 1/2003 |
| JP | 2004-502409 | 1/2004 |
| WO | WO 95/05835 | 3/1995 |
| WO | WO 98/00013 | 1/1998 |
| WO | WO 98/37901 | 9/1998 |

(Continued)

OTHER PUBLICATIONS

Communication Pursuant to Article 94(3) EPC Dated Sep. 2, 2011 From the European Patent Office Re. Application No. 09174998.6.

(Continued)

Primary Examiner — Celine Qian
(74) Attorney, Agent, or Firm — Sterne, Kessler, Goldstein & Fox P.L.L.C.

(57) ABSTRACT

An isolated polynucleotide functional as a promoter in eukaryotic cells is disclosed. The isolated polynucleotide includes an endothelial specific enhancer element as detailed herein. Further disclosed is a method of expressing a nucleic acid sequence of interest in endothelial cells.

34 Claims, 38 Drawing Sheets
(24 of 38 Drawing Sheet(s) Filed in Color)

(56) References Cited

U.S. PATENT DOCUMENTS

| | | | |
|---|---|---|---|
| 2003/0195338 | A1 | 10/2003 | Chung et al. |
| 2004/0044403 | A1 | 3/2004 | Bischoff et al. |
| 2004/0048280 | A1 | 3/2004 | Harats |
| 2004/0170975 | A1 | 9/2004 | Savitzky et al. |
| 2004/0197860 | A1 | 10/2004 | Harats et al. |
| 2004/0224389 | A1 | 11/2004 | Bellgrau et al. |
| 2005/0112110 | A1 | 5/2005 | Harats |
| 2005/0186179 | A1 | 8/2005 | Harats et al. |
| 2006/0057113 | A1 | 3/2006 | Holm |
| 2006/0204478 | A1 | 9/2006 | Harats et al. |
| 2007/0286845 | A1 | 12/2007 | Harats et al. |
| 2008/0063656 | A1 | 3/2008 | Emini et al. |
| 2008/0305088 | A1 | 12/2008 | Harats et al. |
| 2009/0232808 | A1 | 9/2009 | Priest et al. |
| 2009/0326052 | A1 | 12/2009 | Harats et al. |
| 2010/0081193 | A1 | 4/2010 | Breitbart et al. |
| 2010/0282634 | A1 | 11/2010 | Harats et al. |
| 2010/0298226 | A1 | 11/2010 | Breitbart et al. |
| 2011/0129511 | A1 | 6/2011 | Harats et al. |
| 2011/0201677 | A1 | 8/2011 | Harats et al. |
| 2011/0207985 | A1 | 8/2011 | Harats et al. |
| 2011/0251122 | A1 | 10/2011 | Harats et al. |
| 2011/0319479 | A1 | 12/2011 | Breitbart et al. |
| 2012/0201790 | A1 | 8/2012 | Harats et al. |
| 2013/0011367 | A1 | 1/2013 | Harats et al. |
| 2013/0052165 | A1 | 2/2013 | Bangio et al. |
| 2013/0209450 | A1 | 8/2013 | Cohen et al. |
| 2013/0272998 | A1 | 10/2013 | Harats et al. |
| 2013/0280216 | A1 | 10/2013 | Cohen et al. |
| 2013/0280217 | A1 | 10/2013 | Cohen et al. |
| 2013/0295053 | A1 | 11/2013 | Bangio et al. |
| 2013/0296404 | A1 | 11/2013 | Harats et al. |
| 2013/0303595 | A1 | 11/2013 | Cohen et al. |

FOREIGN PATENT DOCUMENTS

| | | | |
|---|---|---|---|
| WO | WO 98/39465 | A2 | 9/1998 |
| WO | WO 00/06759 | | 2/2000 |
| WO | WO 00/74629 | | 12/2000 |
| WO | WO 01/83560 | | 11/2001 |
| WO | WO 02/10368 | | 2/2002 |
| WO | WO 02/40629 | | 5/2002 |
| WO | WO 03/000928 | | 1/2003 |
| WO | WO 03/033514 | | 4/2003 |
| WO | WO 03/038043 | | 5/2003 |
| WO | WO 03/039458 | A2 | 5/2003 |
| WO | WO 03/093409 | | 11/2003 |
| WO | WO 2004/031357 | A2 | 4/2004 |
| WO | WO 2004/035616 | A2 | 4/2004 |
| WO | WO 2004/061458 | A2 | 7/2004 |
| WO | WO 2004/113497 | | 12/2004 |
| WO | WO 2006/051545 | | 5/2006 |
| WO | WO 2007/096882 | | 8/2007 |
| WO | WO 2008/132729 | | 11/2008 |
| WO | WO 2011/083464 | | 7/2011 |
| WO | WO 2011/083466 | | 7/2011 |
| WO | WO 2011/086509 | A1 | 7/2011 |
| WO | WO 2012/052878 | A1 | 4/2012 |

OTHER PUBLICATIONS

Communication Pursuant to Article 94(3) EPC Dated Feb. 10, 2009 From the European Patent Office Re.: Application No. 02801473.6.
Communication Pursuant to Article 94(3) EPC Dated Feb. 16, 2009 From the European Patent Office Re.: Application No. 05806361.1.
Communication Pursuant to Article 94(3) EPC Dated Oct. 24, 2011 From the European Patent Office Re. Application No. 10184033.8.
Communication Pursuant to Article 94(3) EPC Dated Oct. 24, 2011 From the European Patent Office Re. Application No. 10185195.4.
Communication Pursuant to Article 94(3) EPC Dated Jan. 25, 2011 From the European Patent Office Re. Application No. 09168899.4.
Communication Pursuant to Article 94(3) EPC Dated May 29, 2008 From the European Patent Office Re.: Application No. 05806361.1 Mailed by Associate on Jun. 16, 2008.
Communication Pursuant to Article 96(2) EPC Dated May 3, 2006 From the European Patent Office Re.: Application No. EP 01996590.4.
Communication Pursuant to Article 96(2) EPC Dated Apr. 17, 2007 From the European Patent Office Re.: Application No. EP 02801473.6.
Communication Pursuant to Article 96(2) EPC Dated Apr. 17, 2007 From the European Patent Office Re.: Application No. EP 02801473.6 mailed by Associate only on May 31, 2007.
Communication Pursuant to Article 96(2) EPC Dated Dec. 21, 2006 From the European Patent Office Re.: Application No. 01996590.4.
Communication Pursuant to Article 96(2) EPC Dated Apr. 27, 2007 From the European Patent Office Re.: Application No. EP 01996590.4. Mailed by Associate on May 31, 2007.
Communication Pursuant to Article 96(2) EPC Dated Jul. 31, 2006 From the European Patent Office Re.: Application No. EP 03717516.3. Mailed by Associate on Aug. 17, 2006.
Communication Pursuant to Rule71(3) EPC Dated Mar. 13, 2012 From the European Patent Office Re. Application No. 10185195.4.
Communication Pursuant to Rules 70(2) and 70a (2) EPC and Reference to Rule 39(1) EPC Dated Feb. 21, 2011 From the European Patent Office Re. Application No. 10177257.2.
Communication Pursuant to Rules 70(2) and 70a(2) EPC and Reference to Rule 39(1) EPC Dated Apr. 4, 2011 From the European Patent Office Re. Application No. 10184033.8.
Communication Pursuant to Rules 70(2) and 70a(2) EPC and Reference to Rule 39(1) EPC Dated Apr. 4, 2011 From the European Patent Office Re. Application No. 10185195.4.
Communication Pursuant to Rules 70(2) and 70a(2) EPC and Reference to Rule 39(1) EPC Dated Jun. 21, 2010 From the European Patent Office Re. Application No. 09168899.4.
Communication Pursuant to Rules 70(2) and 70a(2) EPC and Reference to Rule 39(1) EPC Dated Nov. 21, 2011 From the European Patent Office Re. Application No. 10184033.8.
Communication Relating to the Results of the Extended International Search Dated Apr. 8, 2010 From the European Patent Office Re.: Application No. 09174998.6.
Communication Under Rule 71(3) EPC DAted Jun. 1, 2011 From the European Patent Office Re. Application No. 09168899.4.
Decision to Grant a European Patent Pursuant to Article 97(1) EPC Dated Oct. 7, 2011 From the European Patent Office Re. Application No. 09168899.4.
Dismissed Petition Dated Aug. 18, 2011 From the US Patent and Trademark Office Re. U.S. Appl. No. 10/988,487.
European Search Report and the European Search Opinion Dated May 17, 2010 From the European Patent Office Re. Application No. 09168899.4.
European Search Report and the European Search Opinion Dated Oct. 18, 2011 From the European Patent Office Re. Application No. 10185193.9.
European Search Report and the European Search Opinion Dated Jan. 19, 2011 From the European Patent Office Re. Application No. 10177257.2.
European Search Report and the European Search Opinion Dated Feb. 22, 2011 From the European Patent Office Re. Application No. 10185195.4.
European Search Report and the European Search Opinion Dated Feb. 24, 2011 From the European Patent Office Re. Application No. 10184033.8.
European Search Report and the European Search Opinion Dated Jul. 29, 2010 From the European Patent Office Re. Application No. 09176343.3.
Examination Report Dated Aug. 3, 2006 From the Intellectual Property Office of New Zealand Re.: Application No. 536578. Mailed by Associate Aug. 6, 2006.
Examination Report Dated Jun. 20, 2007 From the Government of India, Patent Office Re.: Application No. 2679/CHENP/2004.
Examination Report Dated Oct. 1, 2010 From the Intellectual Property Office of New Zealand Re. Application No. 581511.
Examination Report Dated Sep. 2, 2011 From the Austrian Patent Office on Behalf of the Intellectual Property Office of Singapore Re. Application No. 200907209-1.

(56) References Cited

OTHER PUBLICATIONS

Examination Report Dated Apr. 3, 2009 From the Intellectual Property Office of New Zealand Re.: Application No. 555612.
Examination Report Dated Jun. 3, 2011 From the Intellectual Property Office of New Zealand Re. Application No. 581511.
Examination Report Dated Sep. 5, 2005 From the Intellectual Property Office of New Zealand Re.: Application 536578. Mailed by Associate Oct. 12, 2005.
Examination Report Dated Aug. 6, 2009 From the Intellectual Property Office of New Zealand Re.: Application No. 555612.
Examination Report Dated Sep. 9, 2011 From the Instituto Mexicano de la Propriedad Industrial Re. Application No. MX/a/2007/005783 and Its Summary in English.
Examination Report Dated Jul. 12, 2007 From the Government of India, Patent Office Re.: Application No. 801/CHENP/2004.
Examination Report Dated Apr. 13, 2006 From the Government of India, Patent Office Re.: Application No. 743/CHENP/2003—in English only. Mailed by the Associate on Jun. 2, 2006.
Examination Report Dated Mar. 14, 2012 From the Instituto Mexicano de la Propricdad Industrial Re. Application No. MX/a/2011/012087 and Its Translation Into English.
Examination Report Dated Oct. 16, 2009 From the Intellectual Property Office of New Zealand Re.: Application No. 580289.
Examination Report Dated Jul. 18, 2007 From the Instituto Mexicano de la Propiedad Industrial Re. Application No. PA/a/2004/010711.
Examination Report Dated Jan. 26, 2011 From the Instituto Mexicano de la Propiedad Industrial Re. Application No. PA/a/2004/010711.
Examination Report Dated Nov. 30, 2011 From the Instituto Mexicano de la Propriedad Industrial Re. Application No. MX/a/2007/005783 and Its Translation Into English.
Examiner's Report Dated Dec. 7, 2010 From the Australian Government, IP Australia Re. Application No. 2005303385.
Examiner's Report Dated Dec. 10, 2008 From the Australian Government, IP Australia Re.: Application No. 2003222427.
Examiner's Report Dated Aug. 29, 2011 From the Australian Government, IP Australia Re.: Application No. 2011205076.
Formalities Examination—Adverse Report Dated May 23, 2012 From the Intellectual Property Office of Singapore Re. Application No. 201203215-7.
International Preliminary Examination Report Dated Jan. 5, 2005 From the International Preliminary Examining Authority Re.: Application No. PCT/IL02/00339.
International Preliminary Examination Report Dated May 26, 2005 From the International Preliminary Examining Authority Re.: Application No. PCT/IL03/00347.
International Preliminary Examination Report Dated Jan. 28, 2005 From the International Preliminary Examining Authority Re.: Application No. PCT/IL01/01059.
International Preliminary Report on Patentability Dated Nov. 12, 2009 From the International Bureau of WIPO Re.: Application No. PCT/IL2008/000543.
International Preliminary Report on Patentability Dated Jan. 22, 2009 From the International Bureau of WIPO Re.: Application No. PCT/IL2007/000242.
International Preliminary Report on Patentability Dated May 24, 2007 From the International Bureau of WIPO Re.: Application No. PCT/IL2005/001195.
International Search Report Dated Dec. 2, 2002 From the International Searching Authority Re.: Application No. PCT/IL02/00339.
International Search Report Dated Aug. 4, 2006 From the International Searching Authority Re.: Application No. PCT/IL05/01195.
International Search Report Dated May 4, 2004 From the International Searching Authority Re.: Application No. PCT/IL01/01059.
International Search Report Dated Sep. 18, 2008 From the International Searching Authority Re.: Application No. PCT/IL07/00242.
International Search Report Dated Apr. 29, 2009 From the International Searching Authority Re.: Application No. PCT/IL08/00543.
International Search Report or the Declaration Dated Jan. 28, 2005 From the International Searching Authority Re: Application No. PCT/IL03/00347.
Invitation to Pay Additional Fees Dated Jun. 1, 2006 From the International Searching Authority Re.: Application No. PCT/IL05/01195.
Invitation to Remedy Deficiencies Pursuant to Rule 30(3) EPC / Rule 163(3) EPC Dated Apr. 11, 2011 From the European Patent Office Re. Application No. 10185193.9.
Invitation to Remedy Deficiencies Pursuant to Rule 30(3) EPC / Rule 163(3) EPC Dated Mar. 16, 2010 From the European Patent Office Re.: Application No. 09176343.3.
Notice of Allowance Dated Jun. 2, 2011 From the US Patent and Trademark Office Re. U.S. Appl. No. 10/988,487.
Notice of Allowance Dated Feb. 10, 2012 From the US Patent and Trademark Office Re. U.S. Appl. No. 13/018,447.
Notice of Allowance Dated Jun. 11, 2009 From the US Patent and Trademark Office Re. U.S. Appl. No. 10/490,746.
Notice of Allowance Dated Jan. 12, 2011 From the US Patent and Trademark Office Re. U.S. Appl. No. 10/988,487.
Notice of Allowance Dated Aug. 14, 2008 From the US Patent and Trademark Office Re. U.S. Appl. No. 10/075,619.
Notice of Allowance Dated Mar. 21, 2012 From the US Patent and Trademark Office Re. U.S. Appl. No. 13/094,900.
Notice of Allowance Dated Jun. 28, 2011 From the US Patent and Trademark Office Re. U.S. Appl. No. 11/359,513.
Notice of Grant of the Patent Application Dated Aug. 31, 2010 From the Instituto Mexicano de la Propiedad Industrial Re.: Application No. PA/a/2004/003514.
Notice of Non-Compliant Amendment Dated Jul. 12, 2011 From the US Patent and Trademark Office Re.: U.S. Appl. No. 12/224,178.
Notice of Non-Compliant Amendment Dated Sep. 19, 2011 From the US Patent and Trademark Office Re. U.S. Appl. No. 12/224,178.
Office Action Dated May 3, 2012 From the Israel Patent Office Re. Application No. 211489 and Its Translation Into English.
Office Action Dated Apr. 4, 2012 From the Israel Patent Office Re. Application No. 201760 and Its Translation Into English.
Office Action Dated Jul. 4, 2011 From the Israel Patent Office Re.: Application No. 183187 and Its Translation Into English.
Office Action Dated Jan. 10, 2008 From the Israeli Patent Office Re.: Application No. 155940.
Office Action Dated Nov. 13, 2011 From the Israel Patent Office Re. Application No. 211489 and Its Translation Into English.
Office Action Dated Oct. 13, 2006 From the Patent Office of the People's Republic of China Re.: Application No. CN 03815262.2—English Translation only. (mailed by Associate only on Nov. 13, 2006.
Office Action Dated Sep. 20, 2007 From the Israeli Patent Office Re.: Application No. 155940.
Office Action Dated Nov. 21, 2011 From the Israel Patent Office Re. Application No. 201760 and Its Translation Into English.
Office Action Dated Jan. 22, 2012 From the Israel Patent Office Re.: Application No. 183187 and Its Translation into English.
Office Action Dated Jun. 25, 2012 From the Israel Patent Office Re.: Application No. 183187 and Its Translation Into English.
Office Action Dated Apr. 27, 2008 From the Korean Intellectual Property Office Re.: Application No. 2004-7005720 and its translation in English. Mailed by Associate May 23, 2008.
Office Action Dated Dec. 29, 2009 From the Israel Patent Office Re.: Application No. 183187 and Its Translation Into English.
Office Action Dated Jul. 31, 2007 From the Japanese Patent Office Re.: Application No. 2004-501545. Mailed by the Associate on Aug. 8, 2007.
Office Action Dated Jul. 31, 2007 From the Japanese Patent Office Re.: Application No. 2002-543626 Mailed by Associate Aug. 23, 2007;.
Office Action Dated Oct. 31, 2010 From the Israel Patent Office Re.: Application No. 183187 and Its Translation Into English.
Official Action Dated Oct. 2, 2008 From the US Patent and Trademark Office Re.: U.S. Appl. No. 11/359,513.
Official Action Dated Aug. 4, 2009 From the US Patent and Trademark Office Re.: U.S. Appl. No. 11/359,513.
Official Action Dated Jan. 4, 2008 From the US Patent and Trademark Office Re.: U.S. Appl. No. 10/988,487.

(56) References Cited

OTHER PUBLICATIONS

Official Action Dated Jun. 4, 2007 From the US Patent and Trademark Office Re.: U.S. Appl. No. 10/975,619.
Official Action Dated Jun. 4, 2010 From the US Patent and Trademark Office Re.: U.S. Appl. No. 12/457,200.
Official Action Dated Aug. 5, 2010 From the US Patent and Trademark Office Re.: U.S. Appl. No. 11/359,513.
Official Action Dated Apr. 6, 2007 From the US Patent and Trademark Office Re.: U.S. Appl. No. 10/975,619.
Official Action Dated Dec. 6, 2010 From the US Patent and Trademark Office Re.: U.S. Appl. No. 12/224,178.
Official Action Dated Jul. 6, 2010 From the US Patent and Trademark Office Re.: U.S. Appl. No. 11/790,992.
Official Action Dated May 6, 2009 From the US Patent and Trademark Office Re.: U.S. Appl. No. 11/359,513.
Official Action Dated Dec. 7, 2011 From the US Patent and Trademark Office Re.: U.S. Appl. No. 13/094,900.
Official Action Dated Oct. 7, 2010 From the US Patent and Trademark Office Re.: U.S. Appl. No. 12/224,178.
Official Action Dated Jul. 8, 2010 From the US Patent and Trademark Office Re.: U.S. Appl. No. 10/988,487.
Official Action Dated Apr. 9, 2008 From the US Patent and Trademark Office Re.: U.S. Appl. No. 10/490,746.
Official Action Dated Sep. 9, 2011 From the US Patent and Trademark Office Re.: U.S. Appl. No. 13/098,512.
Official Action Dated Apr. 10, 2008 From the US Patent and Trademark Office Re.: U.S. Appl. No. 10/975,619.
Official Action Dated Jul. 10, 2007 From the US Patent and Trademark Office Re.: U.S. Appl. No. 10/490,746.
Official Action Dated Nov. 10, 2010 From the US Patent and Trademark Office Re.: U.S. Appl. No. 12/457,200.
Official Action Dated Oct. 11, 2006 From the US Patent and Trademark Office Re.: U.S. Appl. No. 10/490,746.
Official Action Dated Jul. 12, 2011 From the US Patent and Trademark Office Re.: U.S. Appl. No. 12/591,252.
Official Action Dated Jul. 12, 2011 From the US Patent and Trademark Office Re.: U.S. Appl. No. 13/018,447.
Official Action Dated Nov. 12, 2009 From the US Patent and Trademark Office Re.: U.S. Appl. No. 10/988,487.
Official Action Dated Apr. 13, 2012 From the US Patent and Trademark Office Re.: U.S. Appl. No. 13/098,512.
Official Action Dated Dec. 13, 2011 From the US Patent and Trademark Office Re.: U.S. Appl. No. 12/224,178.
Official Action Dated May 13, 2010 From the US Patent and Trademark Office Re.: U.S. Appl. No. 12/222,439.
Official Action Dated Oct. 13, 2010 From the US Patent and Trademark Office Re.: U.S. Appl. No. 12/222,439.
Official Action Dated Jan. 14, 2010 From the US Patent and Trademark Office Re.: U.S. Appl. No. 11/359,513.
Official Action Dated Jul. 14, 2004 From the US Patent and Trademark Office Re.: U.S. Appl. No. 10/135,447.
Official Action Dated Jun. 14, 2012 From the US Patent and Trademark Office Re.: U.S. Appl. No. 13/163,767.
Official Action Dated Nov. 14, 2008 From the US Patent and Trademark Office Re.: U.S. Appl. No. 10/490,746.
Official Action Dated Dec. 15, 2009 From the US Patent and Trademark Office Re.: U.S. Appl. No. 11/790,992.
Official Action Dated Dec. 15, 2011 From the US Patent and Trademark Office Re. U.S. Appl. No. 12/591,252.
Official Action Dated Nov. 17, 2011 From the US Patent and Trademark Office Re. U.S. Appl. No. 13/098,512.
Official Action Dated Jan. 22, 2010 From the US Patent and Trademark Office Re.: U.S. Appl. No. 12/457,200.
Official Action Dated Dec. 23, 2009 From the US Patent and Trademark Office Re.: U.S. Appl. No. 12/222,439.
Official Action Dated Jun. 24, 2009 From the US Patent and Trademark Office Re.: U.S. Appl. No. 12/222,439.
Official Action Dated Jan. 26, 2011 From the US Patent and Trademark Office Re.: U.S. Appl. No. 11/359,513.
Official Action Dated Sep. 26, 2011 From the US Patent and Trademark Office Re. U.S. Appl. No. 13/018,447.
Official Action Dated Dec. 29, 2006 From the US Patent and Trademark Office Re.: U.S. Appl. No. 10/490,746.
Official Action Dated Jul. 29, 2009 From the US Patent and Trademark Office Re.: U.S. Appl. No. 10/490,746.
Official Action Dated Aug. 31, 2009 From the US Patent and Trademark Office Re.: U.S. Appl. No. 11/790,992.
Official Communication Dated Feb. 1, 2008 From the Instituto Mexicano de la Propiedad Industrial Re.: Application No. PA/a/2004/003514 and its summary in English by Associate.. Mailed by Associate May 7, 2008.
Official Communication Dated Jul. 14, 2010 From the Instituto Mexicano de la Propiedad Industrial Re.: Application No. PA/a/2004/003514 and Its Summary in English by Associate.
Official Communication Dated Feb. 28, 2008 From the Instituto Mexicano de la Propiedad Industrial Re.: Application No. PA/a/2003/004325, and its Summary in English by Associate. Mailed by Associate Apr. 16, 2008.
Partial European Search Report Dated Feb. 23, 2010 From the European Patent Office Re.: Application No. 09168899.4.
Requisition by the Examiner Dated May 14, 2010 From the Canadian Intellectual Property Office Re. Application No. 2,483,996.
Requisition by the Examiner Dated Dec. 16, 2008 From the Canadian Intellectual Property Re.: 2,429,342.
Requisition by the Examiner Dated Jan. 18, 2010 From the Canadian Intellectual Property Office Re.: Application No. 2,463,816.
Requisition by the Examiner Dated Dec. 21, 2010 From the Canadian Intellectual Property Re.: 2,429,342.
Requisition by the Examiner Dated Sep. 22, 2011 From the Canadian Intellectual Property Re.: 2,429,342.
Requisition by the Examiner Dated Sep. 23, 2011 From the Canadian Intellectual Property Office Re.: Application No. 2,463,816.
Response Dated Aug. 1, 2011 to Notice of Non-Compliant Amendment of Jul. 12, 2011 From the US Patent and Trademark Office Re.: U.S. Appl. No. 12/224,178.
Response Dated Dec. 2, 2010 to Office Action of Jul. 30, 2010 From the State Intellectual Property Office of the People's Republic of China Re. Application No. 200580046412.8.
Response Dated Jan. 2, 2012 to Office Action of Sep. 28, 2011 From the State Intellectual Property Office of the People's Republic of China Re. Application No. 200880022935.2.
Response Dated Feb. 3, 2011 to Official Action of Nov. 10, 2010 From the US Patent and Trademark Office Re.: U.S. Appl. No. 12/457,200.
Response Dated Jan. 3, 2011 to Official Action of Oct. 13, 2010 From the US Patent and Trademark Office Re.: U.S. Appl. No. 12/222,439.
Response Dated Nov. 4, 2009 to Official Action of Aug. 4, 2009 From the US Patent and Trademark Office Re.: U.S. Appl. No. 11/359,513.
Response Dated Apr. 5, 2011 to Search Report and Written Opinion of Nov. 11, 2010 From the Intellectual Property Office of Singapore Issued by the Austrian Patent Office Re. Application No. 200907209-1.
Response Dated Dec. 5, 2010 to Official Action of Aug. 5, 2010 From the US Patent and Trademark Office Re.: U.S. Appl. No. 11/359,513.
Response Dated May 5, 2011 to Official Action of Dec. 6, 2010 From the US Patent and Trademark Office Re.: U.S. Appl. No. 12/224,178.
Response Dated Oct. 5, 2010 to Official Action of Jul. 6, 2010 From the US Patent and Trademark Office Re.: U.S. Appl. No. 11/790,992.
Response Dated Oct. 5, 2011 to Official Action of Jul. 12, 2011 From the US Patent and Trademark Office Re. U.S. Appl. No. 12/591,252.
Response Dated Sep. 5, 2011 to European Search Report and the European Search Opinion of Feb. 22, 2011 From the European Patent Office Re. Application No. 10185195.4.
Response Dated Jun. 6, 2011 to Requisition by the Examiner of Dec. 21, 2010 From the Canadian Intellectual Property Re.: 2,429,342.
Response Dated Nov. 7, 2010 to Examination Report of Oct. 16, 2009 From the Intellectual Property Office of New Zealand Re.: Application No. 580289.
Response Dated Oct. 7, 2010 to Official Action of Jul. 8, 2010 From the US Patent and Trademark Office Re.: U.S. Appl. No. 10/988,487.
Response Dated Aug. 8, 2011 to Official Action of Jul. 12, 2011 From the US Patent and Trademark Office Re. U.S. Appl. No. 13/018,447.

(56) References Cited

OTHER PUBLICATIONS

Response Dated Nov. 8, 2010 to Official Action of Oct. 7, 2010 From the US Patent and Trademark Office Re.: U.S. Appl. No. 12/224,178.
Response Dated Nov. 8, 2011 to Examination Report of Sep. 9, 2011 From the Instituto Mexicano de la Propriedad Industrial Re. Application No. MX/a/2007/005783.
Response Dated Jan. 10, 2010 to Examiner's Report of Dec. 10, 2008 From the Australian Government, IP Australia Re.: Application No. 2003222427.
Response Dated Oct. 10, 2011 to Official Action of Sep. 9, 2011 From the US Patent and Trademark Office Re. U.S. Appl. No. 13/098,512.
Response Dated Aug. 11, 2011 to Notice of Reason for Rejection of Jun. 10, 2011 From the Japanese Patent Office Re. Application No. 2007-540833.
Response Dated Apr. 12, 2010 to Official Action of Nov. 12, 2009 From the US Patent and Trademark Office Re.: U.S. Appl. No. 10/988,487.
Response Dated Aug. 12, 2010 to Official Action of May 13, 2010 From the US Patent and Trademark Office Re.: U.S. Appl. No. 12/222,439.
Response Dated May 12, 2010 to Invitation to Remedy Deficiencies Pursuant to Rule 30(3) EPC / Rule 163(3) EPC of Mar. 16, 2010 From the European Patent Office Re.: Application No. 09176343.3.
Response Dated Sep. 12, 2011 to Communication Pursuant to Rules 70(2) and 70a(2) EPC and Reference to Rule 39(1) EPC of Apr. 4, 2011 From the European Patent Office Re. Application No. 10185195.4.
Response Dated May 13, 2010 to Official Action of Jan. 14, 2010 From the US Patent and Trademark Office Re.: U.S. Appl. No. 11/359,513.
Response Dated Apr. 14, 2010 to Official Action of Dec. 15, 2009 From the US Patent and Trademark Office Re.: U.S. Appl. No. 11/790,992.
Response Dated Apr. 14, 2011 to Official Action of Jan. 26, 2011 From the US Patent and Trademark Office Re.: U.S. Appl. No. 11/359,513.
Response Dated Aug. 14, 2011 to Communication Pursuant to Rules 70(2) and 70a (2) EPC and Reference to Rule 39(1) EPC of Feb. 21, 2011 From the European Patent Office Re. Application No. 10177257.2.
Response Dated Jul. 14, 2010 to Requisition by the Examiner of Jan. 18, 2010 From the Canadian Intellectual Property Office Re.: Application No. 2,463,816.
Response Dated Dec. 15, 2010 to European Search Report and the European Search Opinion of May 17, 2010 From the European Patent Office Re. Application No. 09168899.4.
Response Dated Feb. 15, 2011 to European Search Report and the European Search Opinion of Jul. 29, 2010 From the European Patent Office Re. Application No. 09176343.3.
Response Dated Nov. 17, 2011 to Communication Pursuant to Article 94(3) EPC of Oct. 24, 2011 From the European Patent Office Re. Application No. 10185195.4.
Response Dated Jul. 18, 2011 to Examiner's Report of Dec. 7, 2010 From the Australian Government, IP Australia Re. Application No. 2005303385.
Response Dated Oct. 18, 2011 to Notice of Non-Compliant Amendment of Sep. 19, 2011 From the US Patent and Trademark Office Re. U.S. Appl. No. 12/224,178.
Response Dated Dec. 19, 2011 to the Communication Pursuant to Article 94(3) EPC of Sep. 2, 2011 From the European Patent Office Re. Application No. 09174998.6.
Response Dated May 20, 2010 to Communication Relating to the Results of the Extended International Search of Apr. 8, 2010 From the European Patent Office Re.: Application No. 09174998.6.
Response Dated Nov. 20, 2011 to Communication Pursuant to Article 94(3) EPC of Oct. 24, 2011 From the European Patent Office Re. Application No. 10184033.8.
Response Dated Apr. 22, 2010 to Official Action of Dec. 23, 2009 From the US Patent and Trademark Office Re.: U.S. Appl. No. 12/222,439.
Response Dated Feb. 22, 2010 to Official Action of Jan. 22, 2010 From the US Patent and Trademark Office Re.: U.S. Appl. No. 12/457,200.
Response Dated Aug. 24, 2010 to Official Action of May 27, 2010 From the US Patent and Trademark Office Re.: U.S. Appl. No. 12/371,930.
Response Dated Nov. 24, 2011 to Official Action of Sep. 26, 2011 From the US Patent and Trademark Office Re. U.S. Appl. No. 13/018,447.
Response Dated Aug. 25, 2010 to Official Action of Jun. 4, 2010 From the US Patent and Trademark Office Re.: U.S. Appl. No. 12/457,200.
Response Dated Aug. 25, 2010 to Official Communication of Jul. 14, 2010 From the Instituto Mexicano de la Propiedad Industrial Re.: Application No. PA/a/2004/003514.
Response Dated Oct. 25, 2011 to Examination Report of Jun. 3, 2011 From the Intellectual Property Office of New Zealand Re. Application No. 581511.
Response Dated May 26, 2011 to the Invitation to Remedy Deficiencies Pursuant to Rule 30(3) EPC / Rule 163(3) EPC of Apr. 11, 2011 From the European Patent Office Re. Application No. 10185193.9.
Response Dated Apr. 27, 2011 to Communication Pursuant to Article 94(3) EPC of Jan. 25, 2011 From the European Patent Office Re. Application No. 09168899.4.
Response Dated Jun. 27, 2011 to Examiner's Report of Dec. 7, 2010 From the Australian Government, IP Australia Re. Application No. 2005303385.
Response Dated Sep. 27, 2011 to Communication Pursuant to Rules 70(2) and 70a(2) EPC and Reference to Rule 39(1) EPC of Apr. 4, 2011 From the European Patent Office Re. Application No. 10184033.8.
Response Dated Feb. 28, 2011 to Office Action of Oct. 31, 2010 From the Israel Patent Office Re.: Application No. 183187.
Response Dated Apr. 29, 2010 to Office Action of Dec. 29, 2009 From the Israel Patent Office Re.: Application No. 183187.
Response Dated Nov. 30, 2011 to Office Action of Jul. 4, 2011 From the Israel Patent Office Re.: Application No. 183187.
Response Dated Dec. 31, 2010 to Office Action of Sep. 14, 2010 From the State Intellectual Property Office of the People's Republic of China Re. Application No. 200910137707.6.
Restriction Official Action Dated Apr. 6, 2012 From the US Patent and Trademark Office Re. U.S. Appl. No. 13/163,767.
Search Report and Written Opinion Dated Oct. 7, 2010 From the Intellectual Property Office of Singapore Issued by the Austrian Patent Office Re. Application No. 200907209-1.
Search Report and Written Opinion Dated Apr. 21, 2009 From the Intellectual Property Office of Singapore Issued by the Austrian Patent Office Re.: Application No. 200703466-3.
Summons to Attend Oral Proceedings Pursuant to Rule 115(1) EPC Dated Jul. 13, 2009 From the European Patent Office Re.: Application No. 05806361.1.
Summons to Attend Oral Proceedings Pursuant to Rule 115(1) EPC Dated Sep. 14, 2009 From the European Patent Office Re.: Application No. 02801473.6.
Supplementary European Search Report and the European Search Opinion Dated Oct. 17, 2007 From the European Patent Office Re.: Application EP 05806361. Mailed Oct. 18, 2007 by Associate.
Supplementary European Search Report Dated Mar. 21, 2006 From the European Patent Office Re.: Application No. EP 02801473.6.
Supplementary European Search Report Dated Oct. 28, 2005 From the European Patent Office Re.: Application No. EP 03717516.
Supplementary Partial European Search Report Dated Nov. 15, 2004 From the European Patent Office Re.: Application EP 01996590.
Supplementary Partial European Search Report Dated Nov. 15, 2004 From the European Patent Office Re. Application No. 01996590.4.
Translation of Notice of Reason for Rejection Dated Jun. 1, 2012 From the Japanese Patent Office Re. Application No. 2007-540833.
Translation of Notice of Reason for Rejection Dated Jun. 10, 2011 From the Japanese Patent Office Re. Application No. 2007-540833.
Translation of Notice of Reason for Rejection Dated Oct. 16, 2007 From the Japanese Patent Office Re.: Application No. 2003-536253 Mailed by Associate on Oct. 25, 2007.

(56) References Cited

OTHER PUBLICATIONS

Translation of Notice of Reason for Rejection Dated May 28, 2008 From the Japanese Patent Office Re.: Application No. 202-543626 Mailed by Associate Jun. 9, 2008.
Translation of Notice of the Reason for Rejection Dated Jan. 7, 2009 From the Korean Intellectual Property Office Re.: Application No. 2008-7018598.
Translation of Office Action Dated Jan. 12, 2012 From the State Intellectual Property Office of the People's Republic of China Re. Application No. 200580046412.8.
Translation of Office Action Dated Mar. 12, 2012 From the State Intellectual Property Office of the People's Republic of China Re. Application No. 200880022935.2.
Translation of Office Action Dated Sep. 14, 2010 From the State Intellectual Property Office of the People's Republic of China Re. Application No. 200910137707.6.
Translation of Office Action Dated Sep. 28, 2011 From the State Intellectual Property Office of the People's Republic of China Re. Application No. 200880022935.2.
Translation of Office Action Dated Jul. 30, 2010 From the State Intellectual Property Office of the People's Republic of China Re. Application No. 200580046412.8.
Translation of Office Action Dated Mar. 30, 2012 From the State Intellectual Property Office of the People's Republic of China Re. Application No. 200910137707.6.
Written Opinion Dated Nov. 2, 2004 From the International Preliminary Examining Authority Re.: Application PCT/IL01/01059.
Written Opinion Dated Sep. 18, 2008 From the International Searching Authority Re.: Application No. PCT/IL07/00242.
Written Opinion Dated Apr. 29, 2009 From the International Searching Authority Re.: Application No. PCT/IL08/00543.
Written Opinion Dated Oct. 29, 2003 From the International Preliminary Examining Authority Re.: Application No. PCT/IL02/00339.
Written Opinion of the International Searching Authority Dated Aug. 4, 2006 From the International Searching Authority by the Patent Cooperation Treaty Re.: Application No. PCT/IL05/01195.
Adachi et al. "A Midkine Promoter-Based Conditionally Replicative Adenovirus for Treatment of Pediatric Solid Tumors and Bone Marrow Tumor Purging", Cancer Research, 61: 7882-7888, 2001.
Aird et al. "Human von Willebrand Factor Gene Sequences Target Expression to a Subpopulation of Endothelial Cells in Transgenic Mice", Proc. Natl. Acad. Sci. USA, 92: 4567-4571, 1995.
Aoki et al. "In Vivo Transfer Efficiency of Antisense Oligonucleotides Into the Myocardium Using HVJ-Liposome Method", Biochemical and Biophysical Research Communications, 231: 540-545, 1997.
Araki et al. "Ninjurin2, A Novel Homophilic Adhesion Molecule, Is Expressed in Mature Sensory and Enteric Neurons and Promotes Neurite Outgrowth", The Journal of Neuroscience, 20(1): 187-195, 2000.
Arap et al. "Cancer Treatment by Targeted Drug Delivery to Tumor Vasculature in a Mouse Model", Science, New Series, 279(5349): 377-380, 1998.
Ausprunk et al. "Migration and Proliferation of Endothelial Cells in Preformed and Newly Formed Blood Vessels During Tumor Angiogenesis", Microvascular Research, 14: 53-65, 1977.
Barcelos et al. "Impaired Inflammatory Angiogenesis, But Not Leukocyte Influx, in Mice Lacking TNFR1", Journal of Leukocyte Biology, 78: 352-358, Aug. 2005.
Bobek et al. "Gene Therapy of the Ischemic Lower Limb—Therapeutic Angiogenesis", Vascular Pharmacology, 44: 395-405, 2006.
Boldin et al. "A Novel Protein That Interacts With the Death Domain of Fas/APO1 Contains a Sequence Motif Related to the Death Domain", The Journal of Biological Chemistry, XP002035462, 270(14): 7795-7798, Apr. 7, 1995.
Brown et al. "Neovascularisation and Its Role in the Osteoarthritic Process", Annals of the Rheumatic Diseases, 47: 881-885, 1988.
Bu et al. "Identification of an Endothelial Cell-Specific Regulatory Region in the Murine Endothelin-1 Gene", The Journal of Biological Chemistry, XP002980773, 272(51): 32613-32622, Dec. 19, 1997. Fig.5A, P.32614, col. 1, Para 2-5, Figs.1-7.
Carmeliet et al. "Growing Better Blood Vessels", Nature Biotechnology, 19: 1019-1020, 2001.
Chattopadhyay et al. "Effect of Single Amino Acid Mutations in the Conserved GDNQ Motif of L Protein of Rinderpest Virus on RNA Synthesis In Vitro and In Vivo", Virus Research, 99: 139-145, 2004.
Chen et al. "Upstream St

(56) References Cited

OTHER PUBLICATIONS

Gray et al. "Cloning of Human Tumor Necrosis Factor (TNF) Receptor cDNA and Expression of Recombinant Soluble TNF-Binding Protein", Proc. Natl. Acad. Sci. USA, 87: 7380-7384, Oct. 1990.
Greenberger et al. "Transcription-Controlled Gene Therapy Against Tumor Angiogenesis", The Journal of Clinical Investigation, XP002349281, 113(7): 1017-1024, Apr. 1, 2004. Abstract, p. 1018, p. 1019, LLC Model, Fig.2A, p. 1017 Right col. Para 1, p. 1019 Left col. Para 1, p. 1020 Fig. 2A.
Gridley et al. "Combining Gene Therapy and Radiation Against Cancer", Current Gene Therapy, 4(3): 281-284, Sep. 2004. Abstract.
Gu et al. "HTERT Promoter Induces Tumor-Specific Bax Gene Expression and Cell Killing in Syngenic Mouse Tumor Model and Prevents Systemic Toxicity", Gene Therapy, 9: 30-37, 2002.
Harada et al. "Basic Fibroblast Growth Factor Improves Myocardial Function in Chronically Ischemic Porcine Hearts", Journal of Clinical Investigation, 94: 623-630, 1994.
Harats et al. "Targeting Gene Expression to the Vascular Wall in Transgenic Mice Using the Murine Preproendothelin-1 Promoter", Journal of Clinical Investigation, 95(3): 1335-1344, Mar. 1995. p. 1336, Fig.1.
Hoefer et al. "Direct Evidence for Tumor Necrosis Factor—? Signaling in Arteriogenesis", Circulation, 105: 1639-1641, Apr. 9, 2002.
Hu et al. "Hypoxia Regulates Expression of the Endothelial-1 Gene Through a Proximal-Inducible Factor-1 Binding Site on the Antisence Strand", Biochemical and Biophysical Research Communication, 245: 894-899, 1998.
Iris et al. "Dense Alu Clustering and A Potential New Member of the NF?B Family Within a 90 Kilobase HLA Class III Segment", Nature Genetics, 3: 137-145, 1993.
Jaeger et al. "Endothelial Cell-Specific Transcriptional Targeting From A Hybrid Long Terminal Repeat Retrovirus Vector Containing Human Prepro-Endothelin-1 Promoter Sequences", Journal of Virology, 73(12): 9702-9709, 1999.
Jones et al. "A Portable Regulatory Element Directs Specific Expression of the *Caenorhabditis elegans* Ubiquitin Gene UBQ-2 in the Somatic Gonad", Developmental Biology, 171: 60-72, 1995.
Jornot et al. "N-Acetylsyteine Augments Adenovirus-Mediated Gene Expression in Human Endothelial Cells by Enhancing Tansgene Transcription and Virus Entry", The Journal of Gene Medicine, 4: 54-65, 2002.
Joshi et al. "Endothelial Cells Adhere to the RGD Domain and the Fibrinogen-Like Terminal Knob of Tenascin", Journal of Cell Science, 106: 389-400, 1993.
Juengst "What Next for Human Gene Therapy? Gene Transfer Often Has Multiple and Unpredictable Effects on Cells", BMJ, 326: 1410-1411, Jun. 28, 2003.
Kaiser et al. "Platelet-Derived Growth Factor, Intimal Hyperplasia, and Ischemic Complications in Giant Cell Arteritis", Arthritis & Rheumatism, 41(4): 623-633, 1998.
Kaito et al. "Potentiation of the Activity of Bone Morphogenetic Protein-2 in Bone Regeneration by a PLA-PEG/Hydroxyapatite Composite", Biomaterials, 26: 73-79, 2005.
Kambara et al. "Combined Radiation and Gene Therapy for Brain Tumors With Adenovirus-Mediated Transfer of Cytosine Deaminase and Uracil Phosphoribosyltransferase Genes", Cancer Gene Therapy, 9: 840-845, 2002.
Kaplan et al. "Fas Ligand (CD95 Ligand) Controls Angiogenesis Beneath the Retina", Nature Medicine, 5(3): 292-297, Mar. 1999.
Kay et al. "Viral Vectors for Gene Therapy: The Art of Turning Infectious Agents Into Vehicles of Therapeutics", Nature Medicine, 7(1): 33-40, Jan. 2001.
Kaye et al. "A Single Amino Acid Substitution Results in a Retinoblastoma Protein Defective in Phosphorylation and Oncoprotein Binding", Proc. Natl. Acad. Sci. USA, 87: 6922-6926, Sep. 1990.
Khan et al. "Gene Therapy Progeress and Prospects: Therapeutic Angiogenesis for Limb and Myocardial Ischemia", Gene Therapy, 10: 285-291, 2003.
Kodama et al. "The Features and Shortcomings for Gene Delivery of Current Non-Viral Carriers", Current Medicinal Chemistry, 13: 2155-2161, 2006.
Kolesnick et al. "Radiation and Ceramide-Induced Apoptosis", Oncogene, 22: 5897-5906, 2003.
Kong et al. "Gene Therapy Strategies for Tumor Antiangiogenesis", Journal of the National Cancer Institute, 90(4): 273-286, 1998.
Korhonen et al. "Endothelial-Specific Gene Expression Directed by the TIE Gene Promoter In Vivo", Blood, 86(5): 1828-1835, 1995.
Koshikawa et al. "Therapeutic Efficacy of the Suicide Gene Driven by the Promoter of Vascular Endothelial Growth Factor Gene Against Hypoxic Tumor Cells", Cancer Research, XP001024127, 60(11): 2936-2941, Jun. 1, 2000.
Koyama et al. "Migratory and Proliferative Effect of Platelet-Derived Growth Factor in Rabbit Retinal Endothelial Cells: Evidence of an Autocrine Pathway of Platelet-Derived Growth Factor", Journal of Cellular Physiology, 158: 1-6, 1994.
Kronenwett et al. "Oligodeoxyribonucleotide Uptake in Primary Human Hematopoietic Cells Is Enhanced by Cationic Lipids and Depends on the Hematopoietic Cell Subset", Blood, 91(3): 852-862, 1998.
Lahav et al. "Endothelin Receptor B Inhibition Triggers Apoptosis and Enhances Angiogenesis in Melanomas", Cancer Research, 64: 8945-8953, Dec. 16, 2004.
Lavigne et al. "Enhanced Antisense Inhibition of Human Immunodeficiency Virus Type 1 in Cell Cultures by DLS Delivery System", Biochemical and Biophysical Research Communications, 237: 566-571, 1997.
Layne et al. "Characterization of the Mouse Aortic Carboxypeptidase-Like Protein Promoter Reveals Activity in Differentiated and Dedifferentiatid Vascular Smooth Muscle Cells", Circulation Research, 90: 728-736, 2002.
Lebedeva et al. "Restoring Apoptosis as a Strategy for Cancer Gene Therapy: Focus on P53 and MDA-7", Seminars in Cancer Biology, 13: 169-178, 2003.
Lee et al. "Functional Analysis of the Endothelin-1 Gene Promoter", Journal of Biological Chemistry, 265(18): 10446-10450, 1990. Fig.1, wherein Nucleotides-124 to-118 Are Identical to SEQ ID No. 5.
Li et al. "Transcriptional Regulation of Fas Gene Expression by GA-Binding Protein and AP-1 in T Cells Antigen Receptor CD3 Complex-Stimulated T Cells", The Journal of Biological Chemistry, 274(49): 35203-35210, Dec. 3, 1999.
Liu et al. "Restenosis After Coronary Angioplasty. Potential Biologic Determinants and Role of Intimal Hyperplasia", Circulation, 79: 1374-1387, 1989.
Lowe et al. "Osteopetrosis in Src-Deficient Mice Is Due to an Autonomous Defect of Osteoclasts", Proc. Natl. Acad. Sci. USA, 90: 4485-4489, 1993.
Luft "Making Sense Out of Antisense Oligodeoxynucleotide Delivery: Getting There Is Half the Fun", Journal of Molecular Medicine, 76: 75-76, 1998.
Lyden "Impaired Recruitment of Bone-Marrow-Derived Endothelial and Hematopoietic Precursor Cells Blocks Tumor Angiogenesis and Growth", Nature Medicine, 7(11): 1194-1201, 2001.
Micheau et al. "STAT-1-Independent Upregulation of FADD and Procaspase-3 and -8 in Cancer Cells Treated With Cytotoxic Drugs", Biochemical and Biophysical Research Communications, 256: 603-607, 1999.
Minchenko et al. "Regulation of Endothelin-1 Gene Expression in Human Microvascular Endothelial Cells by Hypoxia and Cobalt: Role of Hypoxia Responsive Element", Molecular and Cellular Biochemistry, XP002305520, 208(1-2): 53-62, May 2000. p. 57, l-h col., § 2-p. 57, r-h col., Last §, Fig.2.
Modlich et al. "Increasing Endothelial Cell Specific Expression by the Use of Heterologous Hypoxic and Cytokine-Iducible Enhancers", Gene Therapy, 7: 896-902, 2000.
Morishita et al. "A Novel Promoter for Vascular Endothelial Growth Factor Receptor (Flt-1) That Confers Endothelial-Specific Gene Expression", The Journal of Biological Chemistry, 270(46): 27948-27953, 1995.
Newman et al. "PECAM-1 (CD31) Cloning and Relation to Adhesion Molecules of the Immunoglobulin Gene Superfamily", Science, New Series, 247(4947): 1219-1222, 1990.

(56) References Cited

OTHER PUBLICATIONS

Nicklin et al. "Selective Targeting of Gene Transfer to Vascular Endothelial Cells by Use of Peptides Isolated by Phage Display", Circulation, 102: 231-237, 2000.
Nishikawa et al. "Adenovirus-Mediated MDA-7 (IL24) Gene Therapy Suppresses Angiogenesis and Sensitizes NSCLC Xenograft Tumors to Radiation", Molecular Therapy, 9(6): 818-828, Jun. 2004.
O'Reilly et al. "Endostatin: An Endogenous Inhibitor of Angiogenesis and Tumor Growth", Cell, 88: 277-285, 1997.
Ozawa et al. "Histologic Changes of Nonbiodegradable and Biodegradable Biomaterials Used to Repair Right Ventricular Heart Defects in Rats", The Journal of Thoracic and Cardiovascular Surgery, 124(6): 1157-1164, 2002.
Palu et al. "In Pursuit of New Developments for Gene Therapy of Human Diseases", Journal of Biotechnology, 68: 1-13, 1999.
Papadakis et al. "Promoters and Control Elements: Designing Expression Cassettes for Gene Therapy," Current Gene Therapy 4: 89-113, 2004.
Patan et al. "Intussusceptive Microvascular Growth in a Human Colon Adenocarcinoma Xenograft: A Novel Mechanism of Tumor Angiogenesis", Microvascular Research, 51: 260-272, 1996.
Patil et al. "DNA-Based Therapeutics and DNA Delivery Systems: A Comprehensive Review", The AAPS Journal, 7(1): E61-E77, 2005.
Peled et al. "Systemic Administration of a Conditionally Replicating Adenovirus, Targeted to Angiogenesis, Reduced Lung Metastasis Burden in Cotton Rats", Clinical Cancer Research, XP002579967, 15(5): 1664-1673, Mar. 1, 2009.
Peng et al. "The Use of the L-Plastin Promoter for Adnoviral-Mediated, Tumor-Specific Gene Expression in Ovarian and Bladder Cancer Cell Lines", Cancer Research, 61: 4405-4413, 2001.
Penland et al. "Combining Anti-VEGF Approaches With Oxaliplatin in Advanced Colorectal Cancer", Clinical Colorectal Cancer Supplement, 4(Suppl. 2): S74-S80, Oct. 2004.
Percy et al. "Sequence Analysis of the 3' Hypoxia-Responsive Element of the Human Erythropoietin Gene in Patients With Erythrocytosis", Biochemical and Molecular Medicine, 62: 132-134, 1997.
Plump et al. "Severe Hypercholesterolemia and Atherosclerosis in Apolipoprotein E-Deficient Mice Created by Homologous Recombination in ES Cells", Cell, 71: 343-353, 1992.
Rajur et al. "Covalent Protein-Oligonucleotide Conjugates for Efficient Delivery of Antisense Molecules", Bioconjugate Chemistry, 8: 935-940, 1997.
Rein et al. "Current Developments in Adenovirus-Based Cancer Gene Therapy", Future Oncology, 2(1): 137-143, Feb. 2006.
Richardson et al. "Polymeric System for Dual Growth Factor Delivery", Nature Biotechnology, 19: 1029-1034, 2001.
Risau "Mechanisms of Angiogenesis", Nature, 386: 671-674, 1997.
Rius et al. "Cloning of the Promoter Region of Human Endoglin, the Target Gene for Hereditary Hemorrhagic Telangiectasia Type 1", Blood, 92(12): 4677-4690, 1998.
Sano et al. "Functional Blockade of Platelet-Derived Growth Factor Receptor-? But Not of Receptor-? Prevents Vascular Smooth Muscle Cell Accumulation in Fibrous Cap Lesions in Apolipoprotein E-Deficient Mice", Circulation, 103: 2955-2960, 2001.
Sato et al. "Tie-1 and Tie-2 Define Another Class of Putative Receptor Tyrosine Kinase Genes Expressed in Early Embryonic Vascular System", Proc. Natl. Acad. Sci. USA, 90: 9355-9358, 1993.
Savontaus et al. "Transcriptional Targeting of Conditionally Replicating Adenovirus to Dividing Endothelial Cells", Gene Therapy, XP002579436, 9(14): 972-979, Jul. 2002. Fig.1.
Schlaeger et al. "Vascular Endothelial Cell Lineage-Specific Promoter in Transgenic Mice", Development, 121: 1089-1098, 1995.
Shimo et al. "Connective Tissue Growth Factor as a Major Angiogenic Agent That Is Induced by Hypoxia in a Human Breast Cancer Cell Line", Cancer Letters, 174: 57-64, 2001.
Skolnick "From Genes to Protein Stucture and Function: Novel Applications of Computational Approaches in the Genomic Era", Trends in Biotechnology, TiBTech, 18: 34-39, Jan. 2000.
Smallwood et al. "Different Substitutions at Conserved Amino Acids in Domains II and III in the Sendai L RNA Polymerase Protein Inactive Viral RNA Synthesis", Virology, 304: 135-145, 2002.
Smythe et al. "Treatment of Experimental Human Mesothelioma Using Adenovirus Transfer of the Herpes Simplex Thymidine Kinase Gene", Annals of Surgery, 222(1): 78-86, 1995.
Soriano et al. "Targeted Disruption of the C-SRC Proto-Oncogene Leads to Osteopetrosis in Mice", Cell, 64: 693-702, 1991.
Staba et al. "Adenoviral TNF-Alpha Gene Therapy and Radiation Damage Tumor Vasculature in a Human Malignant Glioma Xenograft", Gene Therapy, 5: 293-300, 1998.
Stefanidakis et al. "Identification of a Negatively Charged Peptide Motif Within the Catalytic Domain of Progelatinases That Mediates Binding to Leukocyte ?2 Integrins", The Journal of Biological Chemistry, 278(36): 34674-34684, 2003.
Strasser et al. "Apoptosis Signaling", Annual Review of Biochemistry, XP002283497, 69: 217-245, 2000.
Sun et al. "Functional Analysis of the Preproendothelin-1 Gene Promoter in Pulmonary Epithelial Cells and Monocytes", Biochemical and Biophysical Research Communications, XP002305521, 221(3): 647-652, 1996. p. 649, last §-p. 651, § 1.
Takayama et al. "Vascular Endothelial Growth Factor Promoter-Based Conditionally Replicative Adenoviruses for Pan-Carcinoma Application", Cancer Gene Therapy, 14(1): 105-116, Jan. 31, 2007.
Thomas et al. "Progress and Problems With the Use of Viral Vectors for Gene Therapy", Nature Reviews: Genetics, 4: 346-358, May 2003.
Tomasinsig et al. "The Cathelicidins—Structure, Function and Evolution", Current Protein and Peptide Science, 6: 23-34, 2005.
Tomasoni et al. "Gene Therapy: How to Target the Kidney. Promises and Pitfalls", Current Gene Therapy, 4: 115-122, 2004.
Triozzi et al. "A Phase I Study to Assess the Safety and Distribution of GT-111 in Patients With Advanced Metastatic Cancer", Vascular Biogenics, Ltd., Clinical Trials Identifier: NCT00559117, Jun. 9, 2009.
Van de Stolpe et al. "Intercellular Adhesion Molecule-1", Journal of Molecular Medicine, 74(1): 13-33, 1996. Abstract.
Varda-Bloom et al. "Tissue-Specific Gene Therapy Directed to Tumor Angiogenesis", Gene Therapy, XP002349279, 8(11): 819-827, Jun. 2001. p. 822-825.
Verna et al. "Gene Therapy—Promises, Problems and Prospects", Nature, 389: 239-242, 1997.
Wachsberger et al. "Tumor Response to Ionizing Radiation Combines With Antiangiogenesis or Vascular Targeting Agents: Exploring Mechanisms of Interaction", Clinical Cancer Research, 9: 1957-1971, Jun. 1, 2003.
Wadhwa et al. "Cancer Gene Therapy: Scientific Basis", Annual Review of Medicine, XP002568022, 53: 437-453, 2002. p. 438.
Wang et al. "Molecular Cloning of the Complementary DNA for Human Tumor Necrosis Factor", Science, New Series, 228(4696): 149-154, 1985.
Watkins et al. "The 'Adenobody' Approach to Viral Targeting: Specific and Enhanced Adenoviral Gene Delivery", Gene Therapy, 4: 1004-1012, 1997.
Watson et al. "Structural Identification by Mass Spectrometry of Oxidized Phospholipids in Minimally Oxidized Low Density Lipoprotein That Induce Monocyte/Endothelial Interactions and Evidence for Their Presence in Vivo", Journal of Biological Chemistry, XP002904327, 272(21): 13597-13607, 1997. p. 13603.
West et al. "Endothelial Cell Proliferation and Diabetic Retinopathy", The Lancet, 1: 715-716, 1988.
Whitaker et al. "Induction of Functional Neovascularization by Wisker Stimulation After Focal Ischemia", Abstract Viewer and Itinery Planner, Society for Neuroscience, 2003: Abstract No. 789. 12, Nov. 2003. 33rd Annual Meeting of the Society of Neuroscience, New Orleans, LA, USA, Nov. 8-12, 2003.
Williams et al. "Hypoxia and Oxidative Stress in Breast Cancer Tumour Hypoxia—Therapeutic Considerations", Breast Cancer Research, 3: 328-331, 2001.
Wong et al. "Human GM-CSF: Molecular Cloning of the Complementary DNA and Purification of the Natural and Recombinant Proteins", Science, New Series, 228(4701): 810-815, 1985.

(56) References Cited

OTHER PUBLICATIONS

Wu et al. "Chimeric PSA Enhancers Exhibit Augmented Activity in Prostate Cancer Therapy Vectors", Gene Therapy, 8: 1416-1426, 2001.

Yanagisawa-Miwa et al. "Salvage of Infarcted Myocardium by Angiogenic Action of Basic Fibroblast Growth Factor", Science, New Series, 257(5075): 1401-1403, 1992.

Zou et al. "Antitumor Activity of Free and Liposome-Entrapped Annamycin, A Lipophilic Anthracycline Antibiotic With Non-Cross-Resistance Properties", Cancer Research, 54: 1479-1484, Mar. 15, 1994.

Adams, M. and Thomas, H., "A phase I study of the matrix metalloproteinase inhibitor, marimastat, administered concurrently with carboplatin, to patients with relapsed ovarian cancer," *Proceedings American Society of Clinical Oncology* 17:217a, American Society of Clinical Oncology, United States (1998).

Alon, T., et al., "Vascular endothelial growth factor acts as a survival factor for newly formed retinal vessels and has implications for retinopathy of prematurity," *Nature Medicine* 1(10):1024-1028, Nature Publishing Group, England (1995).

Alpern-Elran, H., et al., "Angiogenic activity of the atherosclerotic carotid artery plaque," *J. Neurosurg.* 70:942-945, American Association of Neurological Surgeons, United States (1989).

Bangari, D.S. and Mittal, S.K., "Current Strategies and Future Directions for Eluding Adenoviral Vector Immunity," *Current Gene Therapy* 6(2):215-226, Bentham Science, United States (2006).

Becker, T. C., et al., "Use of Recombinant Adenovirus for Metabolic Engineering of Mammalian Cells," *Methods in Cell Biology* 43:161-189, Academic Press, Inc., United States (1994).

Benjamin, L.E. and Keshet, E., "Conditional switching of vascular endothelial growth factor (VEGF) expression in tumors: Induction of endothelial cell shedding and regression of hemangioblastoma-like vessels by VEGF withdrawal," *Proc. Natl. Acad. Sci. USA* 94:8761-8766, The National Academy of Sciences, United States (1997).

Benjamin, L.E., et al., "Selective ablation of immature blood vessels in established human tumors follows vascular endothelial growth factor withdrawal," *J. Clin. Invest.* 103(2):159-165, American Society for Clinical Investigation, United States (1999).

Brenner, et al., "Antivascular Activity of VBIII in Glioblastoma Xenografts," *Journal of Clinical Oncology*, ASCO Annual Meeting Proceedings (Post Meeting Edition), 28(15 Suppl.): Abstract No. e13652, American Society of Clinical Oncology, United States (2010).

Calabresi, P. and Chabner, B.A. "Antineoplastic Agents" *The Pharmacological Basis of Therapeutics* 52:1209-1263, 8th Edition, Pergamon Press, Inc., United States (1990).

Celletti, F.L., et al., "Effect of Human Recombinant Vascular Endothelial Growth Factor$_{165}$ on Progression of Atherosclerotic Plaque," *Journal of the American College of Cardiology* 37(8):2126-2130, American College of Cardiology, Elsevier Science, Inc., United States (2001).

Chi, A.S., et al., "Angiogenesis as a Therapeutic Target in Malignant Gliomas," *The Oncologist* 14(6):621-636, AlphaMed Press, AlphaMed Press, United States (2009).

Couffinhal, T. et al., "Animal Model: Mouse Model of Angiogenesis," *American Journal of Pathology* 152(6):1667-1679, American Society for Investigative Pathology, United States (1998).

Denekamp, J. and Hobson, B., "Endothelial-Cell Proliferation in Experimental Tumours," *Br. J Cancer* 46:711-720, Nature Publishing Group, England (1982).

De Palma, M., et al., "Targeting exogenous genes to tumor angiogenesis by transplantation of genetically modified hematopoietic stem cells," *Nature Medicine* 9(6):789-795, Nature Publishing Group, England (2003).

Dulak, J., et al., "Vascular Endothelial Growth Factor: Angiogenesis, Atherogenesis or Both?," *Journal of the American College of Cardiology* 38(7):2137-2138, Elsevier Biomedical, United States (2001).

Fang, B. and Roth, J.A., "The role of gene therapy in combined modality treatment strategies for cancer," *Current Opinion in Molecular Therapeutics* 5(5):475-482, Current Drugs, England (2003).

Fiers, W., et al., "The Human Fibroblast and Human Immune Interferon Genes and Their Expression in Homologous and Heterologous Cells," *Phil. Trans. R. Soc. Lond. B.* 299(1094):29-38, The Royal Society, England (1982).

Folkman, J., "Role of angiogenesis in tumor growth and metastasis," *Semin Oncol* 29(6):15-18, Elsevier Science, USA (2002).

Folkman, J., "Seminars in Medicine of the Beth Israel Hospital, Boston: Clinical Applications of Research on Angiogenesis," *The New England Journal of Medicine* 333(26):1757-1763, Massachusetts Medical Society, United States (1995).

Folkman, J., "Toward an understanding of angiogenesis: search and discovery," *Perspectives in Biology and Medicine* 29:10-36, The University of Chicago Press, United States (1985).

Funatsu, H., et al., "Increased Levels of Vascular Endothelial Growth Factor and Interleukin-6 in the Aqueous Humor of Diabetics with Macular Edema," *Am. J. Opthalmol.* 133(1):70-77, Elsevier Science Inc., United States (2002).

Gilboa, E., et al., "Transfer and expression of cloned genes using retroviral vectors," *BioTechniques* 4(6):504-512, Eaton Publishing Co., United States (1986).

Goltsev, Y. V., et al., "CASH, A Novel Caspase Homologue With Death Effector Domains," *The Journal of Biological Chemistry* 272(32):19641-19644, The American Society for Biochemistry and Molecular Biology, United States (1997).

Gowdak, L.H.W., et al., "Adenovirus-Mediated VEGF$_{121}$ Gene Transfer Stimulates Angiogenesis in Normoperfused Skeletal Muscle and Preserves Tissue Perfusion After Induction of Ischemia," *Circulation* 102:565-571, American Heart Association, United States (2000).

Hahn, A.W.A., et al., "Effects of Peptide Vasoconstrictors on Vessel Structure," *The American Journal of Medicine* 94(4A):13S-19S, Association of Professors of Medicine, United States (1993).

Hammond, H.K. and McKirnan, M.D., "Angiogenic gene therapy for heart disease: a review of animal studies and clinical trials," *Cardiovascular Research* 49:561-567, Elsevier Science B.V., Netherlands (2001).

Hanahan, D., "Signaling Vascular Morphogenesis and Maintenance," *Science* 277:48-50, American Association for the Advancement of Science, United States (1997).

Harrigan, M.R., et al., "Intraventricular Infusion of Vascular Endothelial Growth Factor Promotes Cerebral Angiogenesis with Minimal Brain Edema," *Neurosurgery* 50(3):589-598, Lippincott Williams & Wilkins, United States (2002).

Herbst, R.S., et al., "Angiogenesis Inhibitors in Clinical Development for Lung Cancer," *Seminars in Oncology* 29(1):66-77, Elsevier Science, United States (2002).

Morimoto, E., et al. "Adenovirus-mediated suicide gene transfer to small cell lung carcinoma using a tumor-specific promoter," *Anticancer Research* 21:329-331, International Institute of Anticancer Research, Greece (2001).

Murata, T., et al., "Vascular Endothelium Has a Local Anti-Adenovirus Vector System and Glucocorticoid Optimizes Its Gene Transduction," *Arterioscler Thromb. Vasc. Biol.* 25:1796-1803, American Heart Association, Inc., United States (2005).

Nayak, S., et al., "Progress and Prospects: Immune Responses to Viral Vectors," *Gene Therapy* 17(3):295-304, Advance Online Publication, Nature Publishing Group, England (2009).

NCBI Entrez, GenBank Report, Accession No. AR005095, Harats, D., et al., Entry Date Dec. 1998.

Nesbit, M., et al., "α5 and α2 Integrin Gene Transfers Mimic the PDGF-B—Induced Transformed Phenotype of Fibroblasts in Human Skin," *Laboratory Investigation* 81(9):1263-1274, The United States and Canadian Academy of Pathology, Inc., United States (2001).

Nettelbeck, D.M., et al., "Targeting of Adenovirus to Endothelial Cells by a Bispecific Single-Chain Diabody Directed against the Adenovirus Fiber Knob Domain and Human Endoglin (CD105)," *Moleculer Therapy* 3(6):882-891, The American Society of Gene Therapy, United States (2001).

(56) References Cited

OTHER PUBLICATIONS

Nicosia, R. and Ottinetti, A., "Growth of Microvessels in Serum-Free Matrix Culture of Rat Aorta: A Quantitative Assay of Angiogenesis In vitro," *Laboratory Investigation* 63(1):115-122, The United States and Canadian Academy of Pathology, Inc., United States (1990).

Nicosia, R. F., et. al., "Modulation of Angiogenesis in Vitro by Laminin-Entactin Complex," *Developmental Biology* 164:197-206, Academic Press, Inc., United States (1994).

Ozaki, K., et al., "Use of von Willebrand Factor Promoter to Transduce Suicidal Gene To Human Endothelial Cells, HUVEC," *Human Gene. Therapy* 7:1483-1490, Mary Ann Liebert, Inc., United States (1996).

Paku, S. and Paweletz, N., "First Steps of Tumor-Related Angiogenesis," *Laboratory Investigation* 65(3):334-346, The United States and Canadian Academy of Pathology, Inc., United States (1991).

Horley, K. J., et al., "Molecular cloning of murine intercellular adhesion molecule (ICAM-1)," *EMBO. J.* 8(10):2889-2896, IRL Press, USA (1989).

Hsu, S., et al., "Platelet-Derived Growth Factor-B Increases Colon Cancer Cell Growth In Vivo by a Paracrine Effect," *Journal of Cellular Physiology* 165:239-245, Wiley-Liss, Inc., United States (1995).

Iademarco, M.F., et al., "Characterization of the promoter for vascular cell adhesion molecule-1 (VCAM-1)," *The Journal of Biological Chemistry* 267(23):16323-16329, The American Society for Biochemistry and Molecular Biology, Inc. (1992).

Itasaka, S., et al., "Endostatin Blocks Endothelial Repopulation After Radiation Therapy," *Proceedings of the American Association for Cancer Research* 44(2):22, American Association for Cancer Research, United States (2003).

Jaggar, R.T., et al., "Endothelial Cell-Specific Expression of Tumor Necrosis Factor-α from the KDR or E-Selectin Promoters Following Retroviral Delivery," *Human Gene Therapy* 8:2239-2247, Mary Ann Liebert, Inc., United States (1997).

Katabi, M. M., et al., "Hexokinase Type II: A Novel Tumor-Specific Promoter for Gene-Targeted Therapy Differentially Expressed and Regulated in Human Cancer Cells," *Human Gene Therapy* 10:155-164, Mary Ann Liebert, Inc., United States (1999).

Kim, P. K. M., et al., "Hepatocyte Fas-associating Death Domain Protein/Mediator of Receptor-induced Toxicity (FADD/MORT1) Levels Increase in Response To Pro-apoptotic Stimuli," *The Journal of Biological Chemistry* 277(41):38855-38862, The American Society for Biochemistry and Molecular Biology, Inc., United States (2002).

Kim, W. J., et al., "Effect of PDGF, IL-1α, and BMP2/4 on Corneal Fibroblast Chemotaxis: Expression of the Platelet-Derived Growth Factor System in the Cornea," *Investigative Ophthalmology & Vision Science* 40(7):1364-1372, Association for Research in Vision and Ophthalmology, Association for Research in Vision and Ophthalmology, United States (1999).

Kwong, Y.-L., et al., "Combination Therapy with Suicide and Cytokine Genes for Hepatic Metastases of Lung Cancer," *CHEST* 112(5):1332-1337, The American College of Chest Physicians, United States (1997).

Mariani, et al., "Anti-angiogenesis: the challenges ahead," *MedGenMed* 5(2):22, MedScape, United States (2003).

Peled, M., et al., "Antiangiogenic systemic gene therapy combined with doxorubicin administration induced caspase 8 and 9-mediated apoptosis in endothelial cells and an anti-metastasis effect," *Cancer Gene Therapy* 15:535-542, Nature Publishing Group, England (2008).

Printz, M. A., et al., "Fibroblast Growth Factor 2-Retargeted Adenoviral Vectors Exhibit a Modified Biolocalization Pattern and Display Reduced Toxicity Relative to Native Adenoviral Vectors," *Human Gene Therapy* 11:191-204, Mary Ann Liebert, Inc , United States (2000).

Roberts, D.M. et al., "Hexon-chimaeric adenovirus serotype 5 vectors circumvent pre-existing anti-vector immunity," *Nature* 441:239-243, Nature Publishing Group, England (2006).

Ronicke, V., et al., "Characterization of the endothelium-specific murine vascular endothelial growth factor receptor-2 (Flk-1) promoter," *Circulation Research* (2):277-285, American Heart Association, Inc,, United States (1996).

Rosengart, T.K. et al., "Six-month assessment of a phase I trial of angiogenic gene therapy for the treatment of coronary artery disease using direct intramyocardial administration of an adenovirus vector expressing the VEGF121 cDNA," *Annals of Surgery* 230(4):466-472, Lippincott Williams & Wilkins, Inc., United States (1999).

Roskoski, Jr., R., "Sunitinib: A VEGF and PDGF receptor protein kinase and angiogenesis inhibitor," *Biochemical and Biophysical Research Communications* 356:323-328, Elsevier Inc., United States (2007).

Schlaeger, T.M., et al., "Uniform vascular-endothelial-cell-specific gene expression in both embryonic and adult transgenic mice," *Proc. Natl. Acad. Sci. USA* 94:3058-3063, The National Academy of Sciences of the USA, United States (1997).

Schramek, H., et al., "Interactions of the vasoconstrictor peptides, angiotensin II and endothelin-I, with vasodilatory prostaglandins," *Seminars in Nephrology* 15(3):195-204, W.B. Saunders Company, United States (1995).

Semenza, G.L., et al., "Hypoxia, HIF-1, and the pathophysiology of the common human diseases," *Adv. Exp. Med. Biol.* 475:123-130, Kluwer Academic/Plenum Publishers, United States (2000).

Shir, A. and Levitzki, A., "Gene Therapy for Glioblastoma: Future Perspective for Delivery Systems and Molecular Targets," *Cellular and Molecular Neurobiology* 21(6):645-656, Plenum Publishing Corporation, USA (2001).

Simovic, D., et al., "Improvement in Chronic Ischemic Neuropathy After Intramuscular phVEGF$_{165}$ Gene Transfer in Patients with Critical Limb Ischemia," *Arch. Neurol.* 58:761-768, American Medical Association, United States (2001).

Sukhatme, V.P., et al:, "A Novel Early Growth Response Gene Rapidly Induced by Fibroblast, Epithelial Cell and Lymphocyte Mitogens," *Oncogene Research* 1:343-355, Harwood Academic Publishers GmbH, Switzerland (1987).

Theodosis, D. T., "Oxytocin-Secreting Neurons: A Physiological Model of Morphological Neuronal and Glial Plasticity in the Adult Hypothalamus," *Frontiers in Neuroendocrinology* 23:101-135, Elsevier Science, United States (2002).

Thickett, D.R., "Vascular Endothelial Growth Factor May Contribute to Increased Vascular Permeability in Acute Respiratory Distress Syndrome," *Am. J. Respir. Crit. Care Med.* 164:1601-1605, American Thoracic Society, United States (2001).

Thompson, J. A., et al., "Heparin-binding growth factor 1 induces the formation of organoid neovascular structures in vivo," *Proc. Natl. Acad. Sci. USA* 86:7928-7932, The National Academy of Sciences, United States (1989).

Unger, E.F., et al., "Basic fibroblast growth factor enhances myocardial collateral flow in a canine model," *American Journal of Physiology* 266(4):H1588-H1595, The American Physiological Society, United States (1994).

Yanagisawa, M., et al., "A novel potent vasoconstrictor peptide produced by vascular endothelial cells," *Nature* 332:411-415, Nature Publishing Group, England (1988).

Yang, M., et al., "Whole-body and intravital optical imaging of angiogenesis in orthotopically implanted tumors," *PNAS* 98(5):2616-2621, The National Academy of Sciences, United States (2001).

Young, D., "VBL Focuses on Inflammatory Market With Novel Phospholipids," *BioWorld Today* 21(3):1-7, AHC Media LLC, United States (2010).

Zhang, Z.-L., et al., "Current Strategies and Future Directions of Antiangiogenic Tumor Therapy" *Acta Biochimica et Biophysica Sinica* 35(10):873-880, China Academic Journal Electronic Publishing House, China (2003).

International Search Report and the Written Opinion for INternational Application No. PCT/IL2011/00009, Patent Cooperation Treaty, mailed on May 20, 2011.

International Search Report and the Written Opinion International Application No. PCT/IL2011/00007, Patent Cooperation Treaty, mailed on Sep. 1, 2011.

Office Action mailed Dec. 17, 2012, in U.S. Appl. No. 13/549,355, Dror Harats et al., filed Jul. 13, 2012.

(56) References Cited

OTHER PUBLICATIONS

Office Action mailed Jan. 2, 2013, in U.S. Appl. No. 12/224,178, Dror Harats et al., filed Aug. 20, 2008.
Notice of Allowance mailed Apr. 8, 2009, in U.S. Appl. No. 10/975,619, Dror Harats et al., filed Oct. 29, 2004.
English language Abstract of Japanese Patent Publication No. JP 2003-501367 A, European Patent Office, espacenet database—Worldwide (2003).
Tanaka, T. et al., "Viral Vector-targeted Antiangiogenic Gene Therapy Utilizing an Angiostatin Complementary DNA," *Cancer Research* 58:3362-3369, American Association for Cancer Research, United States (1998).
Office Action mailed Jun. 13, 2013, in U.S. Appl. No. 12/457,200, Dror Harats et al., filed Jun. 3, 2009.
Office Action mailed Jun. 17, 2013, in U.S. Appl. No. 13/094,900, Dror Harats et al., filed Apr. 27, 2011.
Office Action mailed on Aug. 8, 2013, in U.S. Appl. No. 12/591,252, Eyal Breitbart et al., filed Nov. 13, 2009.
Office Action mailed on May 16, 2013, in U.S. Appl. No. 13/549,355, Dror Harats et al., filed Jul. 13, 2012.
Office Action mailed on Jun. 20, 2013, U.S. Appl. No. 11/790,992, Dror Harats et al., filed Apr. 30, 2007.
Restriction Requirement mailed Sep. 18, 2013, in U.S. Appl. No. 13/800,478, Dror Harats et al., filed Mar. 13, 2013.
Restriction Requirement mailed on Nov. 6, 2013, in U.S. Appl. No. 13/785,863, Dror Harats et al., filed Mar. 5, 2013.
Office Action mailed on Oct. 22, 2013, in U.S. Appl. No. 13/549,355, Dror Harats et al., filed Jul. 13, 2012.
Supplementary European Seasrch Report and European Search Opinion for European Application No. 07713267.8, European Patent Office, Munich, Germany, mailed on Aug. 23, 2013.
Office Action mailed on Nov. 18, 2013, in U.S. Appl. No. 12/457,200, Dror Harats et al., filed Jun. 3, 2009.
Office Action mailed on Dec. 27, 2013, in U.S. Appl. No. 13/800,478, Dror Harats et al., filed Mar. 13, 2013.
Office Action mailed on Jan. 3, 2014, in U.S. Appl. No. 12/591,252, Dror Harats et al., filed Nov. 13, 2009.
Co-pending Application, U.S. Appl. No. 13/520,457 inventors Harats, D., et al., filed on Jul. 3, 2012 (Not Published).
Co-pending Application, U.S. Appl. No. 14/059,426 inventors Harats, D., et al., filed on Oct. 21, 2013 (Not Published).
Office Action mailed on Feb. 27, 2014, in U.S. Appl. No. 13/785,863, Dror Harats et al., filed Mar. 5, 2013.
Lopez, C.A., et al., "Chemoinducible gene therapy: A strategy to enhance doxorubicin antitumor activity," *Molecular Cancer Therapeutics* 3(9):1167-1175, American Association for Cancer Research, United States (2004).
Li, Y. et al., "A Hepatocellular Carcinoma-specific Adenovirus Variant, CV890, Eliminates Distant Human Liver Tumors in Combination with Doxorubicin," *Cancer Research* 61:6428-6436, American Association for Cancer Research, United States (2001).
SCORE Search Results Details for U.S. Appl. No. 12/224,178, received in the Office Action dated Jan. 2, 2013, for U.S. Appl. No. 12/224,178, filed Aug. 20, 2008, pp. 26-27 of 617 and pp. 90-91 of 609.
Sebastian, M., et al., "Adenovirus-mediated interferon-β gene therapy combined with radiotherapy synergistically inhibits lung tumor growth in mice," *Journal of Clinical Oncology* 22:7340, American Society of Clinical Oncology, United States (2004).
Zhu, Z.B. et al., "Targeting lung cancer using an infectivity enhanced CXCR4-CRAd," *Lung Cancer* 55:145-156, Elsevier Ireland Ltd., Ireland (2007).
Office Action mailed on Jun. 6, 2014, in U.S. Appl. No. 12/591,252, Eyal Breitbart et al., filed Nov. 13, 2009.

SEQUENCE LISTING

<160> NUMBER OF SEQ ID NOS: 8

<210> SEQ ID NO 1
<211> LENGTH: 1334
<212> TYPE: DNA
<213> ORGANISM: Mus musculus

<400> SEQUENCE: 1

| | | | | | |
|---|---|---|---|---|---|
| gtgtgtgtgt | gtgtgtgtgt | gtgtgtgtgt | gtgtgtgtgt | gtgtagtgta | cttctgatcg | 60 |
| gcgatactag | ggagataagg | atgtacctga | caaaaccaca | ttgttgttgt | tatcattatt | 120 |
| atttagtttt | ccttccttgc | taactcctga | cggaatcttt | ctcacctcaa | atgcgaagta | 180 |
| ctttagttta | gaaaagactt | ggtggaaggg | gtggtggtgg | aaaagtaggg | tgatcttcca | 240 |
| aactaatctg | gttccccgcc | cgccccagta | gctgggattc | aagagcgaag | agtggggatc | 300 |
| gtccccttgt | ttgatcagaa | agacataaaa | ggaaaatcaa | gtgaacaatg | atcagcccca | 360 |
| cctccaccec | accccctgc | gcgcgcacaa | tacaatctat | ttaattgtac | ttcatacttt | 420 |
| tcattccaat | ggggtgactt | tgcttctgga | gaaactcttg | attcttgaac | tctggggctg | 480 |
| gcagctagca | aaaggggaag | cgggctgctg | ctctctgcag | gttctgcagc | ggtctctgtc | 540 |
| tagtgggtgt | tttcttttc | ttagccctgc | ccctggattg | tcagacggcg | ggcgtctgcc | 600 |
| tctgaagtta | gccgtgattt | cctctagagc | cgggtcttat | ctctggctgc | acgttgcctg | 660 |
| tgggtgacta | atcacacaat | aacattgttt | agggctggaa | taaagtcaga | gctgtttacc | 720 |
| cccactctat | aggggttcaa | tataaaaagg | cggcggagaa | ctgtccgagt | cagacgcgtt | 780 |
| cctgcaccgg | cgctgagagc | ctgacccggt | ctgctccgct | gtccttgcgc | gctgcctccc | 840 |
| ggctgcccgc | gacgctttcg | ccccagtgga | agggccactt | gctgaggacc | gcgctgagat | 900 |
| ctaaaaaaa | aacaaaaaac | aaaaaacaaa | aaacccaga | ggcgatcaga | gcgaccagac | 960 |
| accgtcctct | tcgttttgca | ttgagttcca | tttgcaaccg | agttttcttt | ttttcctttt | 1020 |
| tccccactct | tctgaccct | ttgcagaatg | gattattttc | ccgtgatctt | ctctctgctg | 1080 |
| ttcgtgactt | tccaaggagc | tccagaaaca | ggtaggcgcc | acttgcgaat | ctttctactt | 1140 |
| cagcgcagca | gttatcgctt | ctgttttcca | cttttctttc | tttcttttct | ttcattcttt | 1200 |
| ccttttatt | tattttttta | attactgaag | ctccagcagc | aagtgcctta | caattaatta | 1260 |
| acttctgtgt | gaagcgaaag | aaataaaaacc | cctgtttgaa | tacagctgac | tacaaccgag | 1320 |
| tatcgcatag | cttc | | | | | 1334 |

<210> SEQ ID NO 2
<211> LENGTH: 96
<212> TYPE: DNA
<213> ORGANISM: Artificial sequence
<220> FEATURE:
<223> OTHER INFORMATION: Synthetic oligonucleotide

<400> SEQUENCE: 2

| | | | | | |
|---|---|---|---|---|---|
| gctagcgtac | ttcatacttt | tcattccaat | ggggtgactt | tgcttctgga | gggtgactt | 60 |
| gcttctggag | ccaatgggta | cttcatactt | ttcatt | | | 96 |

<210> SEQ ID NO 3
<211> LENGTH: 96
<212> TYPE: DNA
<213> ORGANISM: Artificial sequence
<220> FEATURE:
<223> OTHER INFORMATION: Synthetic oligonucleotide -continued

<400> SEQUENCE: 3
gctagcctcc agaagcaaag tcaccccatt ggaatgaaaa gtatgaagta caatgaaaag    60
tatgaagtac ccattggctc cagaagcaaa gtcacc    96

<210> SEQ ID NO 4
<211> LENGTH: 6
<212> TYPE: DNA
<213> ORGANISM: Artificial sequence
<220> FEATURE:
<223> OTHER INFORMATION: Nhe-1 restriction site

<400> SEQUENCE: 4 gctagc    6

<210> SEQ ID NO 5
<211> LENGTH: 6
<212> TYPE: DNA
<213> ORGANISM: Mus musculus
<220> FEATURE:
<221> NAME/KEY: misc_feature
<223> OTHER INFORMATION: Hypoxia responsive element - E-box

<400> SEQUENCE: 5 gcacgt    6

<210> SEQ ID NO 6
<211> LENGTH: 44
<212> TYPE: DNA
<213> ORGANISM: Mus musculus
<220> FEATURE:
<221> NAME/KEY: misc_feature
<223> OTHER INFORMATION: Murine endothelial specific enhancer element

<400> SEQUENCE: 6
gtacttcata cttttcattc caatggggtg actttgcttc tgga    44

<210> SEQ ID NO 7
<211> LENGTH: 143
<212> TYPE: DNA
<213> ORGANISM: Artificial sequence
<220> FEATURE:
<223> OTHER INFORMATION: A triplicate copy of a murine enhancer sequence
      originated from the PPE-1 promoter

<400> SEQUENCE: 7
gtacttcata cttttcattc caatggggtg actttgcttc tggagggtga ctttgcttct    60
ggagccagta cttcatactt ttcattgtac ttcatacttt tcattccaat ggggtgactt    120
tgcttctgga ggctagctgc cag    143

<210> SEQ ID NO 8
<211> LENGTH: 47
<212> TYPE: DNA
<213> ORGANISM: Artificial sequence
<220> FEATURE:
<223> OTHER INFORMATION: EDC fragment

<400> SEQUENCE: 8
ctggagggtg actttgcttc tggagccagt acttcatact tttcatt    47

PROMOTERS EXHIBITING ENDOTHELIAL CELL SPECIFICITY AND METHODS OF USING SAME

RELATED APPLICATIONS

This application is a divisional of U.S. patent application Ser. No. 13/094,900 filed on Apr. 27, 2011, which is a divisional of pending U.S. patent application Ser. No. 12/457,200 filed on Jun. 3, 2009, which is a divisional of U.S. patent application Ser. No. 10/975,619 filed on Oct. 29, 2004, now U.S. Pat. No. 7,579,327, which is a divisional of U.S. patent application Ser. No. 10/135,447 filed on May 1, 2002, now U.S. Pat. No. 7,067,649, which is a continuation-in-part (CIP) of PCT Patent Application No. PCT/IL01/01059 filed on Nov. 15, 2001, which claims the benefit of priority of U.S. Provisional Patent Application No. 60/248,582 filed on Nov. 17, 2000. The contents of all of the above applications are incorporated by reference as if fully set forth herein.

REFERENCE TO SEQUENCE LISTING SUBMITTED ELECTRONICALLY VIA EFS-WEB

This application includes a "3182_0350004_SequenceListing_ascii.txt" 3,983bytes, created, on Feb. 22, 2013, and submitted electronically via EFS-Web, which is hereby, incorporated by reference in its entirety.

FIELD AND BACKGROUND OF THE INVENTION

The present invention relates to isolated polynucleotide sequences exhibiting endothelial cell specific promoter activity, and methods of use thereof and, more particularly, to a modified-preproendothelin-1 (PPE-1) promoter which exhibits increased activity and specificity in endothelial cells. The invention further relates to modifications of the PPE promoter, which enhance its expression in response to physiological conditions including hypoxia and angiogenesis.

Angiogenesis, the process of formation of new blood vessels, plays an important role in physiological processes such as embryonic and postnatal development as well as in wound repair. Formation of blood vessels can also be induced by pathological processes involving inflammation (e.g., diabetic retinopathy and arthritis) or neoplasia (e.g., cancer) (Folkman, 1985, Perspect, Biol. Med., 29, 10).

Angiogenesis occurs under conditions of low oxygen concentration (ischemia and tumor metastases etc.) and thus may be an important environmental factor in neovascularization. The expression of several genes including erythropoietin, transferrin and its receptor, most of glucose transport and glycolytic pathway genes, LDH, PDGF-BB, endothelin-1 (ET-1), VEGF and VEGF receptors is induced under hypoxic conditions by the specific binding of the Hypoxia Inducible Factor (HIF-1) to the Hypoxic Response Element (HRE) regulating the transcription of these genes. Expression of these genes in response to hypoxic conditions enables the cell to function under low oxygen conditions.

The angiogenic process is regulated by angiogenic growth factors secreted by tumor or normal cells as well as the composition of the extracellular matrix and by the activity of endothelial enzymes (Nicosia and Ottinetti, 1990, Lab. Invest., 63, 115). During the initial stages of angiogenesis, endothelial cell sprouts appear through gaps in the basement membrane of pre-existing blood vessels (Nicosia and Ottinetti, 1990, supra; Schoefl, 1963, Virehous Arch, Pathol. Anat. 337, 97-141; Ausprunk and Folkman, 1977, Microvasc. Res. 14, 53-65; Paku and Paweletz, 1991, Lab. Invest. 63, 334-346). As new vessels form, their basement membrane undergoes complex structural and compositional changes that are believed to affect the angiogenic response (Nicosia, et. al., 1994, Exp Biology. 164, 197-206).

Unbalanced angiogenesis typifies various pathological conditions and often sustains progression of the pathological state. For example, in solid tumors, vascular endothelial cells divide about 35 times more rapidly than those in normal tissues (Denekamp and Hobson, 1982 Br. J. Cancer 46:711-20). Such abnormal proliferation is necessary for tumor growth and metastasis (Folkman, 1986 Cancer Res. 46:467-73).

Vascular endothelial cell proliferation is also important in chronic inflammatory diseases such as rheumatoid arthritis, psoriasis and synovitis, where these cells proliferate in response to growth factors released within the inflammatory site (Brown & Weiss, 1988, Ann. Rheum. Dis. 47:881-5).

In atherosclerosis, formation of an atherosclerotic plaque is triggered by a monoclonal expansion of endothelial cells in blood vessels (Alpern-Elran 1989, J. Neurosurg. 70:942-5). Furthermore, in diabetic retinopathy, blindness is thought to be caused by basement membrane changes in the eye, which stimulate uncontrolled angiogenesis and consumption of the retina (West and Kumar, 1988, Lancet 1:715-6).

Endothelial cells are also involved in graft rejection. In allograft rejection episodes, endothelial cells express pro-adhesive determinants that direct leukocyte traffic to the site of the graft. It is believed that the induction of leukocyte adhesion molecules on the endothelial cells in the graft may be induced by locally-released cytokines, as is known to occur in an inflammatory lesion.

Abrogated angiogenesis, on the other hand, is also a major factor in disease development, such as in atherosclerosis induced coronary artery blockage (e.g., angina pectoris), in necrotic damage following accidental injury or surgery, or in gastrointestinal lesions such as ulcers.

Hence, regulating or modifying the angiogenic process can have an important therapeutic role in limiting the contributions of this process to pathological progression of an underlying disease state as well as providing a valuable means of studying their etiology.

Recently a significant progress in the development of endothelial regulating agents, whether designed to be inhibitory or stimulatory, has been made. For example, administration of aFGF protein, within a collagen-coated matrix, placed in the peritoneal cavity of adult rats, resulted in a well vascularized and normally perfused structure (Thompson, et al., PNAS 86:7928-7932, 1989). Injection of βFGF protein into adult canine coronary arteries during coronary occlusion reportedly led to decreased myocardial dysfunction, smaller myocardial infarctions, and increased vascularity (Yanagisawa-Miwa, et al., Science 257:1401-1403, 1992). Similar results have been reported in animal models of myocardial ischemia using βFGF protein (Harada, et al., J Clin Invest 94:623-630, 1994, Unger, et al., Am J Physiol 266:H1588-H1595, 1994).

However, for mass formation of long lasting functional blood vessel there is a need for repeated or long term delivery of the above described protein factors, thus limiting their use in clinical settings. Furthermore, in addition to the high costs associated with the production of angiogenesis-regulating factors, efficient delivery of these factors requires the use of catheters to be placed in the coronary arteries, which further increases the expense and difficulty of treatment.

With the identification of new genes that regulate the angiogenic process, somatic gene therapy has been attempted to overcome these limitations. Although, great efforts have been directed towards developing methods for gene therapy of cancer, cardiovascular and peripheral vascular diseases, there is still major obstacles to effective and specific gene delivery. In general, the main limiting factor of gene therapy with a gene of interest using a recombinant viral vector as a shuttle is the ability to specifically direct the gene of interest to the target tissue. Indeed, non-specific gene targeting, results in systemic expression of the transgene which leads to several problems. For example, systemic expression of VEGF, a key regulator of the angiogenic process has been tested in animal models of ischemia and in clinical trials [Hammond, H. K. and McKirnan, M. D. Cardiovasc Res 49, 561-7. (2001); Gowdak, L. H. et al. Circulation 102, 565-71. (2000); Rosengart, T. K. et al. Ann. Surg. 230, 466-70; discussion 470-2. (1999). Simovic, D et al. Arch Neurol 58, 761-8. (2001)]. However, due to the systemic nature of expression, all modalities of treatment faced the problems of facilitated atherogenesis [Dulak J. (2001) J Am Coll Cardiol 38:2137-8 and Celletti F L et al. (2001) J Am Coll Cardiol 2126-30] and edema [Harrigan M R et al. (2002) Neurosurgery 50:589-598; Funatsu H et al. (2002) Am J Opthalmol 133:70-7; Thicket D R (2001) Am J Respir Crit. Care Med 164:1601-5], vessel immaturity, hyper permeability and regression [Benjamin, L. E et al (1999) J Clin Invest 103:159-65; Alon, T et al. Nat Med 1:1024-8. (1995); Benjamin, L. E. et al. (1997) Proc Natl Acad Sci USA 94:8761-6].

Hence, regulation of the angiogenic process by targeted gene therapy to the vascular endothelium can be tremendously important in inducing efficient therapy for these diseases.

Several endothelial cell specific promoters have been described in the prior art. For example, Aird et al., [Proc. Natl. Acad. Sci. (1995) 92:7567-571] isolated 5' and 3' regulatory sequences of human von Willebrand factor gene that may confer tissue specific expression in-vivo. However, these sequences could mediate only a heterogeneous pattern of reporter transgene expression. Bacterial LacZ reporter gene placed under the regulation of von Willebrand regulatory elements in transgenic mice revealed transgene expression in a subpopulation of endothelial cells in the yolk sac and adult brain. However, no expression was detected in the vascular beds of the spleen, lung, liver, kidney, heart, testes and aorta as well as in the thrombomodulin locus.

Korhonen J et al [Blood (1995) 96:1828-35] isolated the human and mouse TIE gene promoter which contributed to a homogeneous expression of a transgene throughout the vascular system of mouse embryos. However, expression in adult was limited to the vessels of the lung and kidney and no expression was detected in the heart, brain, liver. Similar results were obtained by Schlaeger M et al. who isolated a 1.2 kb 5' flanking region of the TIE-2 promoter, and showed transgene expression limited to endothelial cells of embryonic mice [Schlaeger T M et al. (1995) Development 121: 1089-1098].

Thus, none of these sequences work uniformly in all endothelial cells of all developmental stages or in the adult animal. Furthermore, some of these sequences were not restricted to the endothelium.

U.S. Pat. No. 5,747,340 teaches use of the murine PPE-1 promoter and portions thereof. However, this patent contains no hint or suggestion that an endothelial-specific enhancer can be employed to increase the level of expression achieved with the PPE promoter while preserving endothelial specificity. Further, this patent does not teach that the PPE-1 promoter is induced to higher levels of transcription under hypoxic conditions.

An autonomous endothelial-specific enhancer in the first intron of the mouse TIE-2 gene was recently described. Combination of the TIE-2 promoter with an intron fragment containing this enhancer allowed it to target reporter gene expression specifically and uniformly to all vascular endothelial cells throughout embryogenesis and adulthood [Schlaeger T M (1997) Proc. Natl. Acad. Sci. 94:3058-3063]. Though, promising until today no expression of angiogenic transgenes have been described in conjugation with this regulatory element.

While reducing the present invention to practice, the present inventors have constructed and employed a novel configuration of the PPE-1 promoter which exhibits unexpected and highly specific activity in endothelial cells participating in angiogenesis.

Due to its capability to direct high expression of exogenous genes in an endothelial cell specific manner, the PPE-1 promoter of the present invention, which is designated as PPE-1-3X herein, enables regulating endothelial-specific processes. Thus, angiogenesis-regulating factors placed under the modified promoters of the present invention can serve as powerful in-vivo pro-angiogenic or anti-angiogenic tools in basic research and in clinical applications, such as of the cardiovascular system.

SUMMARY OF THE INVENTION

According to one aspect of the present invention there is provided an isolated polynucleotide functional as a promoter in eukaryotic cells. The isolated polynucleotide includes an enhancer element including at least two copies of the sequence set forth in SEQ ID NO:6.

According to another aspect of the present invention there is provided a method of expressing a nucleic acid sequence of interest, encoding an active RNA molecule or a protein such as an enzyme, reporter molecule and the like in endothelial cells. The method includes administering to a subject a construct, which includes the nucleic acid sequence of interest positioned under the regulatory control of a promoter functional in eukaryotic cells. The construct further includes an enhancer element including at least one copy of the sequence set forth in SEQ ID NO:6.

According to yet another aspect of the present invention there is provided a method of regulating angiogenesis in a tissue. The method includes administering a nucleic acid construct including: (a) an endothelial cell specific promoter; (b) at least one copy of a hypoxia response element set forth in SEQ ID NO:5; and (c) a nucleic acid sequence encoding an angiogenesis regulator, the nucleic acid sequence being under regulatory control of the promoter and the hypoxia response element.

According to still another aspect of the present invention there is provided an isolated polynucleotide functional as a promoter in eukaryotic cells. The isolated polynucleotide includes an enhancer element including the sequence set forth in SEQ ID NO: 7.

According to an additional aspect of the present invention there is provided a method of regulating angiogenesis in a tissue. The method includes administering a nucleic acid construct including: (a) an endothelial cell specific promoter; (b) an enhancer element including the sequence set forth in SEQ ID NO: 7; (c) at least one copy of a hypoxia response element set forth in SEQ ID NO:5; and (d) a nucleic acid sequence encoding an angiogenesis regulator, the nucleic acid sequence being under regulatory control of the promoter, the enhancer element and the hypoxia response element.

According to still a further aspect of the present invention there is provided isolated polynucleotide functional as a promoter in eukaryotic cells, the isolated polynucleotide includes an enhancer element including at least one copy of the sequence set forth in SEQ ID NO:8.

According to still a further aspect of the present invention there is provided a method of expressing a nucleic acid sequence of interest in endothelial cells, the method includes administering to a subject a construct, the construct includes the nucleic acid sequence of interest positioned under the regulatory control of a promoter functional in eukaryotic cells, and an enhancer element including at least one copy of the sequence set forth in SEQ ID NO:8.

According to still another further aspect of the present invention there is provided isolated polynucleotide functional as a promoter in eukaryotic cells, the isolated polynucleotide includes an enhancer element including the sequence set forth in SEQ ID NO: 8.

According to further features in preferred embodiments of the invention described below, the enhancer element includes three copies of the sequence set forth in SEQ ID NO:6.

According to still further features in preferred embodiments of the invention the at least two copies of the sequence set forth in SEQ ID NO:6 are contiguous.

According to still further features in preferred embodiments of the invention the isolated polynucleotide further includes an endothelial specific promoter element.

According to still further features in preferred embodiments of the invention the endothelial specific promoter element includes at least one copy of the PPE-1 promoter.

According to still further features in preferred embodiments of the invention the isolated polynucleotide further includes a hypoxia response element.

According to still further features in preferred embodiments of the invention the hypoxia response element includes at least one copy of the sequence set forth in SEQ ID NO: 5.

According to still further features in preferred embodiments of the invention the enhancer element is as set forth in SEQ ID NO: 7.

According to still further features in preferred embodiments of the invention there is provided a nucleic acid construct including a claimed isolated polynucleotide and a nucleic acid sequence of interest, the nucleic acid sequence of interest being under regulatory control of the isolated polynucleotide.

According to still further features in preferred embodiments of the invention the nucleic acid sequence of interest is selected from the group consisting of VEGF, p55 and PDGF-BB and other growth factors, proangiogenic factors or cytokines.

According to still further features in preferred embodiments of the invention there is provided a mammalian cell transformed with a claimed isolated polynucleotide.

According to still further features in preferred embodiments of the invention the promoter exhibits endothelial cell specificity.

According to still further features in preferred embodiments of the invention the promoter is the PPE-1 promoter as set forth in SEQ ID NO: 1.

According to still further features in preferred embodiments of the invention administering is effected by a method selected from the group consisting of: (i) systemic in-vivo administration; (ii) ex-vivo administration to cells removed from a body of a subject and subsequent reintroduction of the cells into the body of the subject; and (iii) local in-vivo administration.

According to still further features in preferred embodiments of the invention the nucleic acid construct further includes an enhancer element including at least two copies of the sequence set forth in SEQ ID NO:6.

According to still further features in preferred embodiments of the invention the endothelial cell specific promoter includes at least one copy of the PPE-1 promoter.

According to still further features in preferred embodiments of the invention there is provided a nucleic acid construct including a claimed isolated polynucleotide and a nucleic acid sequence of interest, the nucleic acid sequence of interest being under regulatory control of the isolated polynucleotide.

According to still further features in the described preferred embodiments the enhancer element further includes at least one copy of the sequence set forth in SEQ ID NO:6.

According to still further features in the described preferred embodiments the enhancer element includes one copy of the sequence set forth in SEQ ID NO:8 and at least two copies of the sequence set forth in SEQ ID NO:6.

According to still further features in the described preferred embodiments the enhancer element further includes at least one copy of the sequence set forth in SEQ ID NO:6.

According to still further features in the described preferred embodiments the at least one copy includes two copies.

According to still further features in the described preferred embodiments the nucleic acid construct further includes an enhancer element including at least one copy of the sequence set forth in SEQ ID NO:8.

According to yet another further aspect of the present invention there is provided method of regulating angiogenesis in a tissue, the method comprising administering a nucleic acid construct including: (a) an endothelial cell specific promoter; (b) an enhancer element including at least one copy of the sequence set forth in SEQ ID NO:8; and (c) a nucleic acid sequence encoding an angiogenesis regulator, the nucleic acid sequence being under regulatory control of the promoter and the enhancer element.

According to still further features in the described preferred embodiments the enhancer element further includes at least one copy of the sequence set forth in SEQ ID NO:6.

According to still further features in the described preferred embodiments the enhancer element includes one copy of the sequence set forth in SEQ ID NO:8 and at least two copies of the sequence set forth in SEQ ID NO:6.

The present invention successfully addresses the shortcomings of the presently known configurations by providing improved isolated polynucleotide sequences with endothelial cell specificity, and methods of use thereof. The improvements in the sequence make feasible methods of treating a variety of diseases, disorders and conditions, which were previously considered infeasible. Specifically, the improvements relate to increased specificity to endothelial cells, increased levels of expression of a sequence of interest and enhanced induction by conditions including ischemia and angiogenesis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a histogram illustrating the effect of the enhancer element of the present invention on Luciferase expression in both bovine and human endothelial cell lines using the B2B cell line as a non-endothelial control.

FIG. 2 is a histogram illustrating endothelial specificity of a promoter of the present invention in an adenoviral vector on Luciferase expression in various cell lines.

Figure 3A:
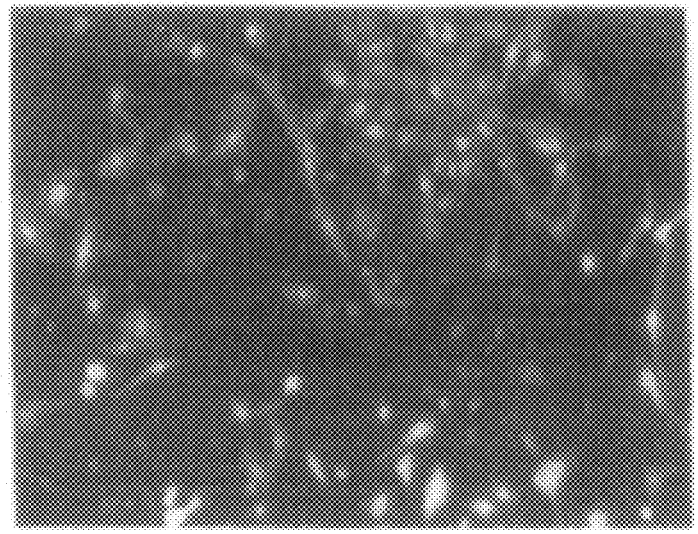
Figure 3B:
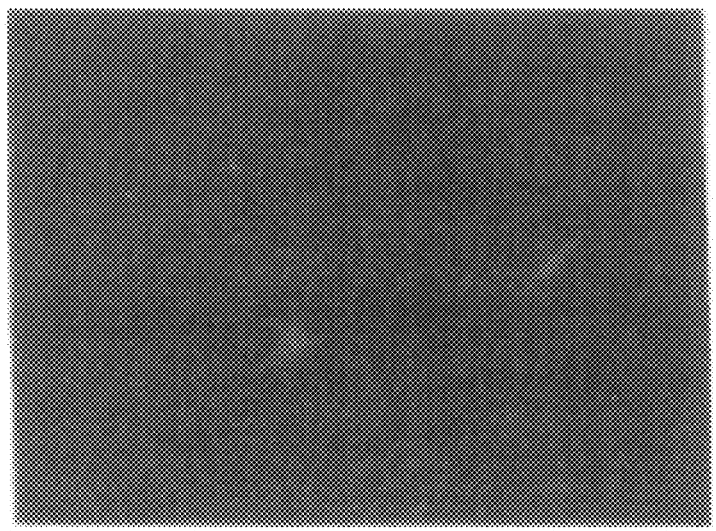

FIGS. 3A-B are photomicrographs illustrating GFP expression under the control of Ad5PPE-1-3X of the present invention and an Ad5CMV control construct in the BAEC cell line.

Figure 4:
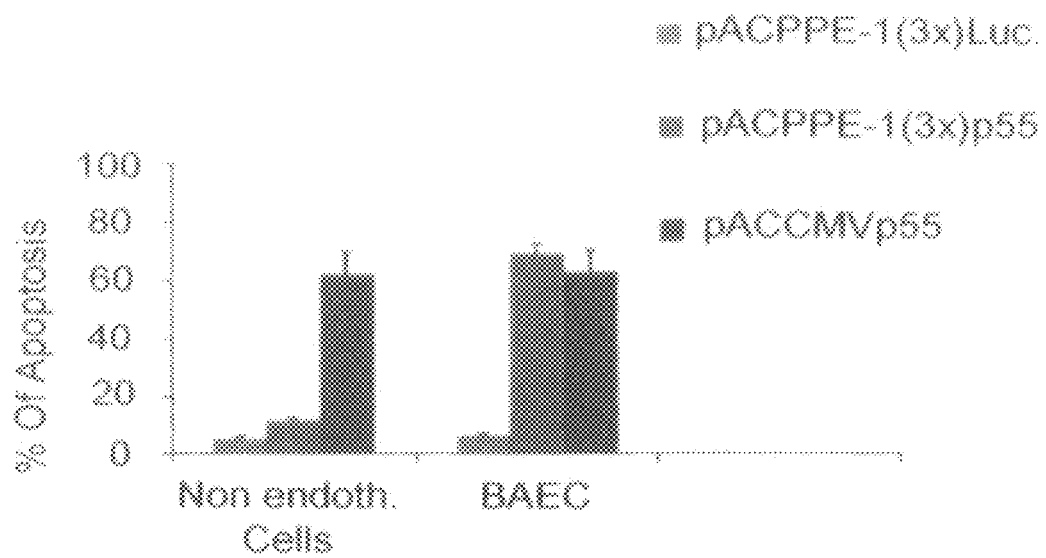

FIG. 4 is histogram of % apoptosis induced by pACPPE-1-3Xp55, pACPPE-1-3XLuciferase and pCCMVp55 in endothelial and non-endothelial cells.

Figure 5:
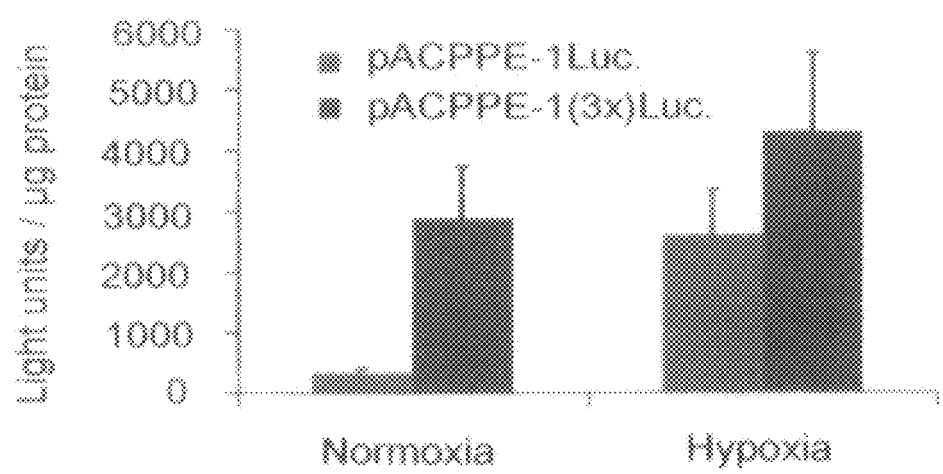

FIG. 5 is a histogram illustrating the effect of introducing an enhancer element according to the present invention into a promoter construct on hypoxia response.

Figure 6:
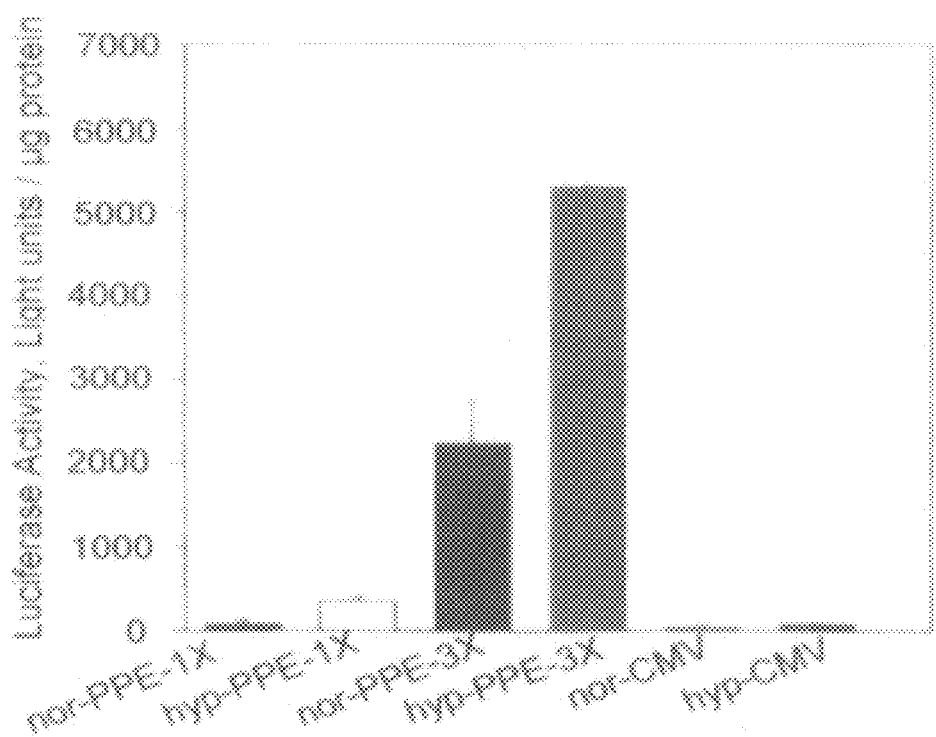

FIG. 6 is a histogram illustrating the effect of introducing an enhancer element according to the present invention into a promoter of an adenovector construct on hypoxia response.

Figure 7:
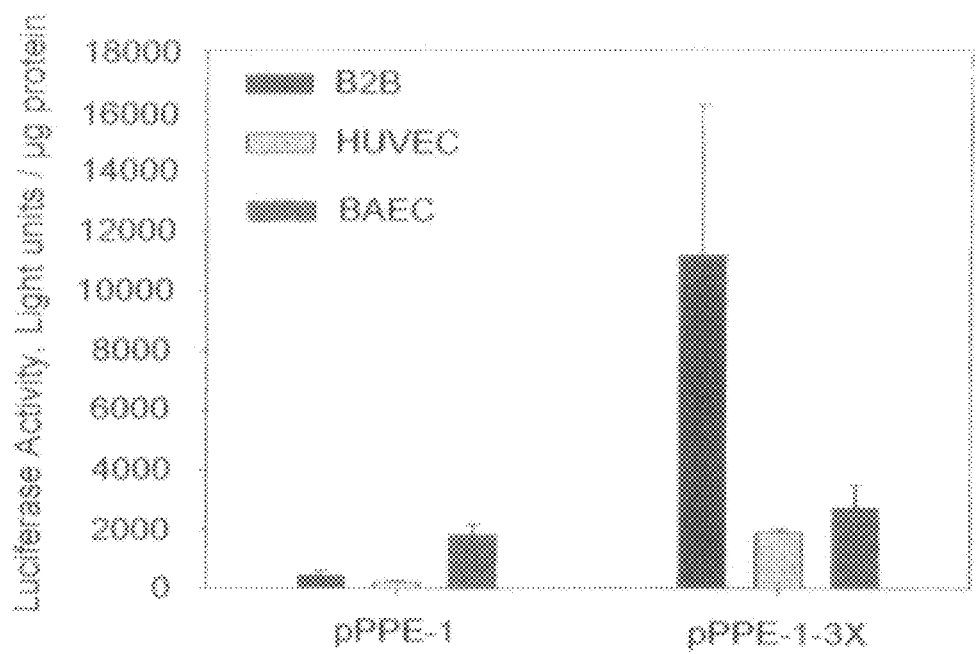

FIG. 7 is a histogram illustrating the effect of introducing an enhancer element according to the present invention into a promoter on levels of expression in bovine and human endothelial cell lines.

Figure 8:
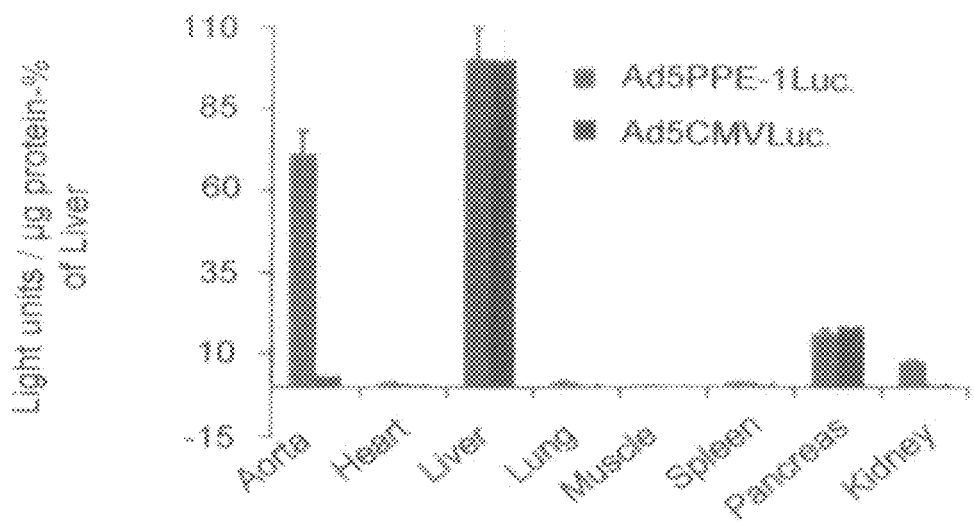
Figure 9A:
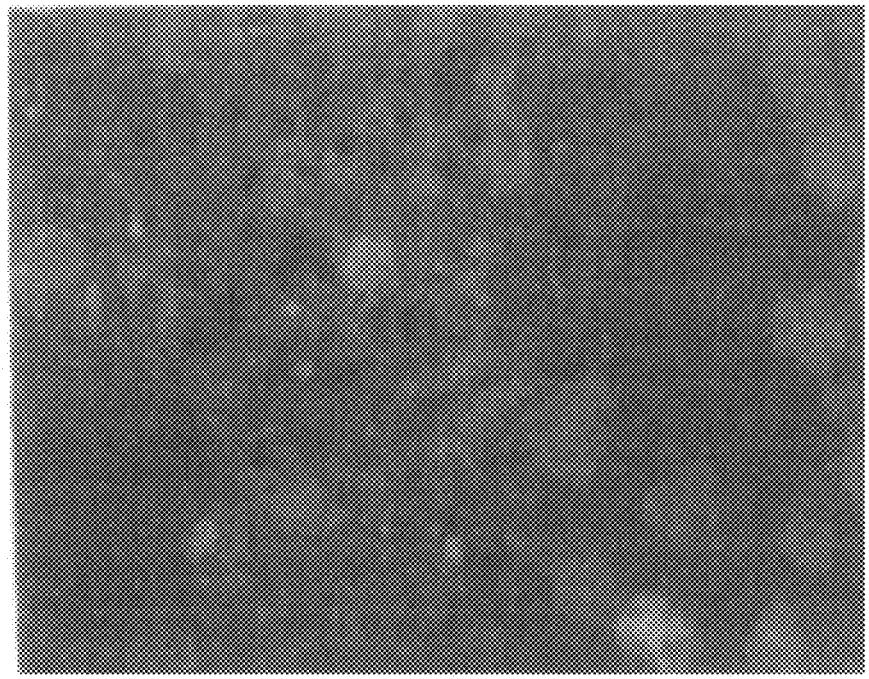
Figure 9B:
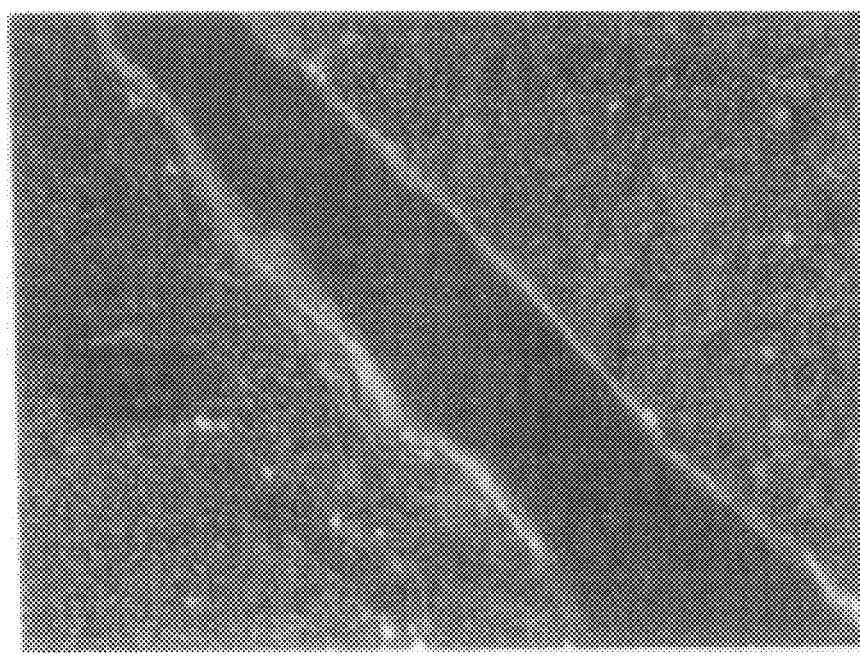

FIG. 8 is a histogram illustrating levels of expression of a reporter gene observed in various organs following injection of an adenoviral construct containing either an endothelial promoter (PPE-1) or a control (CMV) promoter;

FIGS. 9A-B are two photomicrographs illustrating cellular expression of an Ad5CMVGFP construct (FIG. 9A) and an Ad5PPE-1-GFP construct (FIG. 9B) in liver tissue of mice injected with the constructs.

Figure 10:
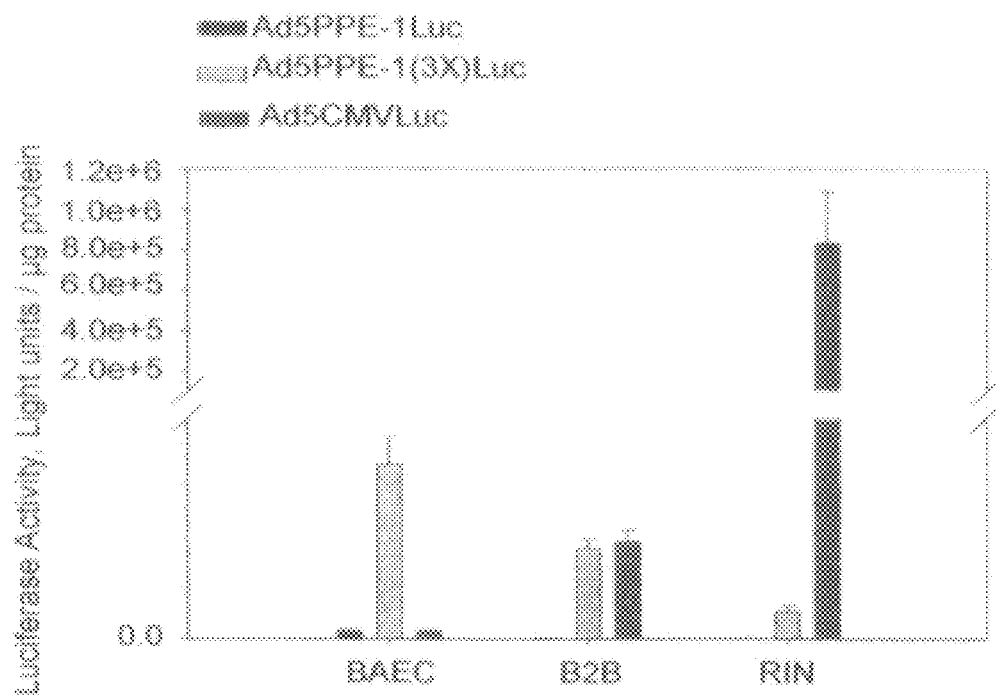

FIG. 10 is a histogram illustrating the effect of introducing an enhancer element according to the present invention into a promoter on levels of expression in endothelial and non-endothelial cell lines.

Figure 11:
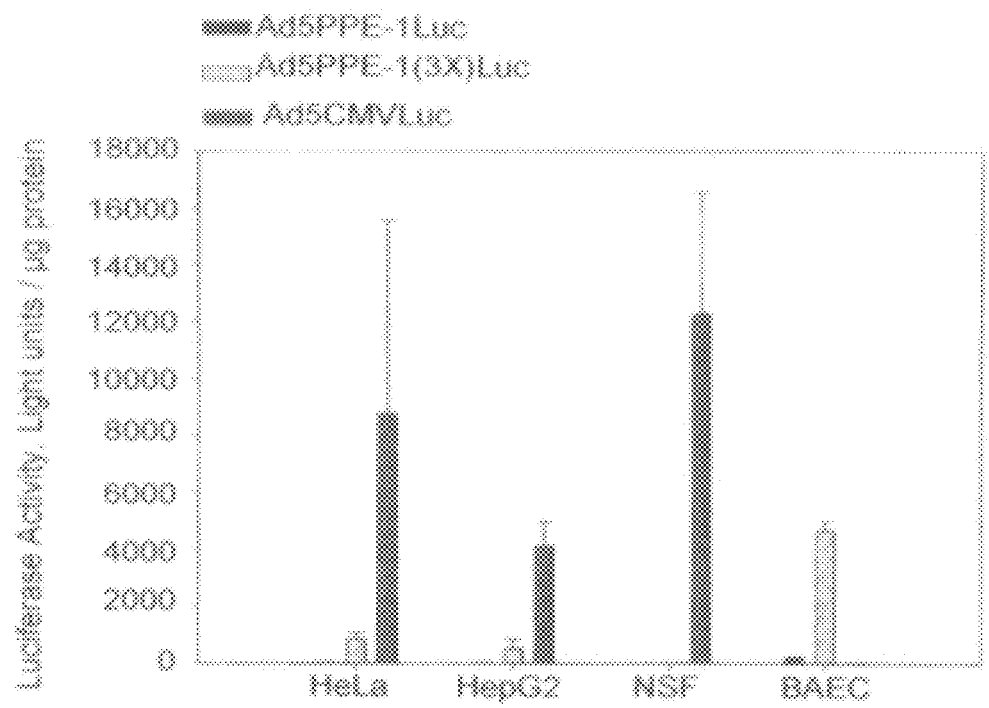

FIG. 11 is a histogram illustrating the effect of introducing an enhancer element according to the present invention into a promoter on levels of expression in endothelial and non-endothelial cell lines.

Figure 12A:
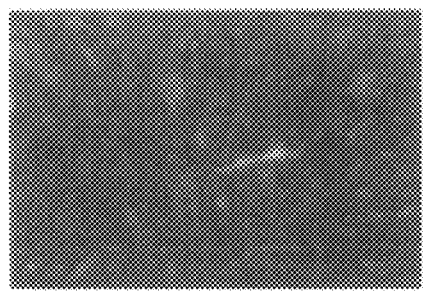
Figure 12B:
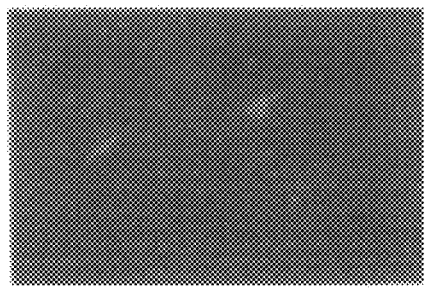
Figure 12C:
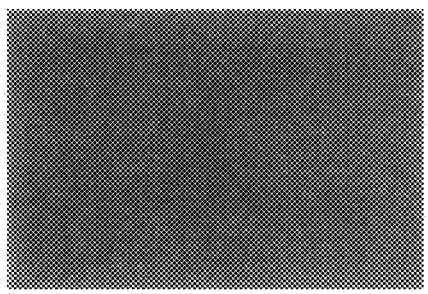

FIGS. 12A-C are photomicrographs illustrating GFP expression in Ad5PPE-1-3XGFP transduced cells, Ad5PPE-1GFP transduced cells and Ad5CMVGFP transduced cells respectively.

Figure 13A:
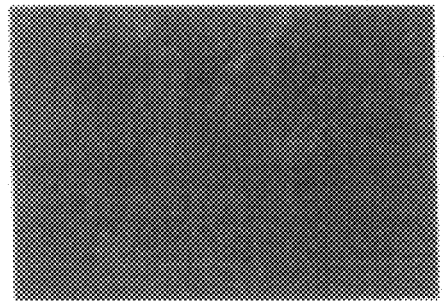
Figure 13B:
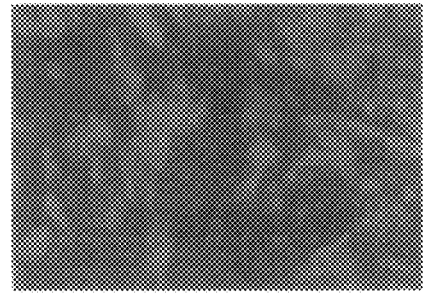

FIGS. 13A-B illustrate GFP expression in SMC transduced by moi-1 of Ad5PPE-1-3XGFP and Ad5CMVGFP respectively.

Figure 14A:
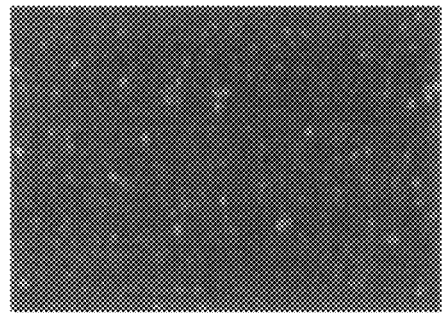
Figure 14B:
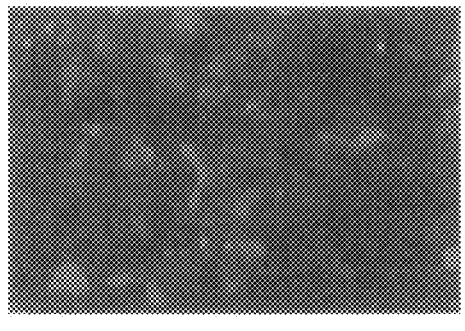

FIGS. 14A-B show results of an experiment similar to that of FIGS. 13A-B conducted in HeLa cells.

Figure 15A:
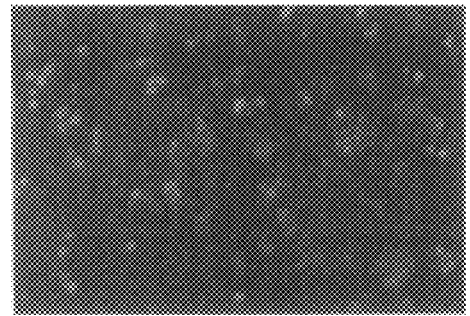
Figure 15B:
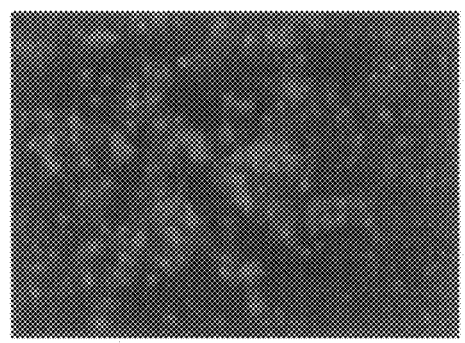

FIGS. 15A-B show results of an experiment similar to that of FIGS. 13A-B conducted in HepG2 cells.

Figure 16A:
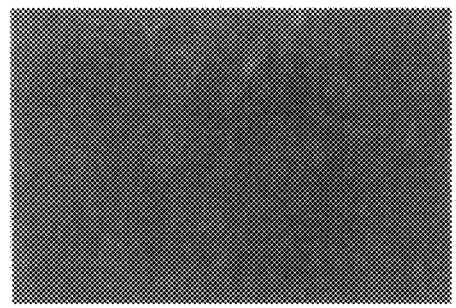
Figure 16B:
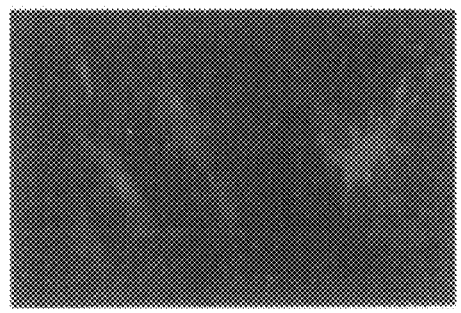

FIGS. 16A-B show results of an experiment similar to that of FIGS. 13 A-B conducted in NSF cells.

Figure 17A:
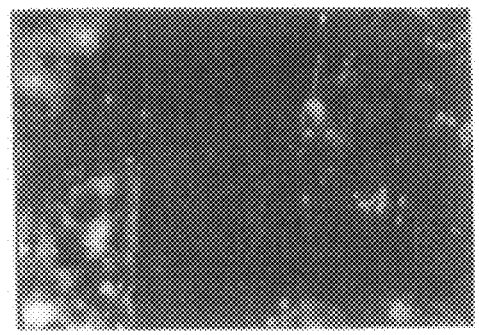
Figure 17B:

FIGS. 17A-B are photomicrographs illustrating GFP expression in endothelial cells lining a blood vessel of mice injected with the Ad5PPE-1GFP and the Ad5PPE-1-3XGFP constructs respectively.

Figure 18A:
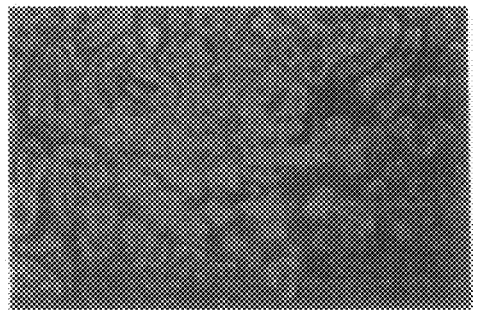
Figure 18B:
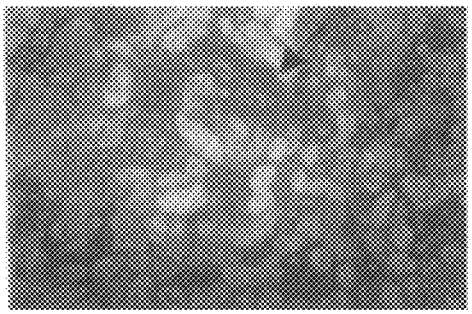
Figure 18C:

FIGS. 18A-C are photomicrographs illustrating results from kidney tissue of injected mice. Ad5CMVGFP injected mice (FIG. 18A), Ad5PPE-1GFP (FIG. 18B; slightly higher GFP expression is visible in the blood vessel wall; indicated by arrow) and Ad5PPE-1-3XGFP (FIG. 18C).

Figure 19A:
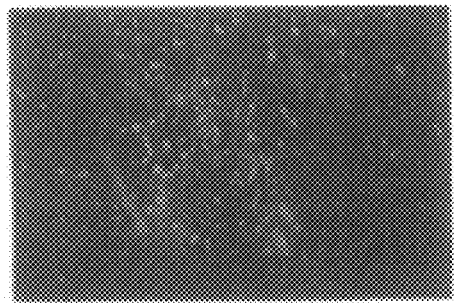
Figure 19B:
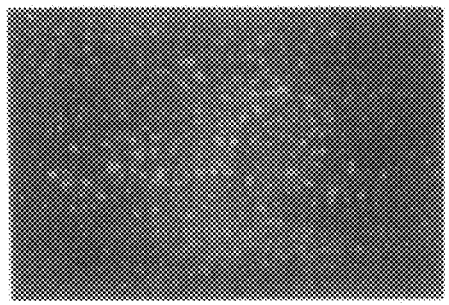
Figure 19C:
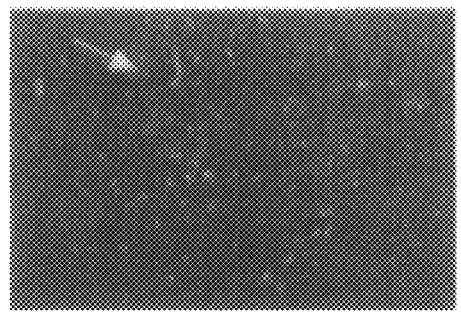

FIGS. 19A-C illustrate experiments similar to those depicted in FIGS. 18A-C, conducted on sections of spleen tissue.

Figure 20A:
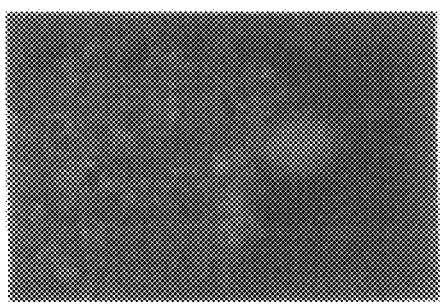
Figure 20B:
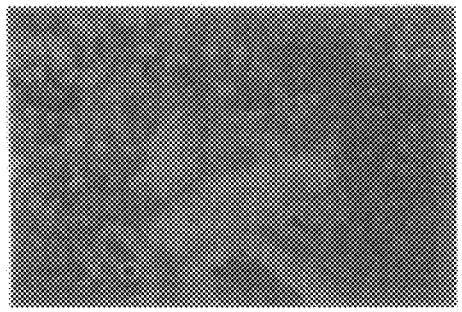
Figure 20C:
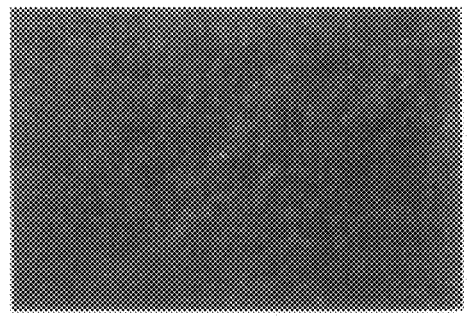
Figure 20C:
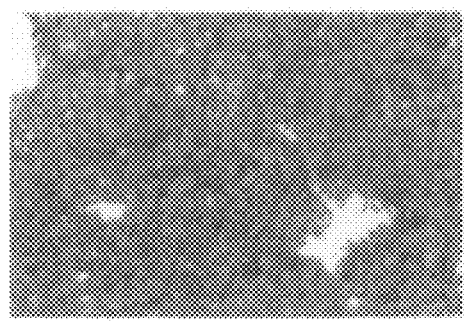
Figure 20D:
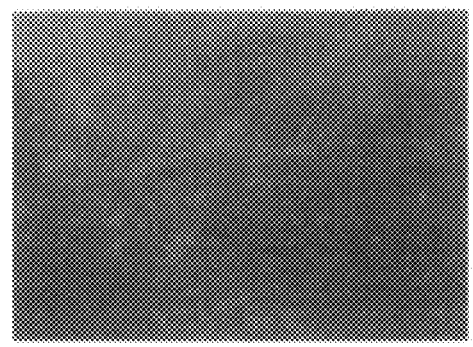
Figure 20D:
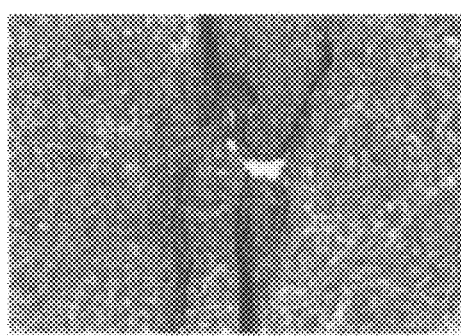

FIGS. 20A-D and 20 C'-D' illustrate GFP expression in metastatic lungs of control mice injected with Saline (FIG. 20A), mice injected with Ad5CMVGFP (FIG. 20 B), mice injected with Ad5PPE-1GFP (FIG. 20 C) and mice injected with Ad5PPE-1-3XGFP (FIG. 20D). Anti Cd31 immunostaining (FIGS. 20C' to 20D') confirm the co-localization of the GFP expression and CD31 expression in each metastatic tissue.

Figure 21:
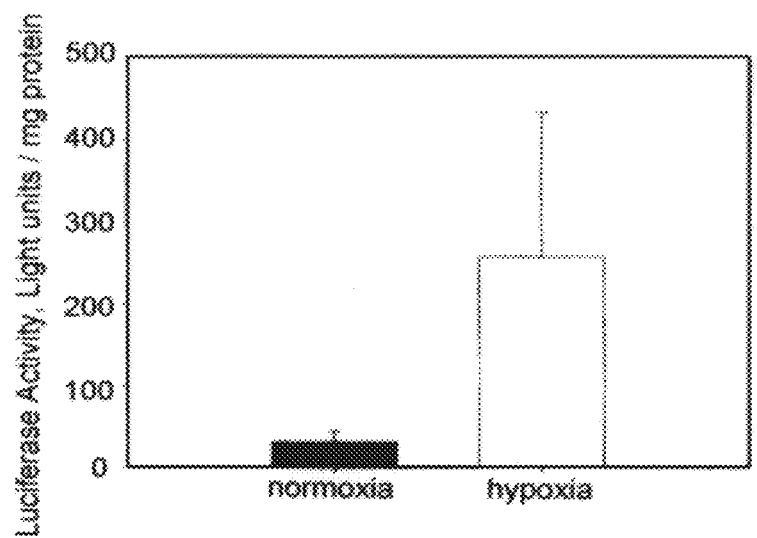

FIG. 21 is a histogram illustrating that Luciferase activity (light units/µg protein) in BAEC transfected by a plasmid containing the murine PPE-1 promoter is significantly higher when transfected cells were incubated under hypoxic conditions.

Figure 22:
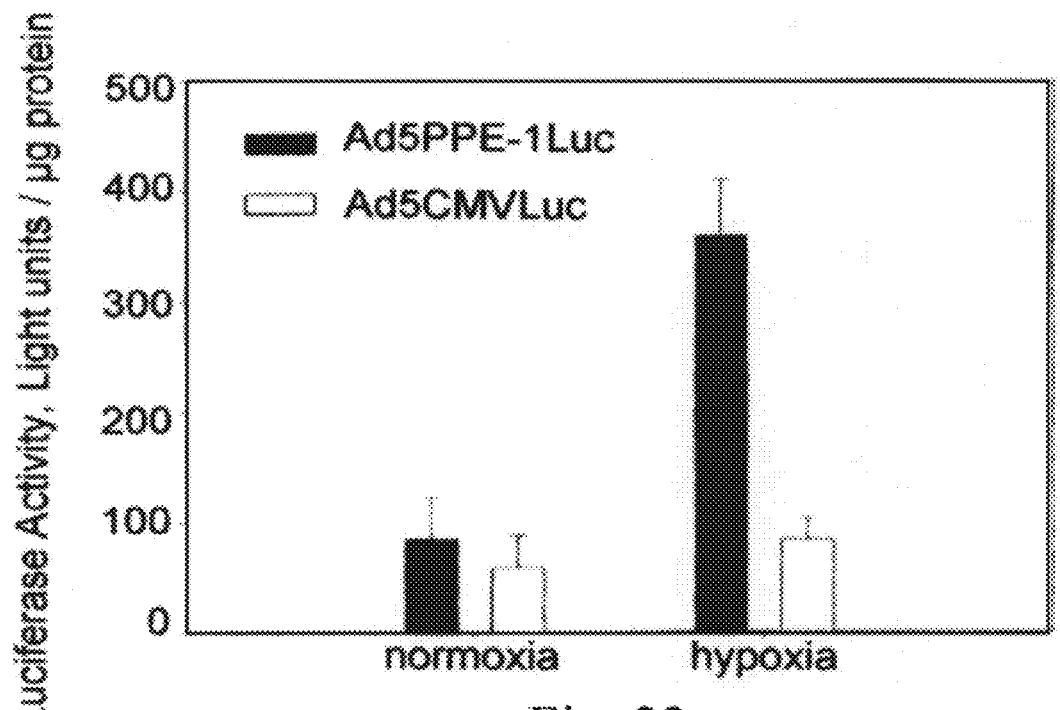

FIG. 22 is a histogram as in FIG. 21, except that Ad5PPE-1Luc and Ad5CMVLuc were employed.

Figure 23:
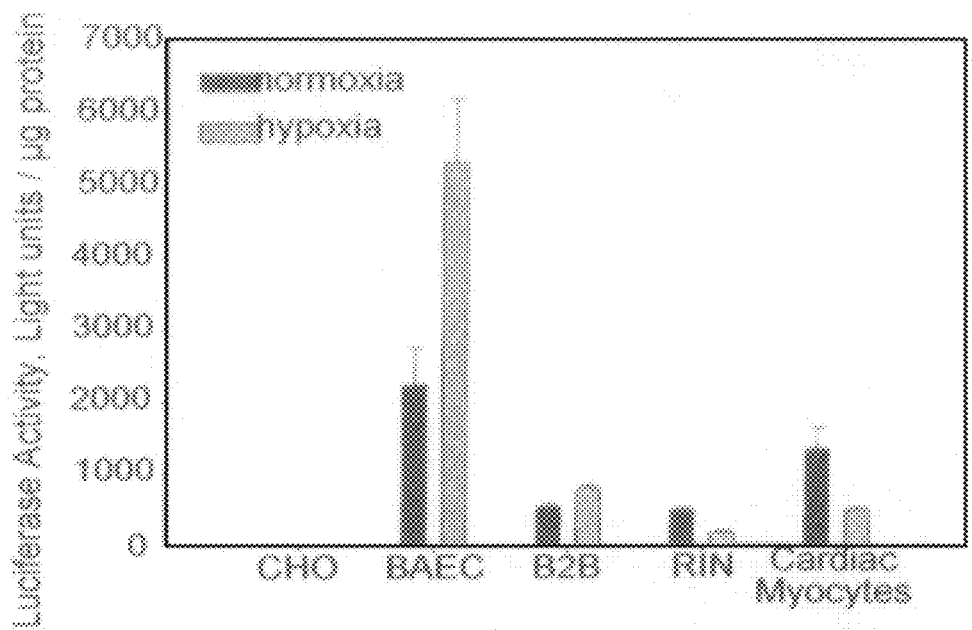

FIG. 23 is a histogram as in FIG. 22 showing the effects of hypoxia in different cell lines.

Figure 24:
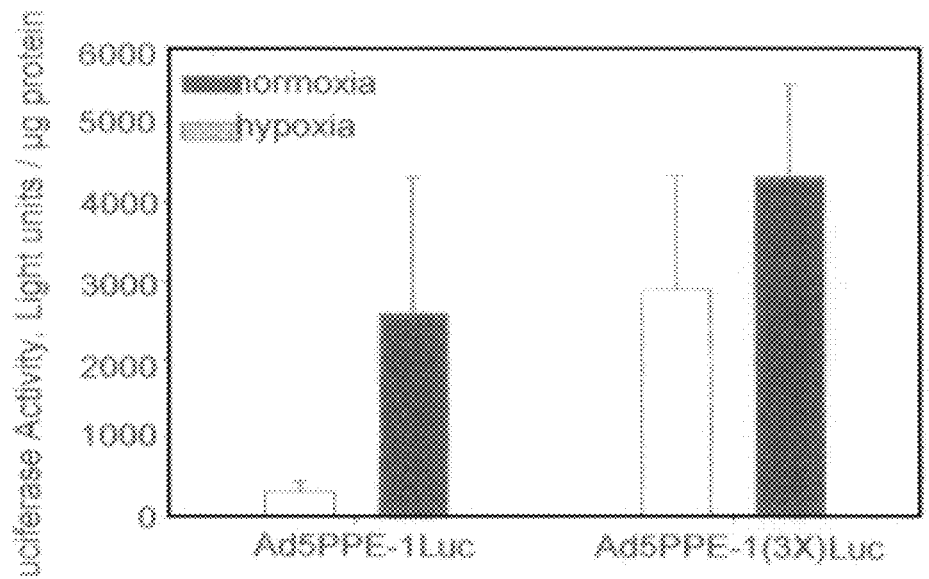

FIG. 24 is a histogram illustrating the effect of the 3X sequence of the present invention on the PPE-1 hypoxia response in BAEC cells. Cells were transduced by Ad5PPE-1Luc and Ad5PPE-1-3XLuc.

Figure 25:
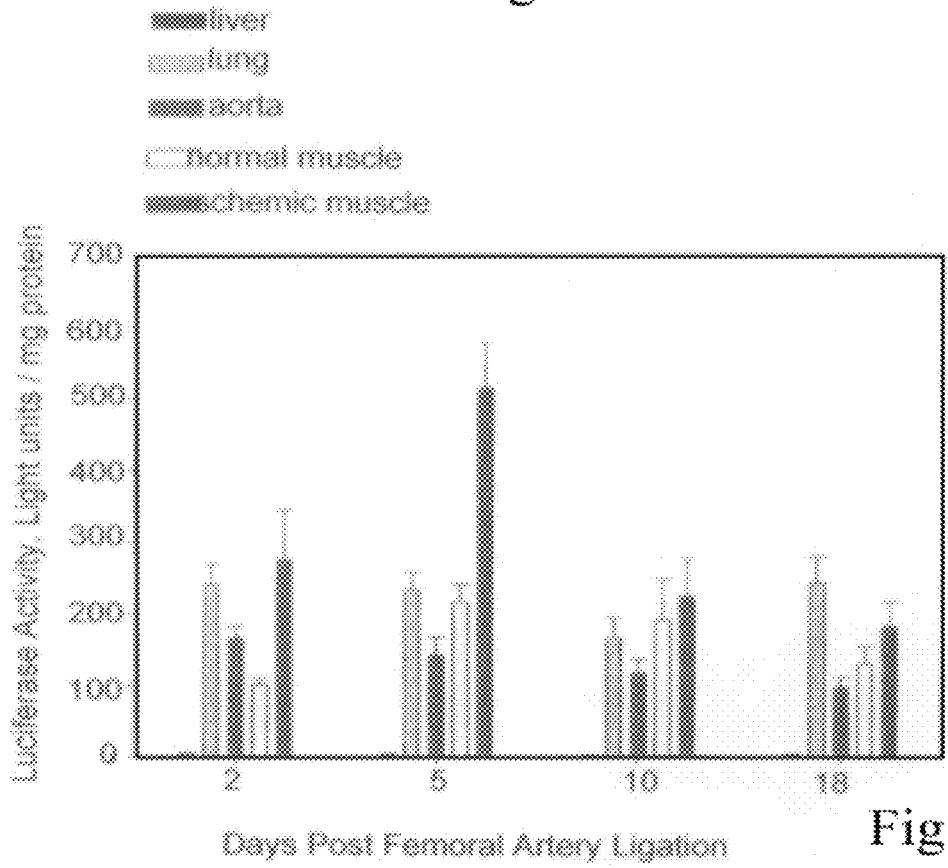

FIG. 25 is a histogram showing levels of Luciferase expression in various tissues of PPE-1-Luc transgenic mice following femoral artery ligation.

Figure 26A:
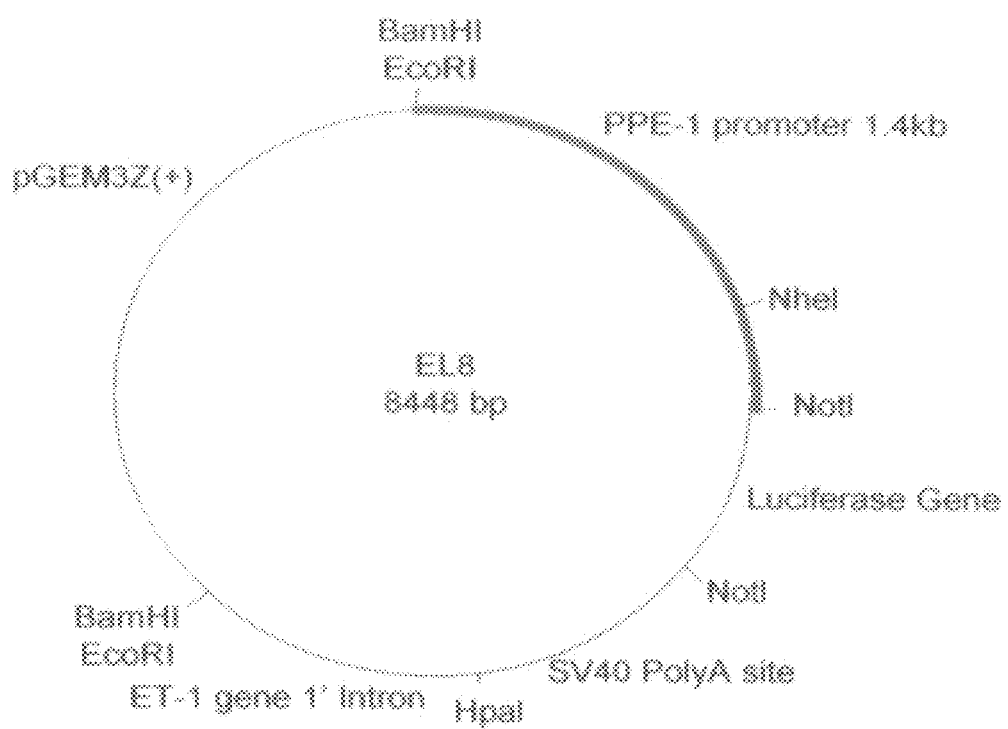
Figure 26B:
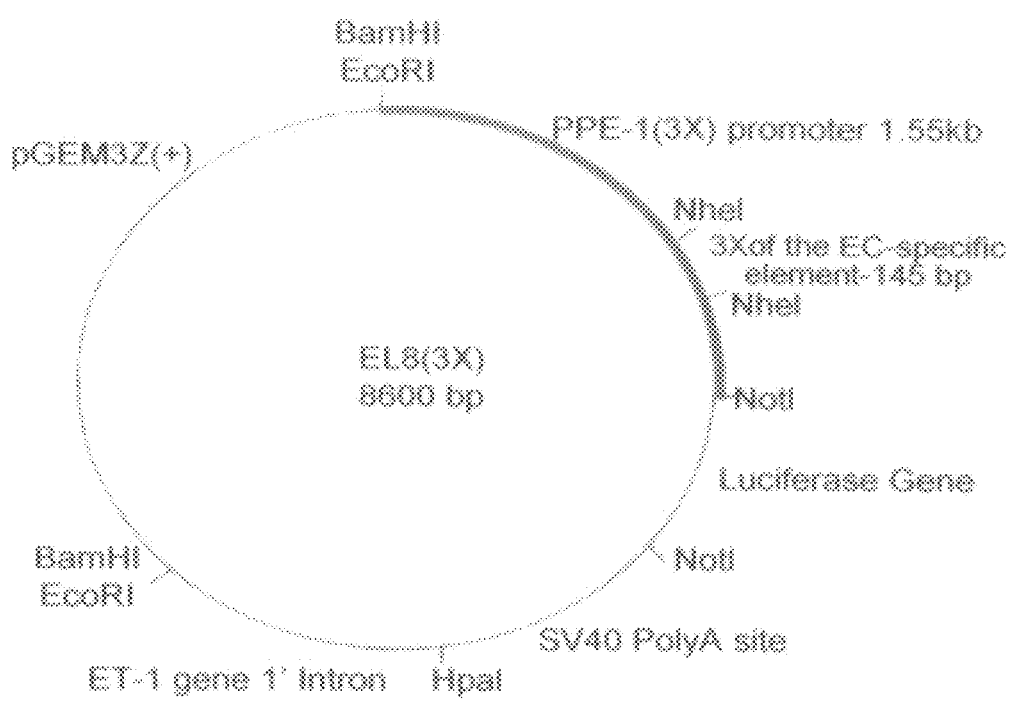

FIGS. 26A-B are plasmid maps of constructs employed in conjunction with the present invention.

Figure 27A:
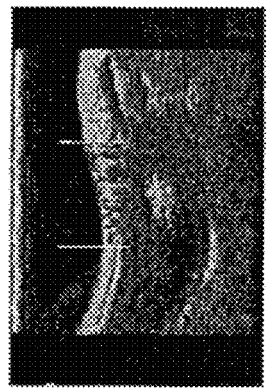
Figure 27B:
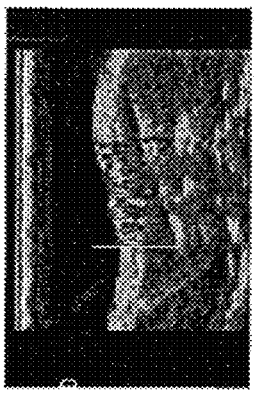
Figure 27C:
Figure 27D:
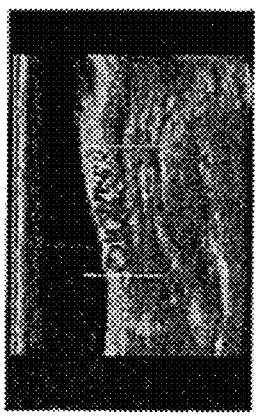
Figure 27E:
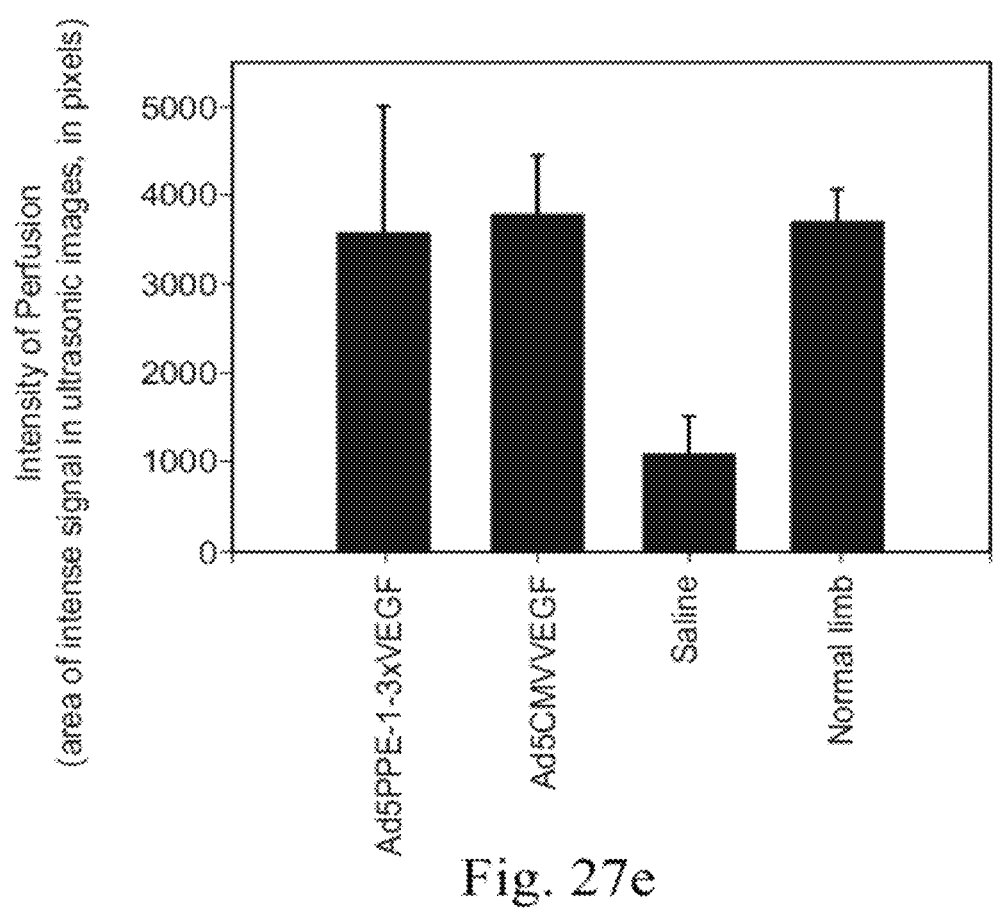
Figure 27F:
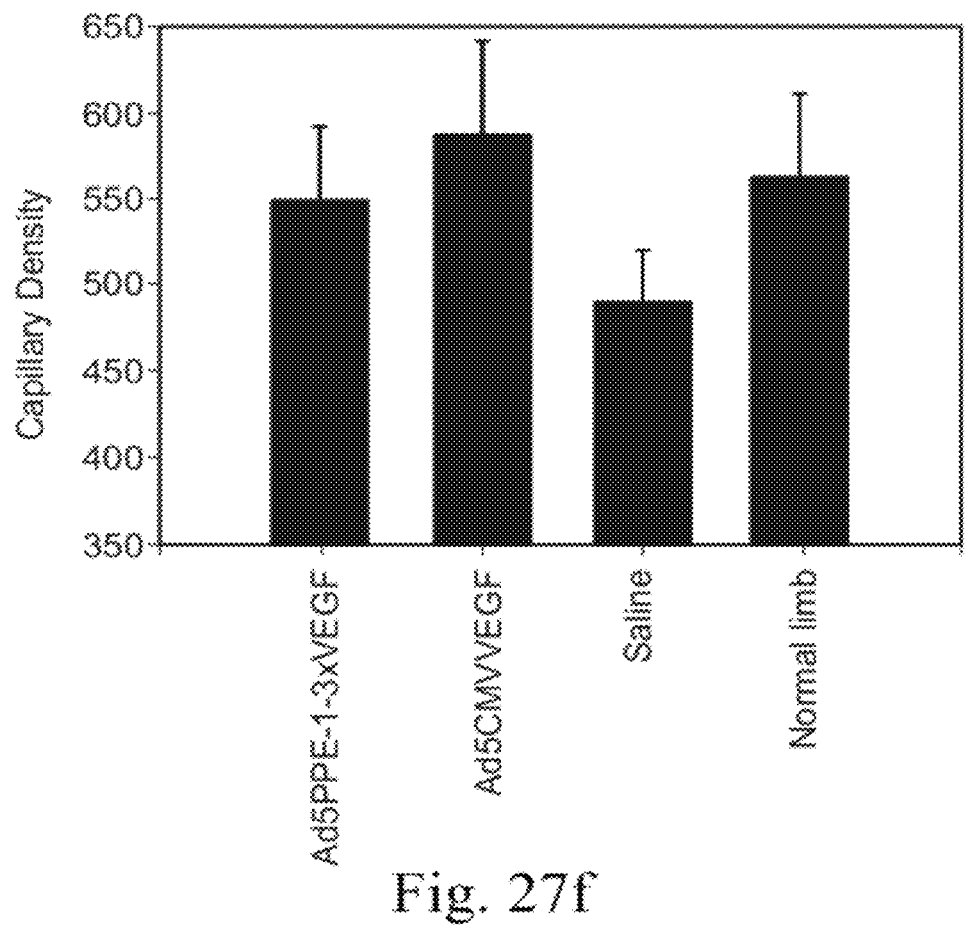

FIGS. 27A-F illustrate the effects of Ad5PPE-1-3XVEGF and Ad5CMVVEGF on blood perfusion and angiogenesis in mouse ischemic limbs. FIGS. 27A-D are representative ultrasonic (US) angiographic images of perfusion in the ischemic limb of mice from the various treatment groups captured 21 days following ligation. Yellow signal represents intense perfusion. The right side of the image represents the distal end of the limb. FIG. 27A—Ad5PPE-1-3XVEGF treated mouse; FIG. 27B—Ad5CMVVEGF treated mouse; FIG. 27C—control, saline treated mouse; FIG. 27D—control, normal limb. FIGS. 27E-F are histograms illustrating: mean intensity of signal in the US images of the various treatment groups (FIG. 27E); mean capillary density, measured as the number of CD31+ cells/mm$^2$ in the various treatment groups (FIG. 27F).

Figure 28:
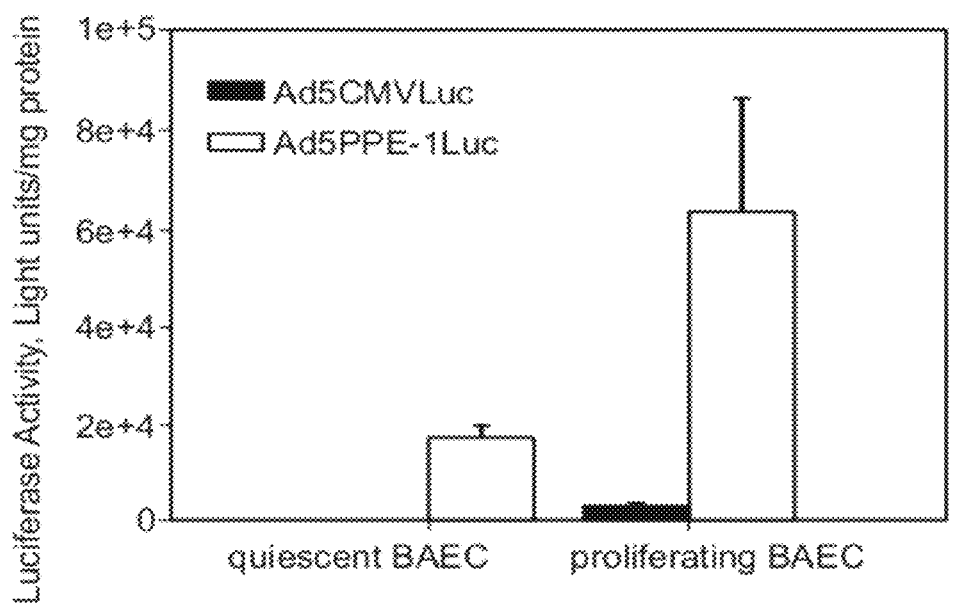

FIG. 28 is a histogram illustrating Luciferase activity in proliferating and quiescent Bovine Aortic Endothelial Cells (BAEC) transduced with Ad5PPE-1Luc (open bars) and Ad5CMVLuc (black bars).

Figure 29:
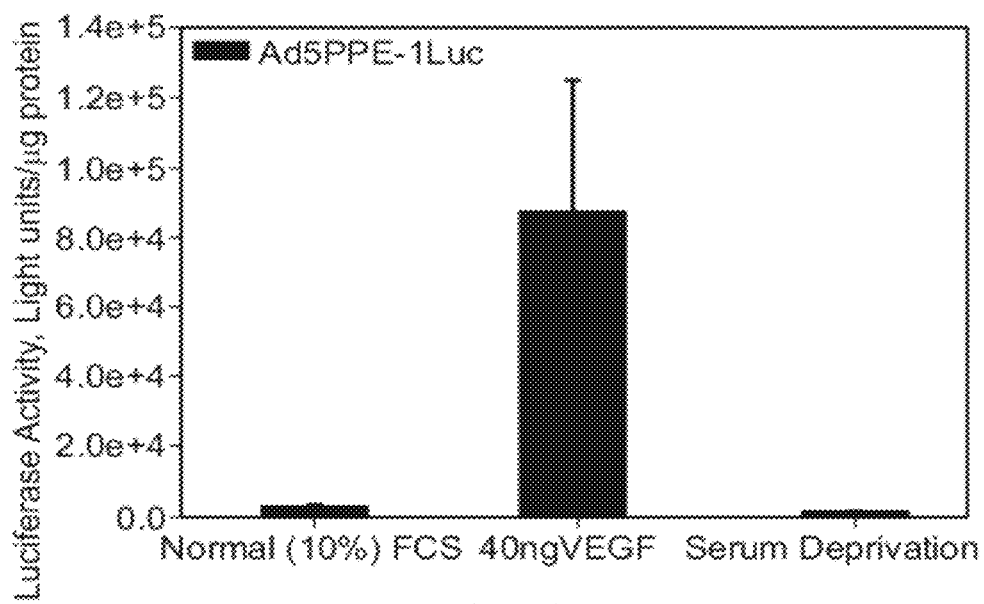

FIG. 29 is a histogram illustrating Luciferase activity in BAEC transduced with Ad5PPE-1Luc. during normal proliferation, a quiescent state and rapid proliferation following addition of VEGF.

Figure 30A:
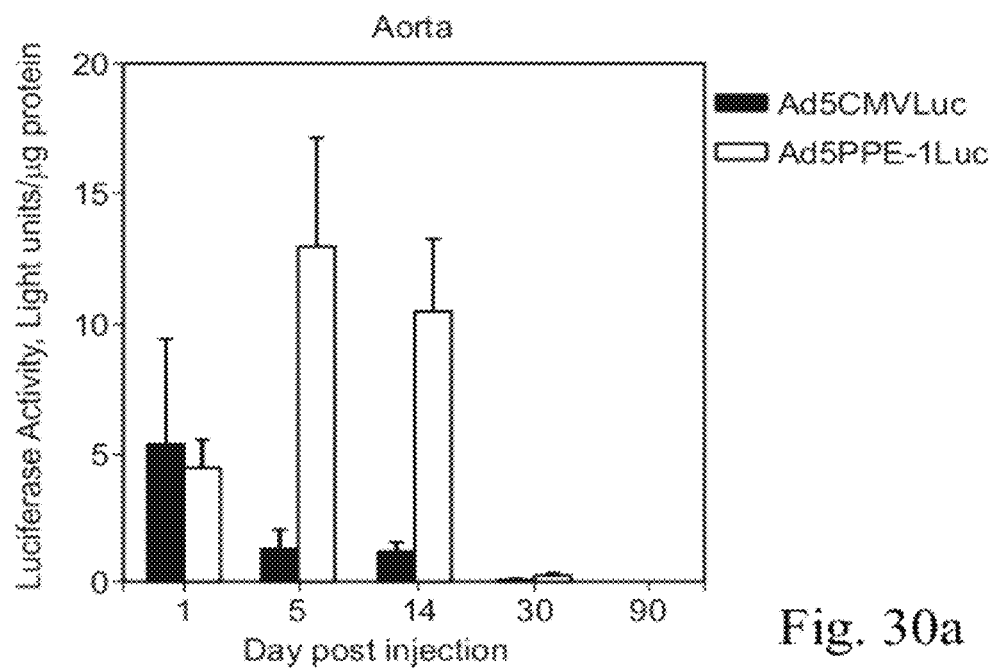
Figure 30B:
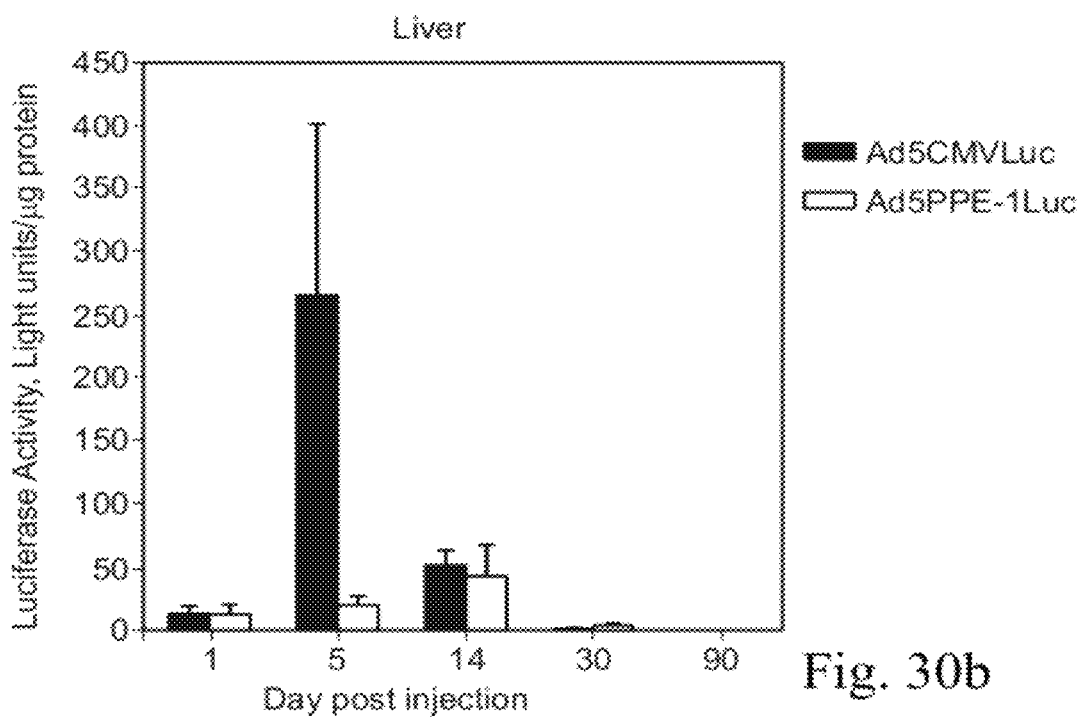

FIGS. 30A-B are histograms illustrating Luciferase activity (light units/µg protein) in the (FIG. 30A) aortas and livers (FIG. 30B) of Ad5PPE-1Luc and Ad5CMVLuc normal injected C57BL/6 mice. Activities were determined 1 (n=13), 5 (n=34), 14 (n=32), 30 (n=20) and 90 (n=11) days post injection.

Figure 31A:
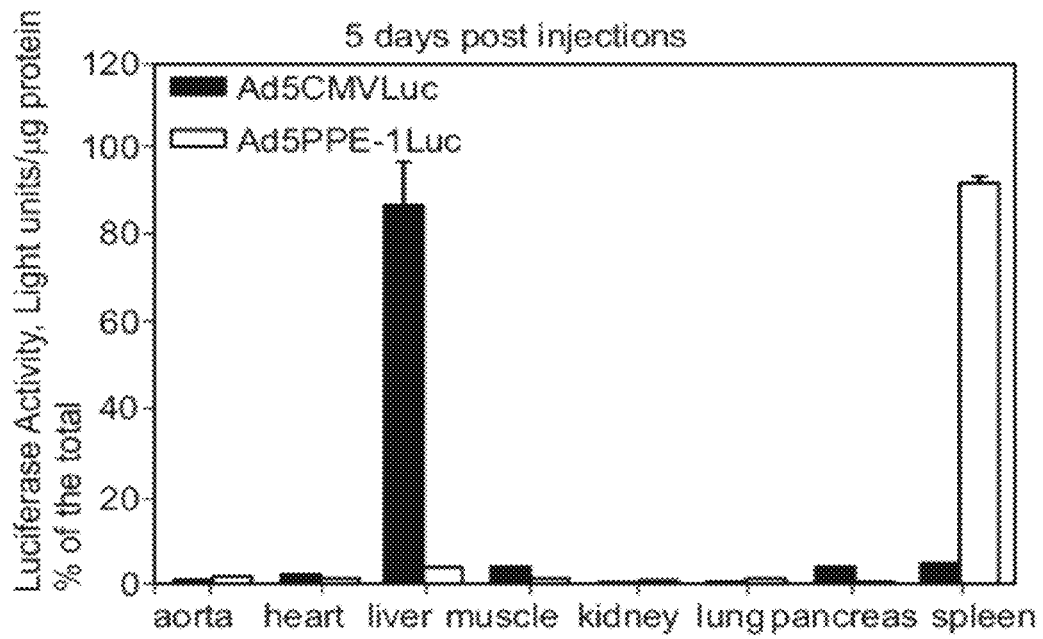
Figure 31B:
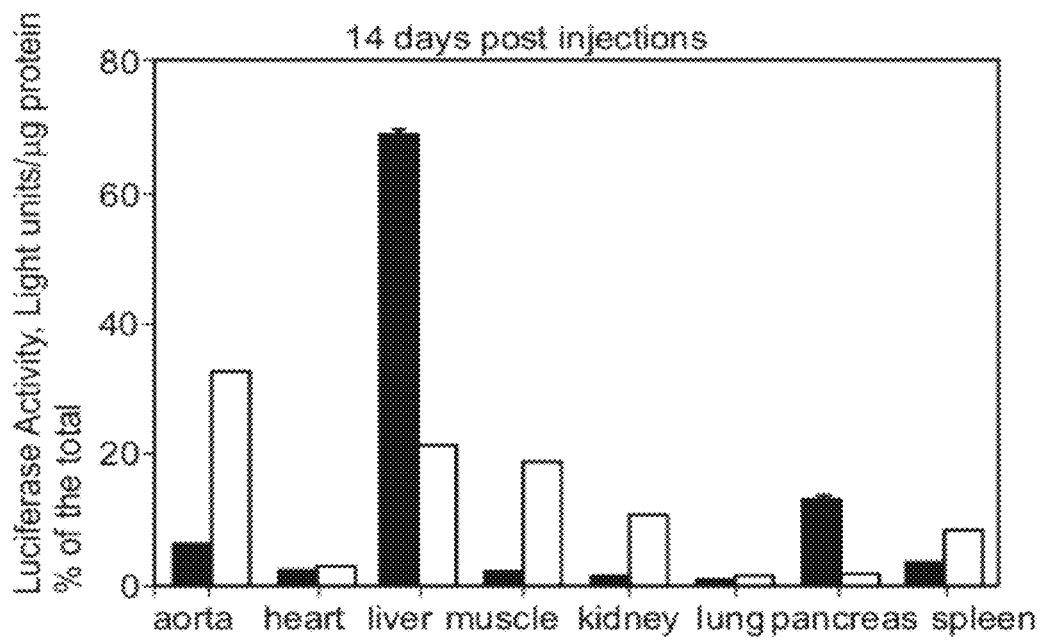

FIGS. 31A-B are histograms illustrating relative Luciferase activity (light units/µg protein) detected five (FIG. 31A) and fourteen (FIG. 31B) (n=10 for each time point) days post injection of Ad5PPE-1Luc (open bars) or Ad5CMVLuc (black bars) in normal injected BALB/C mice. Activity is expressed as percentage of total body Luciferase expression of each animal.

Figure 32:
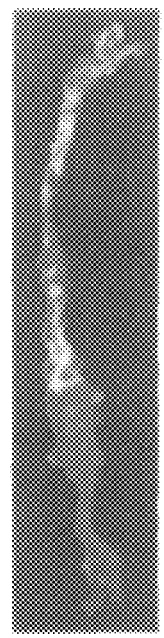

FIG. 32 is a prior art image depicting an Aorta dissected from ApoE deficient mice colored by Sudan—IV. The thoracic aorta contains less red stained atherosclerotic lesion while the abdominal region includes many red stained atherosclerotic lesions. (Adapted from Imaging of Aortic atherosclerotic lesions by $^{125}$I-HDL and $^{125}$I-BSA. A. Shaish et al, Pathobiology—submitted for publication).

Figure 33:
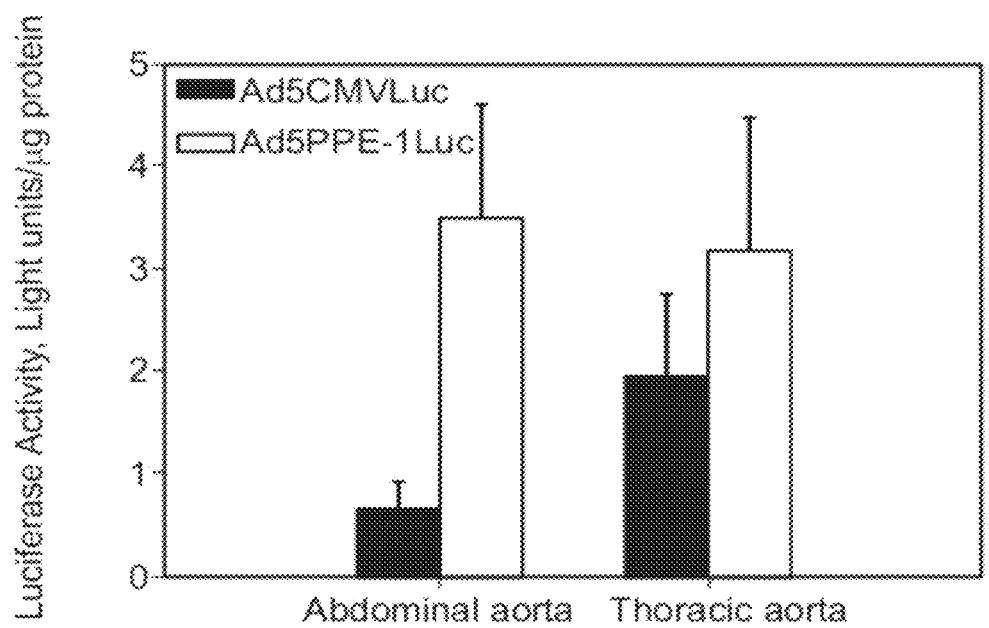

FIG. 33 is a histogram illustrating absolute Luciferase activity (light units/µg protein) detected 5 days post systemic injections of Ad5PPE-1Luc (open bars; n=12) or Ad5CMVLuc (black bars; n=12) to ApoE deficient mice. Luciferase activity observed from the abdominal aorta contain high lesion levels and from the thoracic area (low lesion levels).

Figure 34:
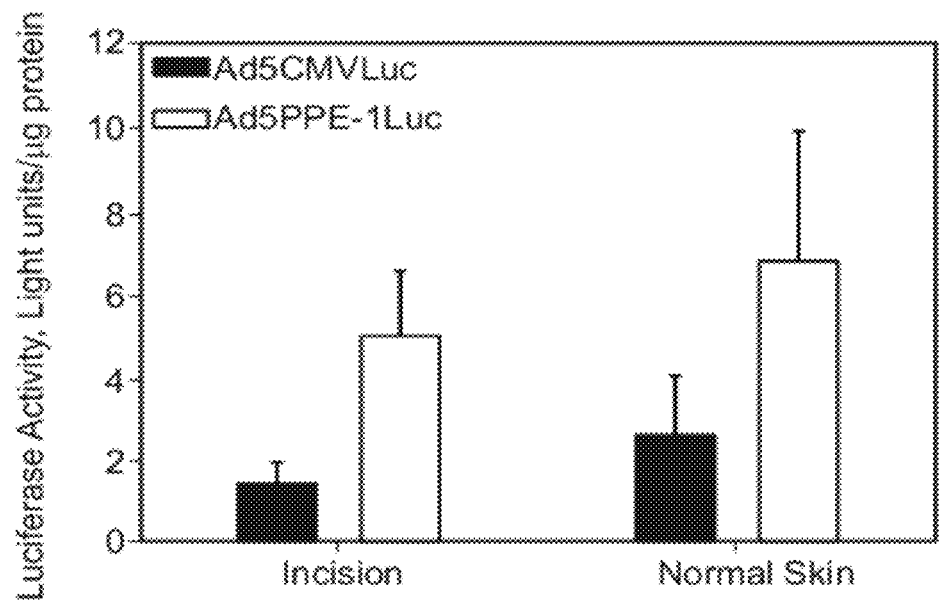

FIG. 34 is a histogram illustrating absolute Luciferase activity (light units/µg protein) 5 days post systemic injections of Ad5PPE-1Luc (black bars) or Ad5CMVLuc (open bars) to healing wound C57BL/6 induced mice.

Figure 35:
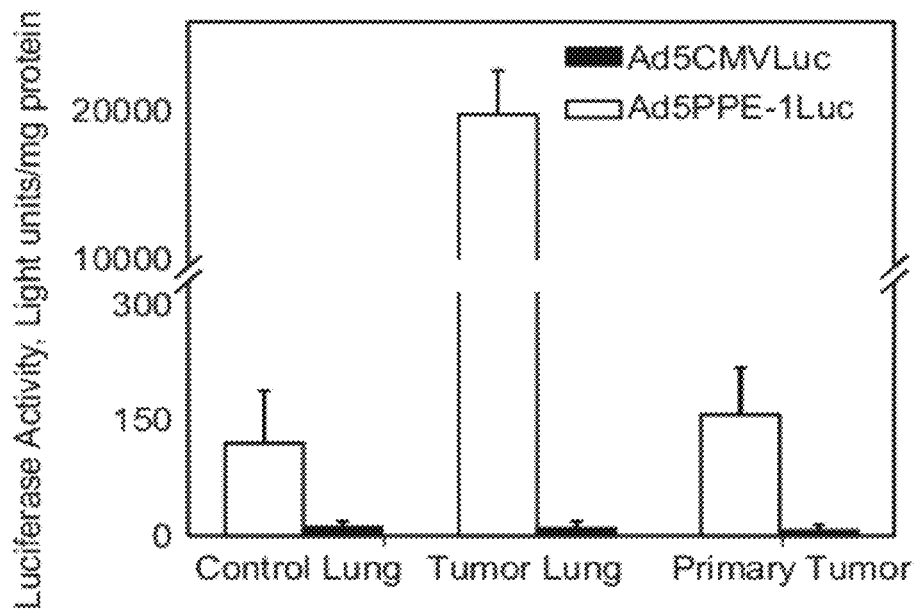

FIG. 35 is a histogram illustrating Luciferase activity in normal lung, metastatic lung and primary tumor of Lewis lung carcinoma-induced mice. Lewis lung carcinoma was induced by D122-96 cells injection to the backs for primary tumor model and to the footpad for the metastatic model. Luciferase activity was measured five days post-systemic injection of Ad5PPE-1Luc (n=9; open bars) or Ad5CMVLuc (n=12; black bars). Activity is expressed as light units/µg protein.

Figure 36A:
Figure 36B:
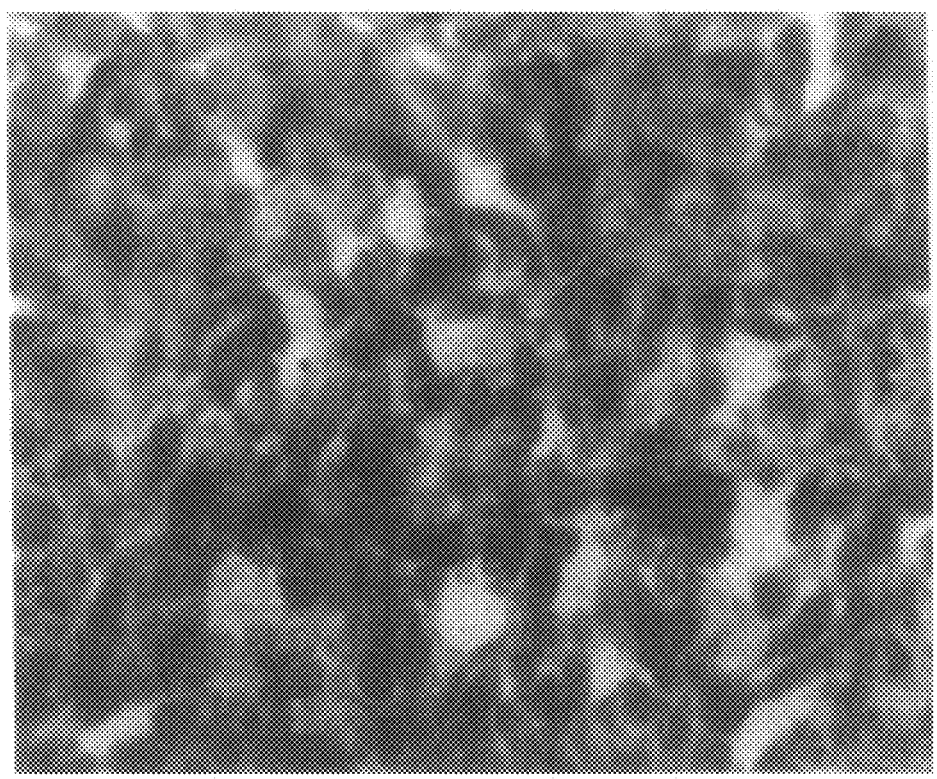
Figure 36C:
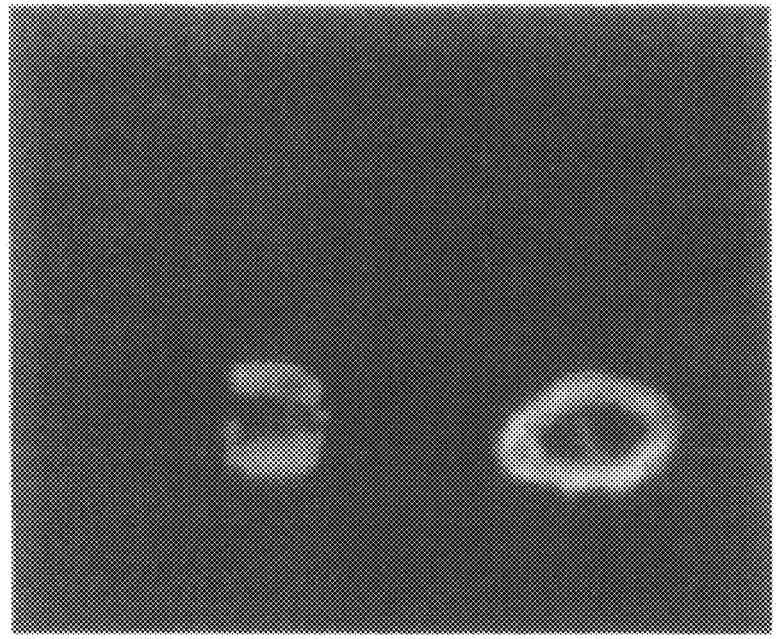
Figure 36D:
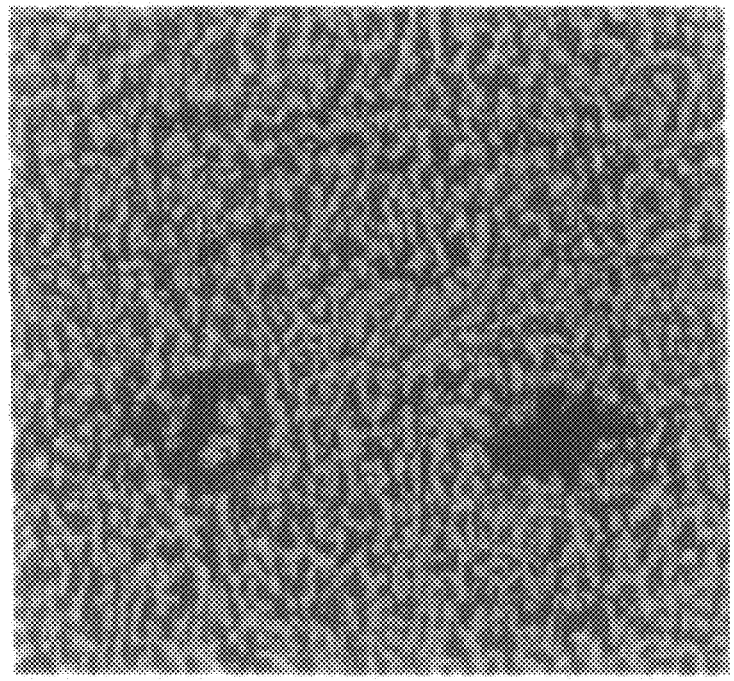

FIGS. 36A-D are photomicrographs illustrating GFP expression and tissue morphology in lungs and tumors of LLC bearing mice following intra-tumoral injection of Ad5PPE-1GFP. Tissue was frozen in OCT and sectioned to 10 µm by cryostat. All pictures were taken in magnification of 25×. FIG. 36A-GFP in angiogenic blood vessels of lung metastases; FIG. 36B—CD31 antibody immunostaining of the section pictured in FIG. 36A; FIG. 36C—GFP expression in blood vessels of primary tumor; FIG. 36D—phase contrast of the section of C illustrating blood vessels.

Figure 37:
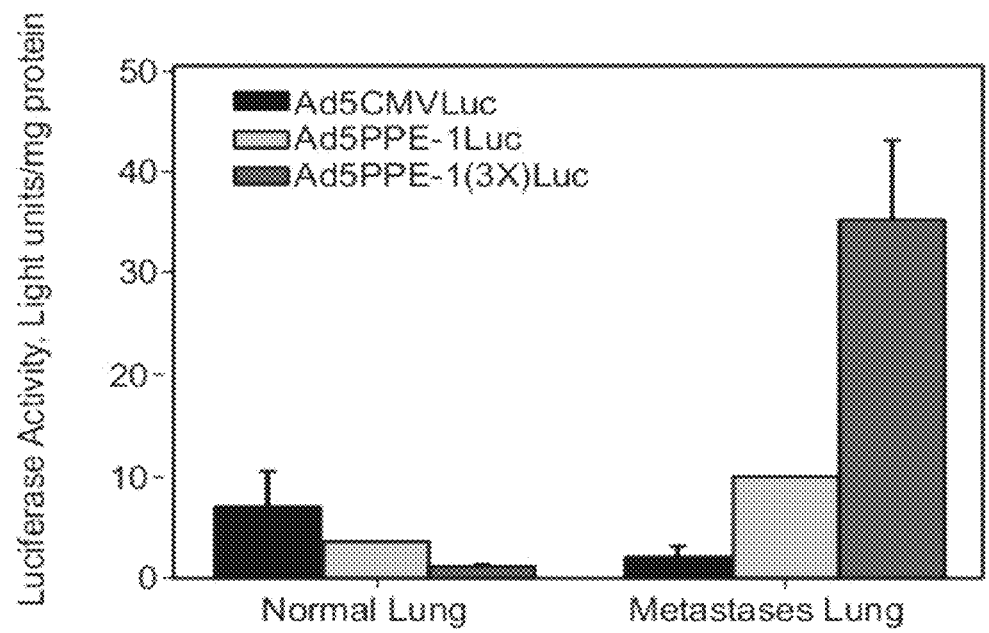

FIG. 37 is a histogram illustrating Luciferase expression in normal lung and metastatic lung of Lewis lung carcinoma-induced mice, injected with Ad5CMVLuc, Ad5PPE-1Luc and Ad5PPE-1-3X-Luc Lewis lung carcinoma was induced by D122-96 cells injected to the foot pad for the metastatic model. Luciferase activity was measured five days post-systemic injection of Ad5CMVLuc (n=7; black bars), Ad5PPE-1Luc (n=6; gray bars), or Ad5PPE-1-3XLuc (n=13; brown bars). Activity is expressed as light units/µg protein.

Figure 38:
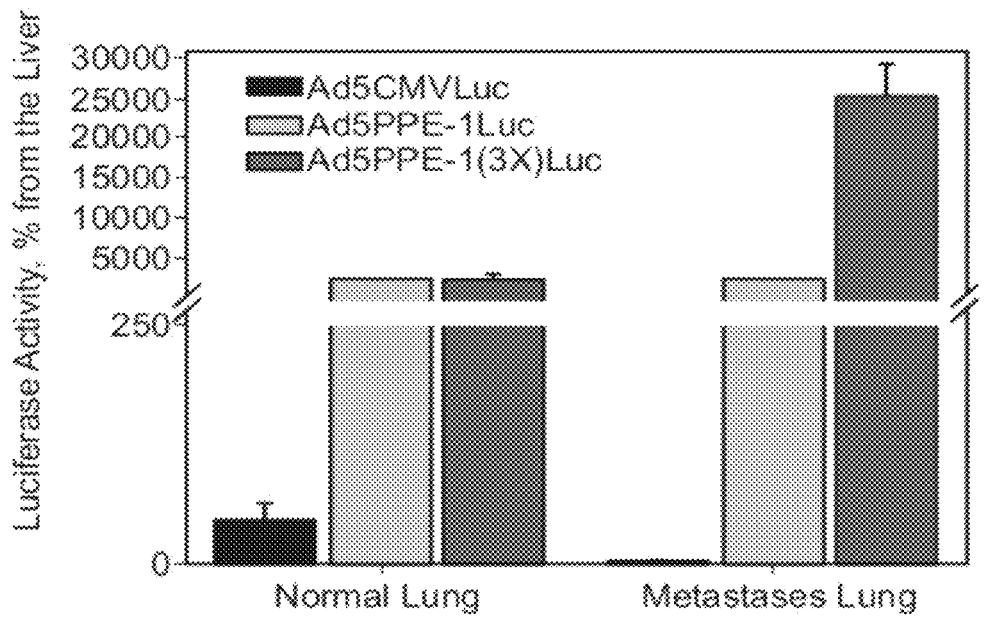

FIG. 38 is a histogram illustrating Luciferase activity as percentage of liver activity (where the liver is 100%), in normal lung and lung metastasis of Lewis lung carcinoma-induced mice injected with Ad5CMV, Ad5PPE-1Luc and Ad5PPE-1(3X).

Figure 39A:
Figure 39B:
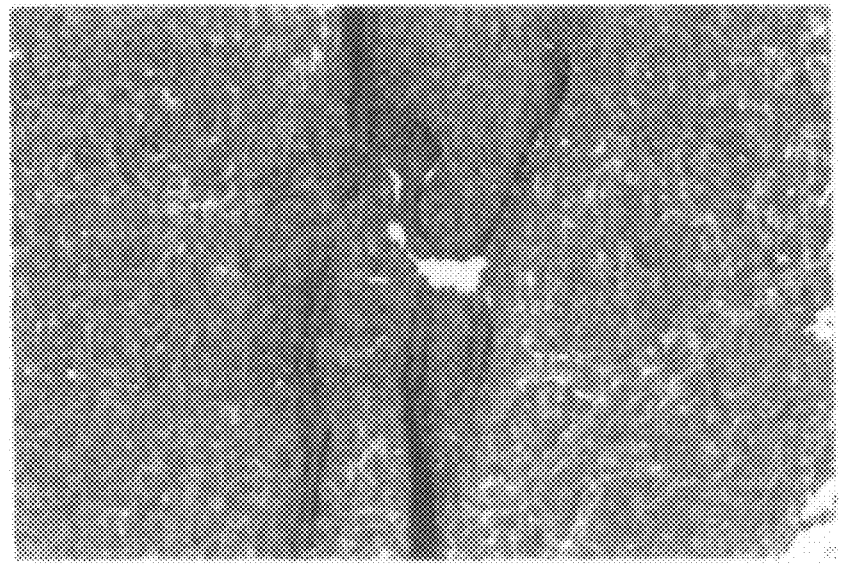

FIGS. 39A-B are photomicrographs illustrating co-localization of GFP expression (FIG. 39A) and CD31 immunostaining (FIG. 39B) in mice with LLC lung metastases injected with Ad5PPE-1-3X-GFP.

Figure 40:
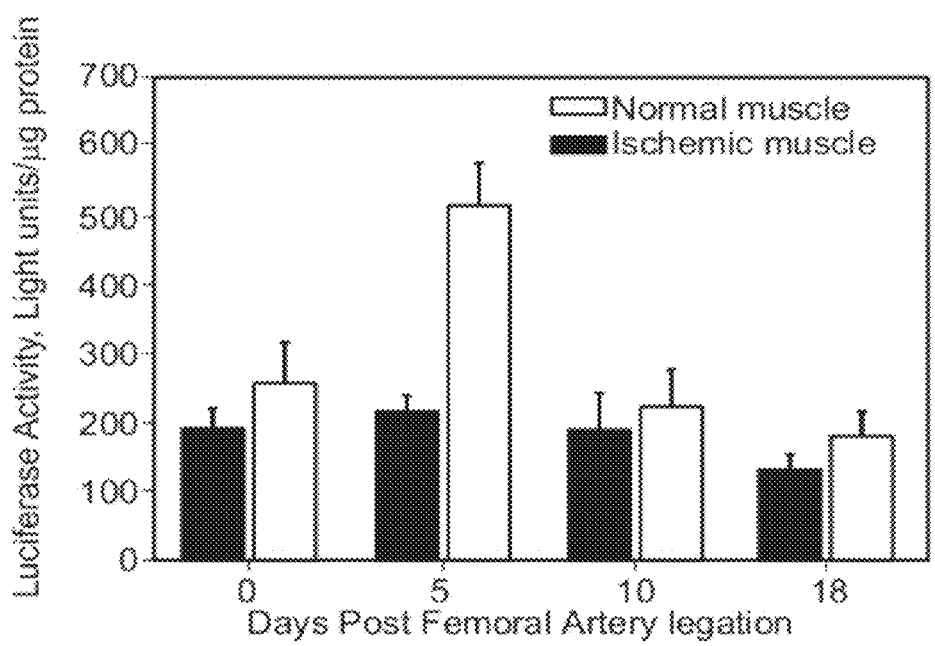

FIG. 40 is a histogram illustrating Luciferase activity (light units/µg protein) in muscles (ischemic and normal) of PPE-1Luciferase transgenic mice at two, five, ten and 18 days post femoral ligation and in control (non-ligated animals—day 0; n=8 for each group).

Figure 41:
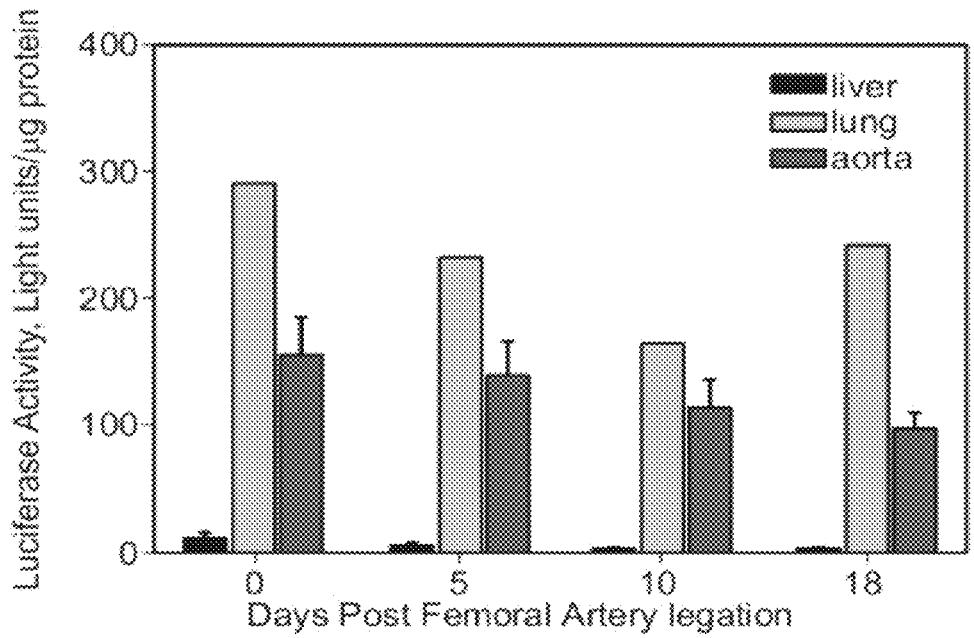

FIG. 41 is a histogram illustrating Luciferase activity (light units/µg protein) in the liver, lung and aorta in muscles (ischemic and normal) of PPE-1Luciferase transgenic mice at five (n=6), ten (n=6) and 18 (n=8) days post femoral ligation and in control (non ligated animals—day 0).

Figure 42:
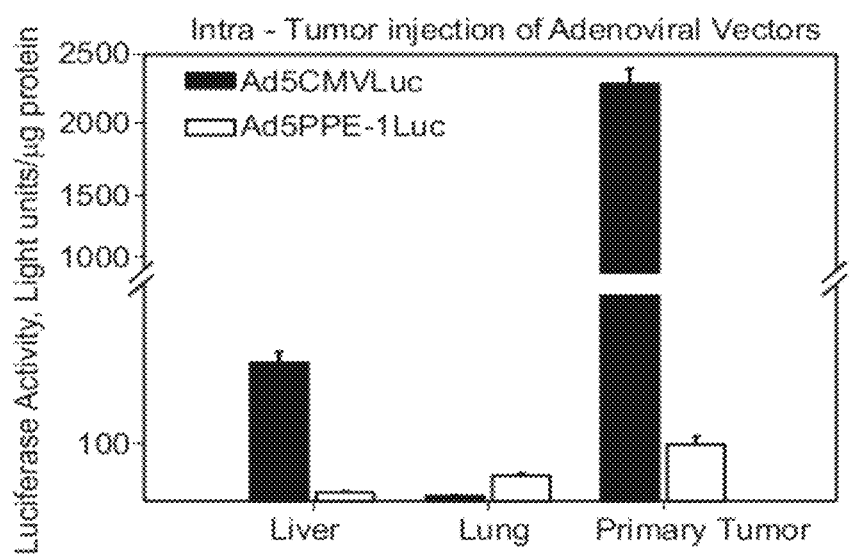

FIG. 42 is a histogram illustrating Luciferase activity, (light units/µg protein detected in the livers, lungs and primary tumors of LLC mice injected in primary tumors with Ad5CMVLuc (black bars) or Ad5PPE-1Luc (open bars).

Figure 43A:
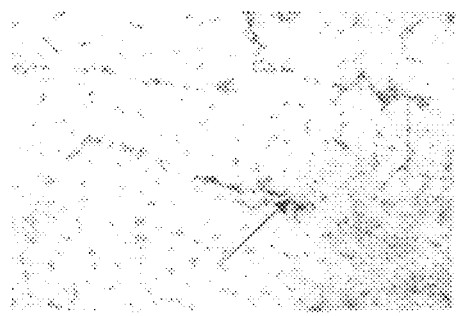
Figure 43C:
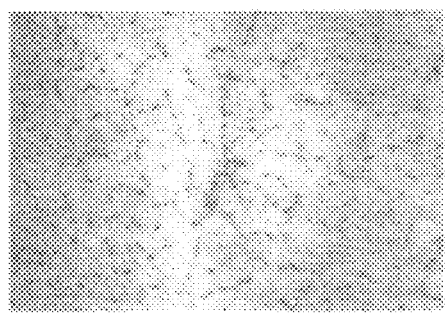
Figure 43B:
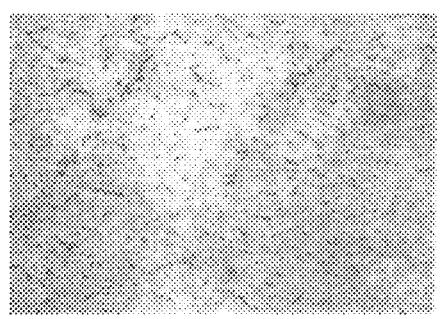
Figure 43D:
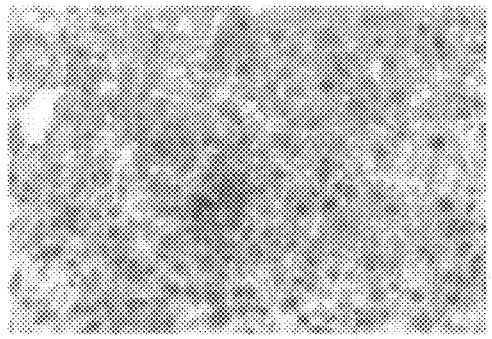
Figure 43E:
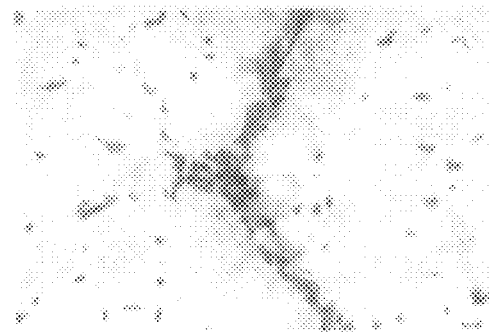
Figure 43F:
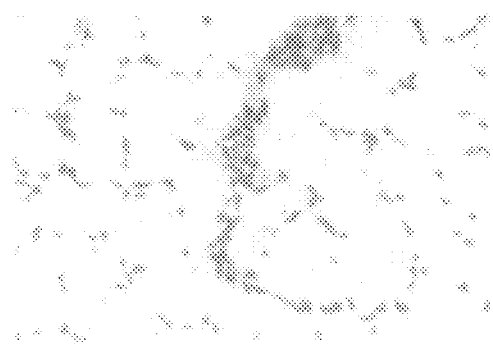
Figure 43G:
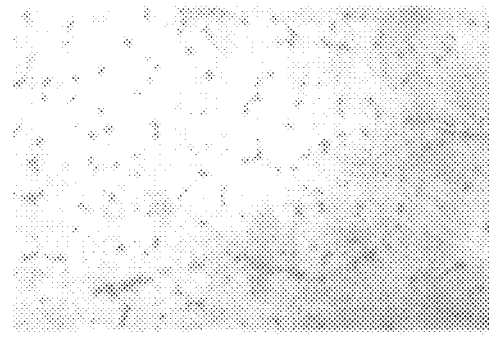
Figure 43H:
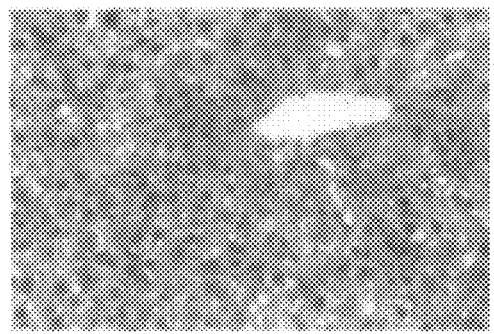

FIGS. 43A-H are in-situ hybridization images illustrating tissue distribution of tissue-specific or constitutive expression of various transgenes. FIGS. 43A-C illustrate in-situ hybridization with a VEGF specific antisense probe on representative ischemic muscles from: A, Ad5PPE-1-3XVEGF treated mouse; B, Ad5CMVVEGF treated mouse; C, saline treated mouse; D, liver section from Ad5CMVVEGF treated mouse. An arrow indicates positively stained cells. FIGS. 43E-G, illustrate in-situ hybridization with a PDGF-B specific antisense probe of representative ischemic muscles from: E, Ad5PPE-1-3XPDGF-B treated mouse; F, Ad5CMVPDGF-B treated mouse; G, saline treated mouse; H, liver section from Ad5CMVPDGF-B treated mouse.

Figure 44A:
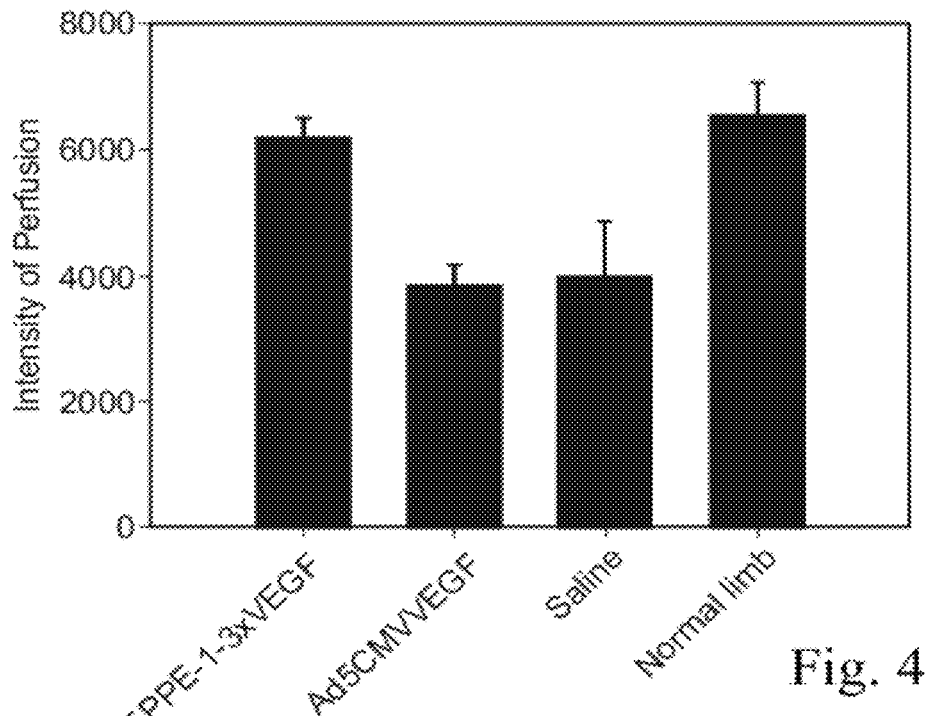
Figure 44B:
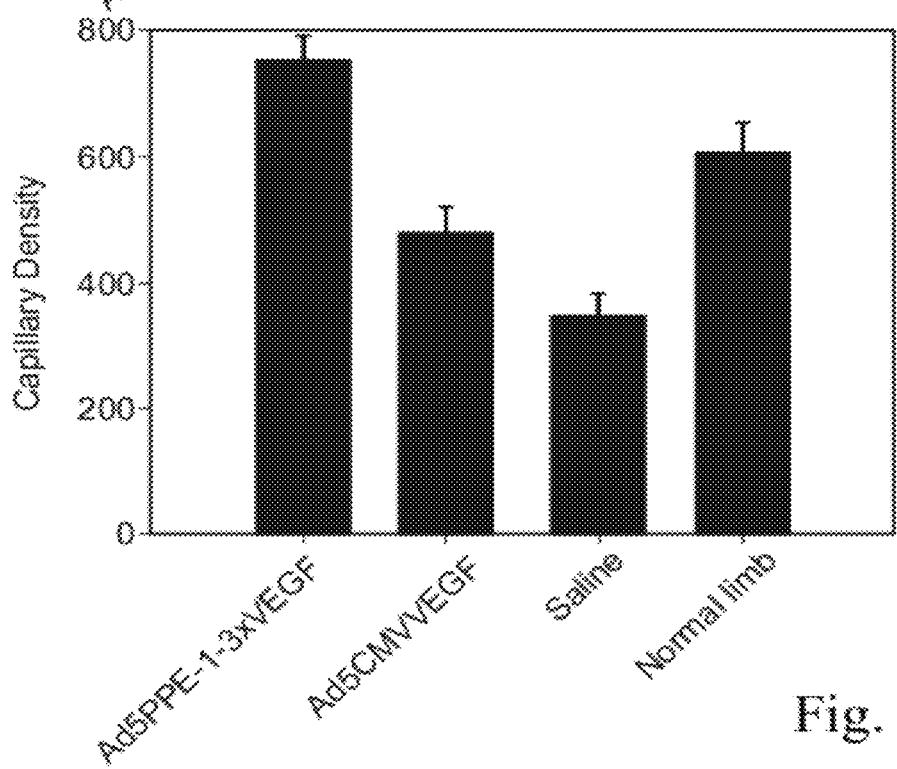

FIGS. 44A-B are histograms illustrating a long-term effect of Ad5PPE-1-3XVEGF or Ad5CMVVEGF on blood perfusion and angiogenesis in mouse ischemic limb. A, mean intensity of signal in the US images of the various treatment groups, 50 days following femoral artery ligation. B, mean capillary density, measured as number of CD31+ cells/mm$^2$ in the various treatment groups, 70 days following femoral artery ligation.

Figure 45A:
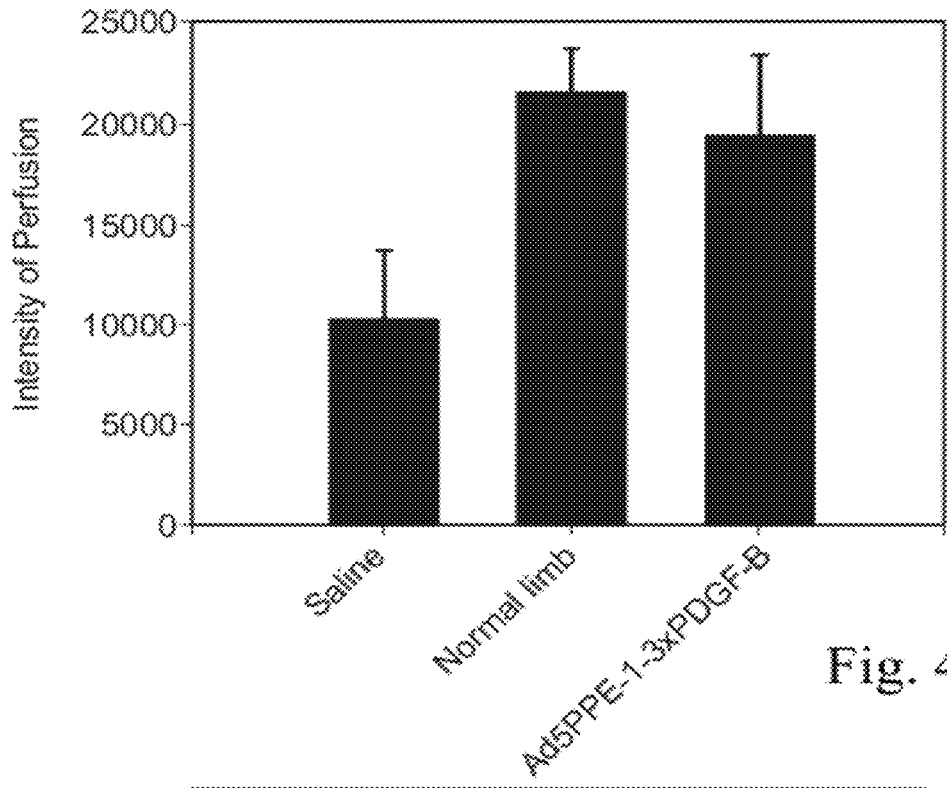
Figure 45B:
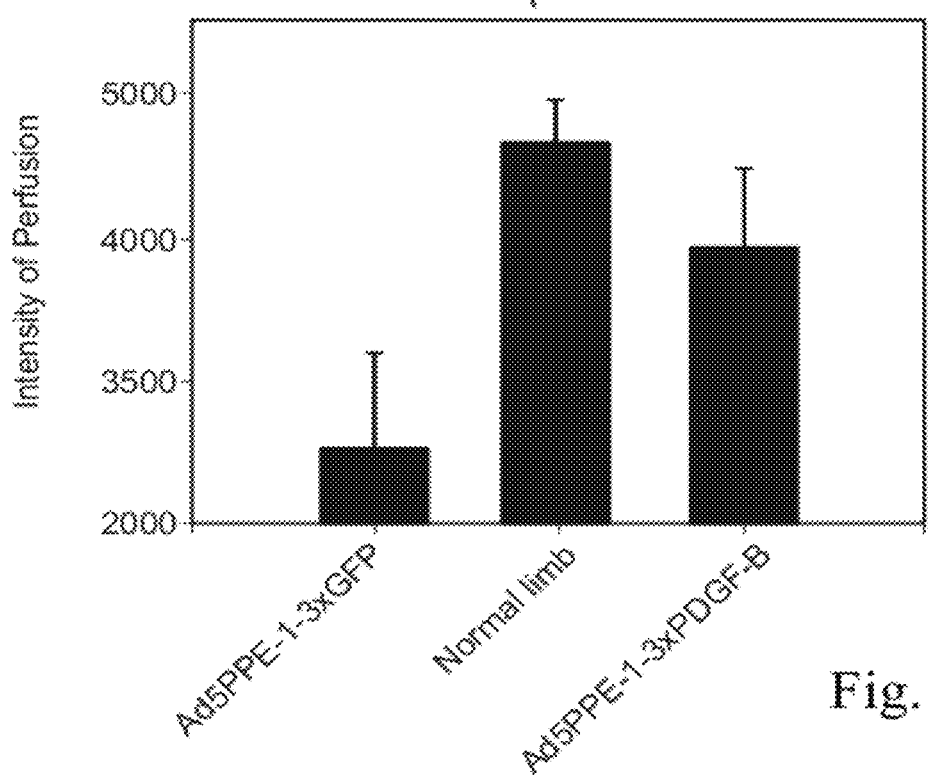
Figure 45C:
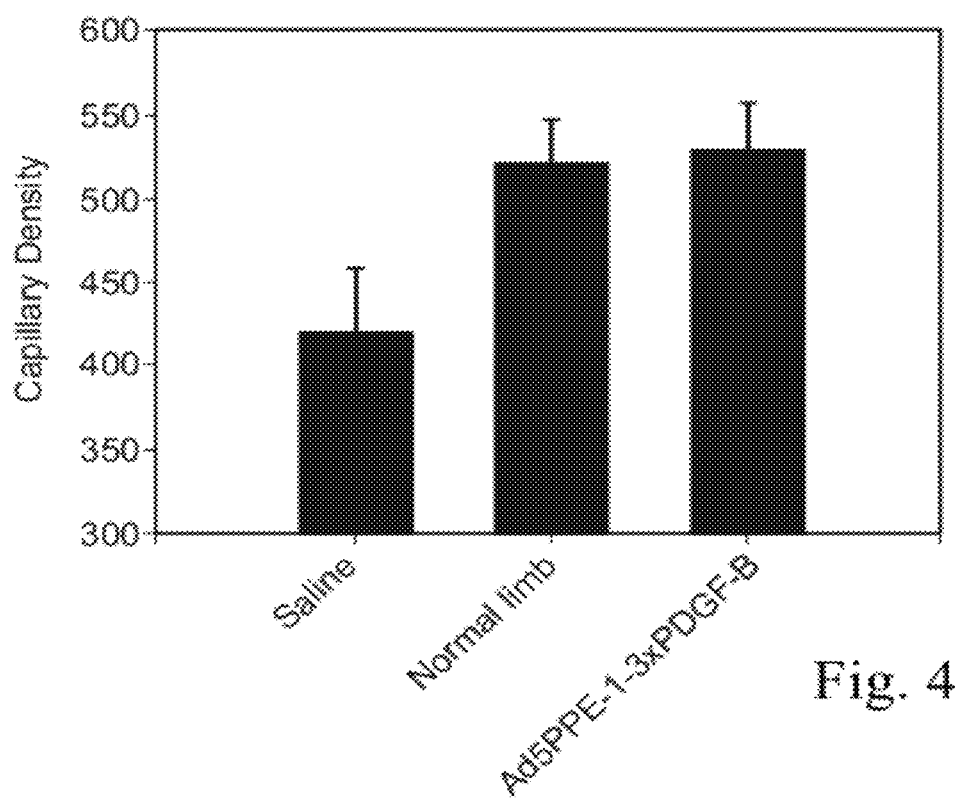
Figure 45D:
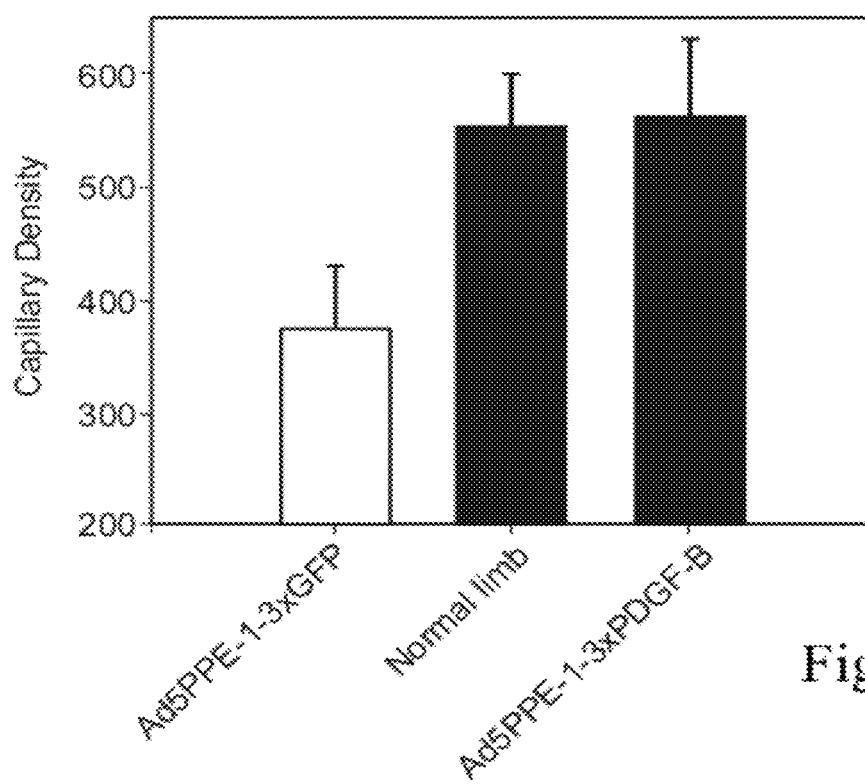

FIGS. 45A-D are histograms showing early and long term effects of Ad5PPE-1-3XPDGF-B on neovascularization in mouse ischemic limb. FIGS. 45A-B—mean perfusion intensity measured by US imaging (45A, 30 days following femoral artery ligation; 45B, 80 days following femoral artery ligation). FIGS. 45C-D—mean capillary density, measured as number of CD31+ cells/mm$^2$ in the various treatment groups (45C, 35 days following femoral artery ligation; 45D, 90 days following femoral artery ligation).

FIGS. 46A-G illustrate long term effects of angiogenic therapy using PDGF-B and VEGF alone or in combination under regulation of an endothelial specific or a constitutive promoter on neovascularization and blood flow in mouse ischemic limb. A, mean intensity of signal in the US images of the various treatment groups, 80 days following femoral artery ligation. B, mean capillary density, measured as number of CD31+ cells/mm$^2$ in the various treatment groups, 90 days following femoral artery ligation. FIGS. 46C-G—smooth muscle cells recruitment to mature vessels in ischemic limb muscles, 90 days following femoral artery ligation. Smooth muscle cells are immunostained with anti-α-SMactin antibodies (in red, X20). C, Ad5PPE-1-3XPDGF-B treated mouse; D, combination therapy treated mouse; E, Ad5PPE-1-3XVEGF treated mouse; F, control, Ad5PPE-1-3XGFP treated mouse; G, normal contralateral limb (note that only large vessels are stained).

Figure 47:
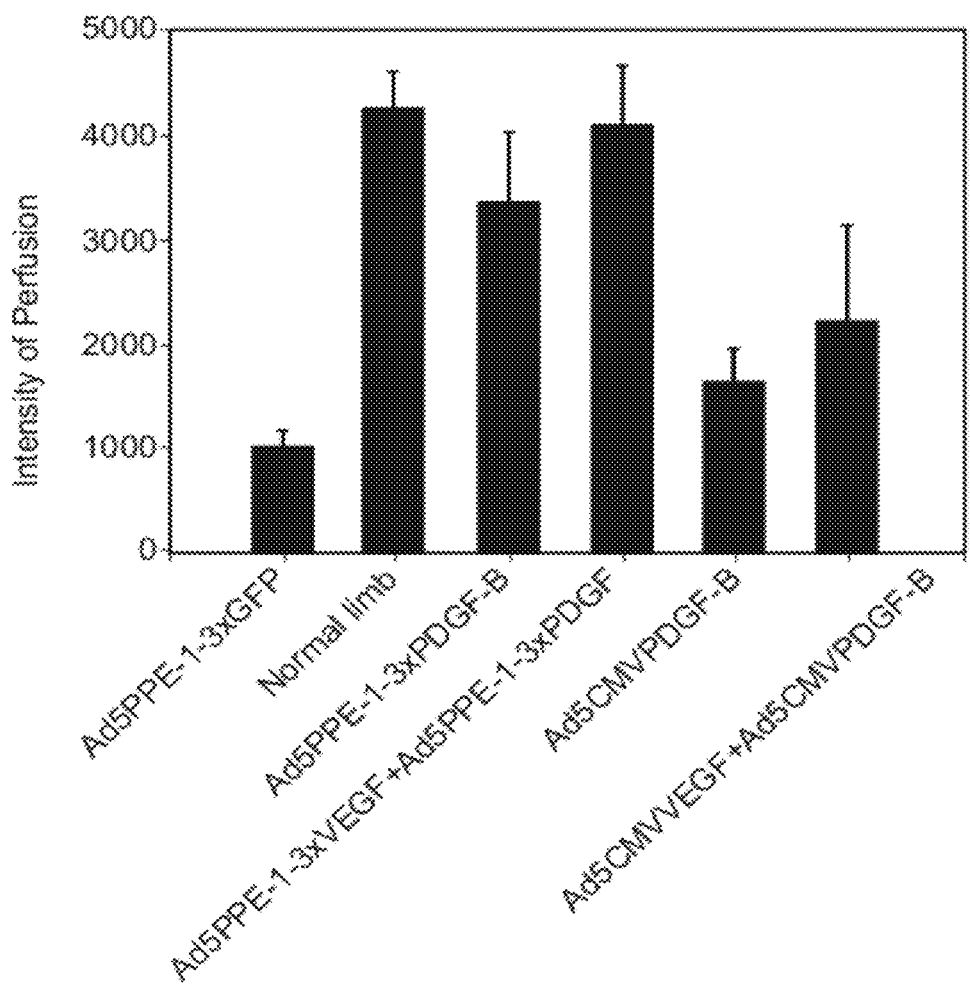

FIG. 47 illustrates the effect of PDGF-B alone or in combination with the proangiogenic factor VEGF on blood perfusion in mouse ischemic limb 50 days following artery ligation.

DESCRIPTION OF THE PREFERRED EMBODIMENTS

The present invention is of an improved endothelial cell-specific promoter which can be employed to reliably direct high-level expression of a sequence of interest to endothelial cells and in particular endothelial cells participating in angiogenesis.

The principles and use of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the examples and drawings. The invention is capable of other embodiments or of being practiced or carried out in various ways. Also, it is to be understood that the phraseology and terminology employed herein is for the purpose of description and should not be regarded as limiting.

Although endothelial specific promoters have been previously described (e.g. U.S. Pat. No. 5,747,340) these promoters have typically been inefficient at directing expression to endothelial cells or have not been demonstrated as being specific to endothelial cells in-vivo.

Enhancer elements specific to endothelial cells have also been described. Bu et al. (J. Biol. Chem. (1997) 272(19): 32613-32622) have demonstrated that three copies (3X) of the 1X enhancer element of PPE-1 (containing elements ETE-C, ETE-D, and ETE-E) endows promoter sequences with endothelial cell specificity in-vitro, however such specificity has not been demonstrated in-vivo.

As is well known in the art, in-vitro experiments cannot reliably predict in-vivo results. As such, the results presented by Bu et al., although suggestive of endothelial cell specificity, do not provide sufficient evidence as to the utility of 3X enhancer element in-vivo.

The lack of in-vivo studies also brings into question the endothelial cell specificity of the 3X enhancer element in whole organisms. Lack of this data implies that therapeutic application of this element is questionable, because when employed in-vivo, and in particular when employed for regulating angiogenesis, it is imperative that expression of an angiogenesis regulator (e.g., cell toxin) be directed specifically to endothelial cells, preferably in a specific subset of endothelial cells which are involved in angiogenesis.

As is illustrated in the examples section which follows, the present inventors, through laborious experimentation, have provided, for the first time, conclusive evidence as to the in-vivo activity of the 3X enhancer element. Such evidence identifies the 3X element and its sequence derivatives (e.g., SEQ ID NO:7) as highly suitable for use in therapeutic applications.

In addition, in reducing the present invention to practice, it was discovered that a novel configuration of the PPE-1 enhancer sequence of the present invention endows promoter sequences with an unexpected and highly specific activity in endothelial cells participating in angiogenesis.

Thus, according to one aspect of the present invention there is provided an isolated polynucleotide functional as an endothelial cell specific promoter in a mammal such as a human being.

The isolated polynucleotide includes an enhancer element including one or more copies of the sequence set forth in SEQ ID NO:6 and preferably one or more copies of the sequence set forth in SEQ ID NO:8, which as is illustrated in the Examples section which follows, plays an important role in regulating expression in endothelial cells participating in angiogenesis.

One specific and novel sequence configuration of an enhancer element utilizable by the present invention is illustrated in SEQ ID NO:7.

For purposes of this specification and the accompanying claims, the term "enhancer" refers to any polynucleotide sequence, which increases the transcriptional efficiency of a promoter.

According to some embodiments of the invention, the isolated polynucleotide includes contiguous copies of SEQ ID Nos:6 and/or 8. Such sequences are preferably positioned in a head-to-tail orientation, although, the enhancer element of the present invention can also include one or more copies of a specific portion of the sequence of SEQ ID NO:6 or 8, in an inverted orientation, e.g., by using sequences complementary to SEQ ID NO:6 or 8 in construction of the enhancer element.

Preferably the isolated polynucleotide further includes an endothelial cell-specific promoter sequence element. For purposes of this specification and the accompanying claims, the term "promoter" refers to any polynucleotide sequence capable of mediating RNA transcription of a downstream sequence of interest. The endothelial specific promoter element may include, for example, at least one copy of the PPE-1 promoter.

Preferably, the isolated polynucleotide further includes a hypoxia response element, for example at least one copy of the sequence set forth in SEQ ID NO: 5.

Thus, according to this aspect of the present invention, an endothelial cell specific promoter which includes various enhancer element configurations is provided.

It will be appreciated that the enhancer element sequences can be positioned within the promoter sequence used, upstream of the promoter, between the promoter and a downstream sequence of interest or within the sequence of interest (e.g., intron).

The isolated nucleic acid sequence of the present invention can be used to regulate gene expression in eukaryotic tissue, and in particular, in proliferating endothelial cells, for example endothelial cells involved in angiogenesis.

Thus, the isolated polynucleotide sequence of the present invention may be provided, in some cases, as part of a nucleic acid construct further including a nucleic acid sequence of interest which is positioned under the regulatory control of the isolated polynucleotide of the present invention. It will be appreciated that such a nucleic acid construct can further include any additional polynucleotide sequences such as for example, sequences encoding selection markers, origin of replication in bacteria, or sequences encoding reporter polypeptides. Such a nucleic acid construct is preferably configured for mammalian cell expression and can be of viral origin. Numerous examples of nucleic acid constructs suitable for mammalian expression are known in the art; the Examples section which follows provides further detail of several such constructs.

For purposes of this specification and the accompanying claims, the phrase "sequence of interest" refers to any polynucleotide sequence that has the capacity to be transcribed by an RNA polymerase. This definition includes coding sequences translatable into polypeptides, as well as sequence for antisense RNA, RNA which binds DNA, ribozymes and other molecular moieties which are not destined to undergo translation. Examples of nucleic acid sequence of interest which may be used by the construct according to the present invention are provided hereinbelow and in the Examples section which follows.

Examples presented hereinbelow illustrate that the improved endothelial cell specific promoters of the present invention can reliably direct expression of a reporter gene to endothelial tissue following systemic in-vivo administration. These examples further show, for the first time, that the isolated polynucleotide of the present invention can be used to preferentially express a reporter protein (GFP) in ischemic and/or angiogenic tissue, thus providing for the first time direct evidence as to the importance of the PPE-1 enhancer element and its derivative in therapeutic applications.

While use of a reporter protein, such as GFP, may have utility in detection of early stages of metastatic tumor growth, especially in animal models, or for non-invasive imaging of metastases (Yang, M. et al., Proc. Nat. Acad. of Sci. (2001) 27:2616-2621) such a use is only a small portion of the projected utility of the claimed invention. It is believed, for example, that AdPPE-1GFP can be used in a combination with AdPPE1tk, AdPPE-1p55 and/or other anti-angiogenic treatments, in order to follow and treat angiogenesis by a relatively non-invasive method.

Replacement of the GFP reporter gene with an apoptosis inducing factor (e.g. p55; GenBank accession M75866) in a construct of, for example AdPPE-1-3X-p55 is predicted to reliably target apoptosis to rapidly proliferating endothelial cells in angiogenic blood vessels of a growing tumor. Because such a vector may be administered systemically, it can be employed to effectively induce apoptosis in developing metastatic foci, without discovering the location of those foci. Such a use represents a significant improvement in comparison to prior art practice. By inducing apoptosis specifically in developing vasculature, it is feasible to eliminate angiogenesis.

An opposite approach may be used to re-vascularize tissue, for example in atherosclerotic patients or in patients that have suffered significant impairment of peripheral circulation as a result of disease or injury. In this case, a construct of the type AdPPE-1-3X-GF, where GF is a growth factor (e.g., cytokine) or modificants thereof (e.g., AdPPE-1-SEQ ID NO:7-GF), can be employed. Suitable growth factors for use in this context include, but are not limited to, VEGF (GenBank accession M95200) and rat PDGF-BB (GenBank accession; 99% identity to mus-AF162784) and EGR-1 (GenBank accession M22326) FGFs (including, but not limited to, GenBank accession XM 003306) and combinations thereof.

It will be appreciated that the use of more than one angiogenic factor may be preferable according to this aspect of the present invention to avoid problems of vessel immaturity and blood vessel regression which have been shown to be associated with administration of VEGF alone (for further details see Example 22 and 26 of the Examples section). Combined therapy can mimic the first stage of endothelial channel sprouting and subsequently recruitment of smooth muscle cells to stable the nascent vessels [Richardson D M et al. (2001) Nat. Biotechnol. 19:1029-1034]. Combined therapy according to this aspect of the present invention may be practiced by cloning the polynucleotides of interest on the same nucleic acid construct each of which being under the regulation of the isolated nucleic acid of the present invention. Alternatively, or preferably, each of the polynucleotides of interest may be separately cloned into the nucleic acid constructs of the present invention, thereby enabling a more tight regulation on the induced angiogenic process.

Incorporation of a hypoxia response element (e.g. SEQ ID NO: 5) within the promoter sequence of the present invention can also be used with the present invention in order to further enhance expression selectivity to ischemic tissues, thus leading to neo-vascularization of selected tissues. As the blood supply improves, ischemia is relieved, the hypoxia response element ceases to be induced, GF levels decline and the neo-vascularization process is halted.

The promoter sequences generated according to the teachings of the present invention are particularly useful in regulating angiogenesis in a tissue. As illustrated in the Examples section which follows, the modified 3X (SEQ. ID. NO:7) containing promoter sequence of the present invention and the unmodified PPE-1 promoter are both expressed in metastatic foci of the LLC model. However example 22 clearly illustrates that the modified 3X sequence is specifically responsible for both a decrease in expression levels of the reporter gene in normal lung and a dramatic increase in expression of the reporter gene in metastatic foci. There is neither a hint nor a suggestion in the prior art that such a result could be achieved. Thus, use of a construct including the 3X element in a gene therapy context can be expected to maximize delivery to tumors while minimizing toxic effects on surrounding normal tissue. Significantly, this is true even if the surrounding tissue contains an endothelial component, as illustrated in FIG. 37. This is because, as demonstrated in Example 11, the 3X sequence greatly increases the level of expression in rapidly proliferating endothelial tissue, even in the context of the PPE-1 promoter.

For example, the p55 gene might be used in conjunction with a promoter of the present invention containing a hypoxia response element in order to specifically induce apoptosis in growing tumors. Such a strategy is deemed feasible because a growing tumor mass tends toward ischemia as tumor growth often exceeds the angiogenic capacity of the surrounding tissue. Other expressible cell toxins which can be used along with the promoter sequence of the present invention in order to specifically reduce a tumor mass include but are not limited to, other pro-apoptotic genes, the Herpes simplex thymidine kinase gene (HSV-tk; included in the pORF-HSV1tk expression vector available from InvivoGen, San Diego, Calif.) angiostatin (Genbank accession number X05199), endostatin (Genbank accession number M33272) and angiostatin-endostatin chimera (included in the pORF-HSV1tk expression vector available from InvivoGen, San Diego, Calif.).

Alternately, or additionally, angiostatin or endostatin genes might be used in conjunction with a promoter of the present invention in order to specifically block angiogenesis without inducing apoptosis.

Thus, according to alternate preferred embodiments, angiogenesis may be stimulated or blocked. This flexibility will allow varied uses of the invention including, but not limited to reduction of tumor mass and re-vascularization of atherosclerotic regions of the heart or neo-vascularization of peripheral tissues with an inadequate blood supply. One relevant clinical scenario is use of a promoter according to the present invention to generate new blood vessels to increase the blood supply in limbs of diabetic patients.

The nucleic acid construct according to the present invention can be administered to a subject (mammals, preferably humans) per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the nucleic acid construct accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

It will be appreciated that the isolated polynucleotide of the present invention has been isolated based on its capacity to promote or enhance transcription in eukaryotic cells of an endothelial lineage. Therefore a mammalian cell transformed with a claimed isolated polynucleotide is an additional embodiment of the invention. Numerous examples of such transformed cells are provided in examples recited herein below.

While the examples provided hereinbelow deal specifically with the use of the 3X sequence in conjunction with the PPE-1 promoter, it is anticipated that the enhancer sequence of the present invention will also exert its cell specific effect when used with other eukaryotic promoter sequences.

Such anticipation is based on prior art findings which show that enhancer elements are often portable, i.e., they can be transferred from one promoter sequence to another, unrelated, promoter sequence and still maintain activity. For examples, see D. Jones et al. (Dev. Biol. (1995) 171(1):60-72); N. S. Yew et al, (Mol. Ther. (2001) 4:75-820) and L. Wu. et al. (Gene Ther. (2001) 8; 1416-26). Indeed, the earlier work of Bu et al. (J. Biol Chem. (1997) 272(19): 32613-32622) strongly suggests that enhancer elements related to those of the present invention, for example enhancers including SEQ ID NO: 6 may be used with constitutive promoters, for example the SV-40 promoter. As such, constructs containing, methods employing and isolated polynucleotides including a eukaryotic promoter modified to include the enhancer sequence of the present invention are well within the scope of the claimed invention.

Thus, it is postulated that a minimal configuration of an enhancer element according to the present invention is an isolated polynucleotide as set forth in SEQ ID NO: 8. This enhancer is anticipated to function with a wide variety of promoters, including but not limited to endothelial specific promoters (e.g. PPE-1; SEQ ID NO.: 1) and constitutive promoters, for example viral promoters such as those derived from CMV and SV-40. This enhancer should be capable of imparting endothelial specificity to a wide variety of promoters. The enhancer element may be augmented, for example by addition of one or more copies of the sequence set forth in SEQ ID NO:6. These additional sequences may be added contiguously or non-contiguously to the sequence of SEQ ID NO.: 8.

The present invention further includes a method of expressing a nucleic acid sequence of interest in endothelial cells employing a construct which relies upon an enhancer element including at least one copy of the sequence set forth in SEQ ID NO:8 and a promoter to direct high level expression of the sequence of interest specifically to endothelial cells.

As used herein "ex-vivo administration to cells removed from a body of a subject and subsequent reintroduction of the cells into the body of the subject" specifically includes use of stem cells as described in (Lyden et al. (2001) Nature Medicine 7:1194-1201).

While adenoviruses are employed in the experiments described in examples presented hereinbelow, the constructs of the present invention could be easily adapted by those of ordinary skill in the art to other viral delivery systems.

The viral vectors, containing the endothelial cell specific promoters, can also be used in combination with other approaches to enhance targeting of the viral vectors. Such approaches include short peptide ligands and/or bispecific or bifunctional molecule or diabodies (Nettelbeck et al. Molecular Therapy 3:882; 2001).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Specifically, experiments conducted in conjunction with the examples recited hereinbelow employed the following methods and materials:

Materials and Methods

Cell Culture

Lewis Lung Carcinoma—(D122-96), Human Embryonic Kidney (293) and HeLa cells were grown in 4.5 gr/1 DMEM, supplemented with 10% fetal calf serum (FCS), 50 U/ml penicillin, 50 µg/ml streptomycine and 2 mM glutamine (Biological industries, Beit-Haemek, Israel). Bovine Aortic Endothelial Cells—BAEC, Normal Skin Fibroblasts—NSF, HepG2 and Human Umbilical Endothelial Cells—HUVEC-304 (ATCC, USA) were grown in 1.0 gr/1 DMEM (Biological industries, Beit-Haemek, Israel), supplemented with 5% FCS, 50 U/ml penicillin, 50 µg/ml streptomycine and 2 mM glutamine. The BAEC cells were supplemented with complete fibroblast growth factor (Sigma, St. Louis, Mo.). RINr1046-38 (RIN-38) were grown in 199 Earle's salts (5.5 mM glucose) medium supplemented with 5% FCS (Biological Industries, Beit-Haemek, Israel), 50 U penicillin/ml, 50 µg streptomycine/ml and 2 mM glutamine.

"HepG2" as used herein refers to ATCC-HB-8065.

"HeLa" as used herein refers to ATCC-CCL-2.

"Human Bronchial Epithelial cells" and "B2B" as used herein refers to ATCC-CRL-9609.

"HUVEC" and "Human Umbilical Vein Endothelial Cells" as used herein refers to ATCC-CRL-1730.

"CHO" and "Chinese Hamster Ovary" as used herein refers to ATCC-61.

Hypoxia Induction

Twenty six hours post transfection or transduction cells were incubated in an isolated chamber which was washed for 30 minutes by a gas flow containing 0.5% $O_2$, 5% $CO_2$, balance by $N_2$. The isolated chamber was placed in humidified 5% $CO_2$, 37° C. incubator.

Luciferase Activity in Cells and Tissues

To assay the PPE-1 promoter activity quantitatively in-vitro and in-vivo, a Luciferase gene expression system kit was employed (Promega Corp., Madison, Wis.). Forty eight hours post transfection or transduction the cells were washed and 200 µl lysis buffer was added for 15 minutes. Cells lysates were collected and centrifuged for 15 minutes (14,000 rpm) at 4° C. Subsequently, 10 µl of the supernatant was added to 50 µl Luciferase assay buffer. The activity was measured in Luminometer over a 20 second period.

To assay Luciferase activity in solid tissue a 20 mg sample was excised and homogenized in 1 ml of the homogenization solution and centrifuged for 15 minutes (14,000 rpm) at 4° C., and 10 ml of the supernatant were assayed for Luciferase activity, as described above. Results were expressed as Luciferase light units per 1 µg protein. Protein was measured using the Bradford assay with bovine serum albumin (BSA) as a standard.

GFP Activity In-Vitro and In-Vivo

To test GFP expression in-vitro, cells were washed twice with PBS and were fixed for 30 minutes with freshly made 4% paraformaldehyde in PBS. Following fixation, examination by fluorescent microscopy was conducted.

In order to test the cellular distribution of the delivered gene in-vivo, tissues were fixed in freshly made 4% paraformaldehyde in 0.1 M phosphate buffer for 6 hours at 4° C., soaked overnight in 30% sucrose at 4° C. and frozen in OCT compound (Sakura, USA). The tissue blocks were sliced by a cryostat at 10 µm thickness and observed directly under fluorescence microscopy (FITC filter).

Proliferating and Quiescent Cells

In order to compare the PPE-1 promoter activity in proliferating and quiescent BAEC, the cells were divided into two groups: 1. proliferating cells—growing and infecting in 10% FCS media. 2. Quiescent cells—growing and infected in serum free media started in 72 hours prior to the transduction. All cells were grown in humidified incubator, 5% $CO_2$, 37° C.

Preparation of Recombinant Replication Deficient Adenoviruses

Several recombinant replication deficient adenoviruses (type 5) were constructed. An expression cassette including the murine preproendothelin-1 (PPE-1) promoter (SEQ ID NO:1) located upstream to the Luciferase gene (originated from pGL2-basic GenBank Accession number X65323) and the SV40 polyA site (originated from pGL2-basic GenBank Accession number X65323) was ligated into the BamHI restriction site of pPAC.plpA (promoter-less construct). The GFP gene (originated from pEGFP, GenBank accession number AAB02572) was ligated to the PPE-1 promoter at the NotI restriction site. The replication deficient recombinant adenoviruses termed Ad5PPE-1Luc or Ad5PPE-1GFP were prepared by co-transfection of pPACPPE-1Luc or Ad5PPE-1GFP with adenovirus plasmid pJM17 as described by Becker, T. C. et al. (Methods Cell biol. 43, Roth M. (ed). New York. Academic Press, 1994, pp. 161-189) followed by harvest of recombinant virions.

Viruses were prepared for large-scale production. The viral stocks were stored at 4° C. at concentration of $10^9$-$10^{12}$ plaque-forming units/ml (pfu/ml). The viruses Ad5CMV-Luc and Ad5CMV-GFP (Quantum biotechnologies, Carlsbad, Canada) containing the cytomegalovirus (CMV) immediate early promoter (GenBank Accession number U47119) were prepared for large scale preparation as described for the PPE-1 viral vectors and were used as a non-tissue specific control.

Modifications of the PPE Promoter

The modified murine PPE-1 promoter was developed by inserting three copies of the positive transcription element discovered by Bu et al (J. Biol Chem. (1997) 272(19): 32613-32622) into the NheI restriction enzyme site located downstream (−286 bp) to the 43 base pairs endogenous positive element (−364 to −320 bp).

The enhancer fragment termed herein "3X" is a triplicate copy of an endogenous sequence element (nucleotide coordinates 407-452 of SEQ ID NO:1) present in the murine PPE-1 promoter. It has been previously shown that induction of PPE-1 promoter activity in vascular endothelial cells depends on the presence of this element Bu et al (J. Biol Chem. (1997) 272(19): 32613-32622). The 3X fragment was synthesized by using two complementary single stranded DNA strands 96 base pares in length (BioTechnology industries; Nes Tziona, Israel), (SEQ ID NO: 2 and 3). The two single stranded DNA fragment were annealed and filled using Klenow fragment (NEB); the resulting double stranded DNA was 145 base pairs long and included Nhe-1 restriction sites (SEQ ID NO: 4).

The 3X fragment was ligated into the murine PPE-1 promoter down stream of endogenous Nhe-1 site using T4 Ligase. The resulting construct was propagated in DH5α compatent cells and a large-scale plasmid preparation was produced using the maxi-prep Qiagene kit.

Additional Plasmids

Wild Type PPE-1 Promoter

The PPE-1-Luciferase cassette (5249 bp) containing 1.4 kb of the murine preproendothelin-1 (PPE-1) promoter, the Luciferase gene with an SV40 polyA signal (GenBank Accession number X 65323) site and the first intron of the murine ET-1 gene is originated from the pEL8 plasmid (8848 bp) used by Harats et al (J. Clin. Inv. (1995) 95: 1335-1344). The PPE-1-Luciferase cassette was extracted from the pEL8 plasmid by using the BamHI restriction enzyme, following by extraction of the DNA fragment from a 1% agarose gel using an extraction kit (Qiagen, Hilden, Germany).

The Promoter-Less pPAC.plpA Plasmid

The promoter-less pPAC.plpA plasmid (7594 bp) containing sequences of the adenovirus type 5 was originated from the pPACCMV.pLpA (8800 bp). The CMV promoter, the multiple cloning site and the SV40 polyadenylation site (1206 bp) were eliminated by NotI restriction enzyme, The fragmented DNA was extracted from 1% agarose gel. The linear plasmid (7594 bp) was filled-in by Klenow fragment and BamHI linker was ligated by rapid DNA ligation kit to both cohesive ends. The linear plasmid was re-ligated by T4 DNA ligase and transformed into DH5α competent cells, in order to amplify the pPAC.plpA with the BamH1 restriction sites. The plasmid was prepared for large-scale preparation and purified by maxi prep DNA purification kit.

pPACPPE-1Luciferase Plasmid

The pPACPPE-1Luciferase plasmid was constructed by inserting the PPE-1-Luciferase cassette into the BamHI restriction site of the pPAC.plpA plasmid, by using T4 DNA ligase. The plasmid was subsequently used to transform DH5α competent cells. The plasmid (12843 bp) was prepared for large-scale preparation and purified by maxi prep DNA purification kit.

pPACPPE-1GFP Plasmid

The pPACPPE-1GFP plasmid was constructed by subcloning the GFP gene (originated from pEGFP, GenBank accession number AAB02572) downstream to the PPE-1 promoter into the NotI restriction site, by T4 DNA ligase.

The plasmid was subsequently used to transform DH5α competent cells. The plasmid (11,801 bp) was prepared for large-scale preparation and purified by maxi prep DNA purification kit.

pACPPE-13X Luciferase and pACPPE-13X GFP Plasmids

The pPACPPE-1-3XLuciferase and pPACPPE-1-3XGFP were constructed by inserting the PPE-1-3XLuc or PPE-1-3XGFP cassette digested by BamHI restriction enzyme from pEL8-3X (FIG. 26B) containing Luc or GFP into the BamHI restriction site of the pPAC.plpA plasmid. pEL8-3X contains the modified murine PPE-1 promoter (1.55 kb) (red)—located between BamHI and NotI that contains the triplicate endothelial specific enhancer 3X (as set forth in SEQ ID NO.: 7) located between two NheI site. The promoter, the Luciferase or GFP gene, the SV40 poly A sites and the first intron of the endothelin-1 gene, all termed the PPE-1 modified promoter cassette was digested and extracted by BamHI restriction enzyme as described in materials and methods. The plasmids (12843 bp) were prepared for large-scale preparation and purified by maxi prep DNA purification kit.

In-vitro experiment, DNA transduction—Cells were plated in 24 or 96 well dishes 24 hours prior to transduction. Subconfluent cells were counted in a sample well. Thereafter, growth media was aspirated from each well, and the indicated viral vectors, at the indicated multiplicity of infection (MOI), were diluted in infection media (DMEM or RPMI 1640, 2% FBS) and added to the monolayers. Cells were incubated for 4 h at room temperature. Subsequently, complete medium was added, and the cells were incubated at 37° C., 5% $CO_2$ for 72 h.

Animals

All animal procedures were approved by the "Animal Care and Use Committee" of Sheba Medical Center, Tel-Hashomer.

Different mouse strains were used:
(i) Male, 3 months old, wild type C57BL/6 mice (Harlan farms, Jerusalem, Israel).
(ii) Male 3 month old BALB/C mice (Harlan farms, Jerusalem, Israel).
(iii) Male and female 6 month old ApoE gene deficient mice hybrids of C57BL/6×SJ129 mice (Plump A S. et al. Cell (1991) 71:343-353).
(iv) Male and female 3 month old over-expressing the Luciferase gene under the control of murine PPE-1 promoter (5.9 Kb), generated by Harats et al. (J. Clin. Inv. (1995) 95: 1335-1344).

All mice were grown in the Lipids and Atherosclerosis Research Institute.

Tissue Gene Expression in Normal Mice

To assay the efficiency and tissue specificity, $10^{10}$ pfu/ml of Ad5PPE1Luc or Ad5CMVLuc (as non-tissue-specific control), were suspended in 100 µl of physiological saline and injected into the tail vein of mice as described hereinabove. Luciferase activity was assayed 1, 5, 14, 30 and 90 days post-injection. To localize cellular distribution of the expressed reporter genes, Ad5PPE-1GFP or Ad5CMVGFP ($10^{10}$ pfu/ml in 100 µl physiological saline) were injected into the tail vein of normal 3 month old, male C57BL/6 mice. GFP expression was detected five days post-injection. All mice appeared healthy and no toxicity or inflammation was noted in the liver or other tissue.

GFP Activity in Tissues

To test the cellular distribution of the delivered gene in-vivo, tissue samples from injected mice were fixed in freshly made 4% paraformaldehyde in 0.1 M phosphate buffer for 6 hours at 4° C., soaked overnight in 30% sucrose at 4° C. and frozen in OCT compound (Sakura, Calif., USA). The tissue blocks were sliced at 10 µm thickness and observed directly under fluorescence microscopy (FITC filter).

Tumor Implantation

Lewis Lung Carcinoma cells (LLC) were harvested with trypsin/EDTA, washed 3 times with PBS and counted with 0.1% trypan blue (Biological industries, Beit-Haemek, Israel) to assess their viability. In order to test the level of activity of the PPE-1 promoter activity in tumor angiogenesis in mice, two different tumor models were used.

In the primary tumor model, the cells ($1×10^6$ cells/ml in 100 µl physiological saline) were subcutaneously injected to the mice backs (n=17). Twenty-one days post injection Ad5PPE-1, Ad5PPE-1GFP, Ad5CMV, or Ad5CMVGFP ($10^{10}$ pfu/ml) were injected into the tumor tissue (IT) or intravenously and their activity was detected as described above.

In the metastatic tumor model, the cells ($5\times10^5$ cells/ml in 50 µl physiological saline) were injected to the mice foot-pad (n=12). When the tumor tissue reached a size of 0.7 mm in diameter, the foot pad (with the primary tumor) was resected under anaesthetic and sterile conditions. Fourteen days post surgery the viruses (Ad5PPE-1, Ad5PPE-1GFP, Ad5CMVLuc or Ad5CMVGFP) were injected to the mouse tail vein.

In both tumor experimental models mice were sacrificed 5 days post viral injection, their tissues were excised and tested for Luciferase or GFP activities.

Wound Healing Model

Male 3 month old C57BL/6 mice were anaesthetized by subcutaneous injection of sodium pentobarbital (6 mg/kg). Their backs were shaved and 5 cm of straight incisions was made. The incisions were immediately sutured by 4/0 sterile silk thread. The angiogenic process in the healing wound was examined every two days by H&E and anti von-Willibrand antibody immuno-histochemistry staining.
Ten days post incisions $10^{10}$ pfu/ml of Ad5PPE-1Luc or Ad5CMVLuc were systemically injected to the tail vein. Five days post injections the mice were sacrificed and Luciferase activity was assayed as described above in the skin of the incision site and in the normal contra lateral site as a control.

Histological examination—In order to evaluate the extent of angiogenesis in tumor and metastasized tissue, the tissues were sliced into 5 µm sections and stained with Haematoxylin and Eosin (H&E). Anti CD31 (rat anti mouse CD31 monoclonal Ab. Phaminogen, N.J., USA) antibodies were used for analyses of neo-vascularization in the tumor models.

Plasmids and adenoviral vectors for VEGF and PDGF-B transgenic expression—Recombinant replication-deficient adenoviruses serotype 5 were constructed as described in Varda-Bloom, N. et al. [Tissue-specific gene therapy directed to tumor angiogenesis. (2001) *Gene Ther* 8, 819-27]. Briefly, pACCMV.pLpA plasmid was modified to include either the cDNA for murine $VEGF_{165}$ (GenBank Accession number M95200) or rat PDGF-B (GenBank Accession number AF162784), under the regulation of the cytomegalovirus (CMV) immediate early promoter. The pACPPE-1-3X plasmids, in which the CMV promoter was replaced by the modified murine preproendothelin-1 (PPE-1-3X) promoter, were constructed with the same cDNA sequences. Each of the plasmids was co-transfected with pJM17 plasmid into HEK293 cells, to generate the various recombinant adenoviruses. The viruses were propagated in HEK293 cells and reduced to a concentration of $10^{10}$ PFUs/ml. Control vectors were generated similarly.

Mouse model of hind limb ischemia and gene therapy—Male and female C57Bl6 mice (Harlan Laboratories Ltd., Israel), at least 12 weeks of age, were maintained in accordance with guidelines of the Animal Care and Use Committee of Sheba Medical Center. Hind limb ischemia was induced based on previously described protocol [Couffinhal, T. et al. Mouse model of angiogenesis. *Am J Pathol* 152, 1667-79. (1998)]. In brief, animals were anesthetized with pentobarbital sodium (40 mg/kg, IP). Following shaving of the limb fur the right femoral artery was ligated, proximal to the bifurcation of the saphenous and popliteal arteries. Five days following ligation, $10^9$ PFUs of the various adenoviral vectors were I.V. administrated.

Ultrasonic imaging—Ultrasonic imaging was performed at 7 days intervals following ligation using Synergy ultrasound system (General Electric, USA) at 7.5 MHz in angiographic mode. Animals were awake and restrained while imaging. Animals were accommodated under conventional conditions for up to 90 days.

Immunohistochemistry—Skeletal muscles from both hind limbs and liver tissue of sacrificed ischemic mice were frozen in OCT compound and cryo-sectioned. Endothelial cells were immunostained using rat monoclonal anti-CD31 antibodies (PharMingen, San Diego, Calif.). Smooth muscle cells were immunostained using mouse polyclonal anti-α-SMactin antibodies (SIGMA, St. Louis, Mo.). Background was stained with hematoxylin.

In-situ hybridization—5 µm skeletal muscle sections were prepared from both hind limbs of ischemic animals. In-situ hybridization with either sense or antisense DIG-labeled probes to $VEGF_{165}$ or PDGF-B was performed, and digoxigenin (DIG) was detected by anti-DIG-AP conjugate (Roche Molecular Biochemicals, Mannheim, Germany). Background was stained with methyl green.

Image processing—Ultrasonic images were processed using the Image-Pro Plus software tools (Media Cybernetics, Silver Spring, Md.). Number of colored pixels indicating the most intensive perfusion was calculated for each image.

Statistical Analysis

Analysis between groups for statistically significant differences was performed with the use of t-test ANOVA, or the Mann-Whitney Rank test. Data are shown as mean±SE.

Example 1

Analysis of 3X-PPE-1 Plasmid Activity In-Vitro

In order to analyze the activity of the PPE-1-3X, a comparison of reporter gene expression in the PPE-1-3X promoter plasmid and the unmodified PPE-1 promoter plasmid was undertaken. Reporter gene plasmids containing either the PPE-1-3X fragment or the unmodified PPE-1 fragment and the reporter gene Luciferase were transfected into endothelial and non-endothelial cell lines as well as to a bronchial epithelium cell line (B2B) which express the PPE-1 promoter (see materials and methods above). The B2B cell line was chosen to provide an indication of the 3X element's capacity to reduce expression in non-endothelial cell lines relative to the PPE-1 promoter. Transfection was accomplished using lipofectamine (Promega Corp., Madison, Wis.). A βgal-neo plasmid was employed as an indicator of the transfection efficiency in each case according to accepted molecular biology practice.

Figure 1:
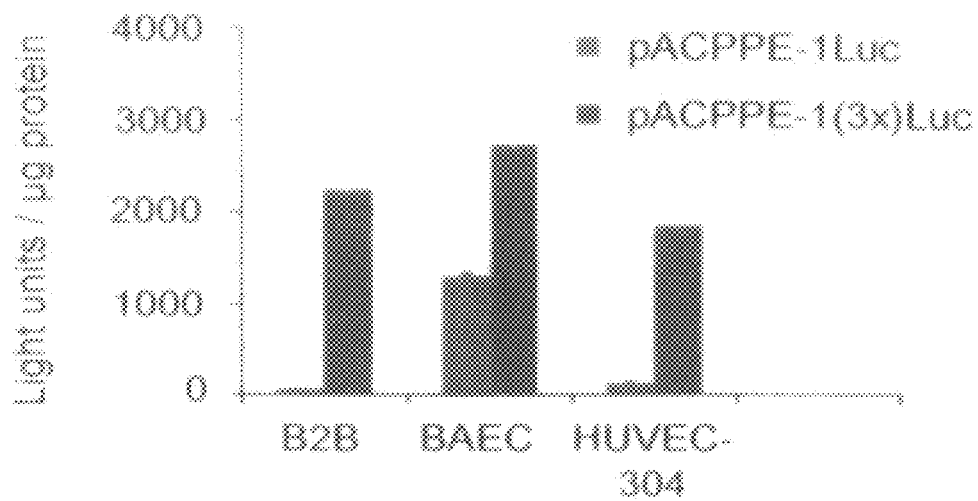

Forty-eight hours post transfection, the cells were harvested using lysis buffer (Promega Corp., Madison, Wis.) and Luciferase activity was analyzed by a luminometer (TD-20e—Turner Designs, Sunnyvale, Calif.). In parallel, βgal activity was analyzed in order to standardize for different transformation efficiencies. The results are summarized in FIG. 1 and Table 1. Luciferase activity under the control of PPE-3X is 15-20 times higher than Luciferase activity under the control of the unmodified PPE-1. In non-endothelial cell lines minimal expression was detected using both the PPE-1 and PPE-1-3X. This demonstrates that PPE-3X is a promising candidate for delivery of a gene specifically into endothelial cells in-vivo.

TABLE 1

Luciferase activity in cells transfected with
PPE-1 and PPE-1-3X Luciferase constructs

| Plasmid | Luciferase activity in: endothelial cell lines | | non endothelial cell lines |
| --- | --- | --- | --- |
| | HUVAC | BAEC | RIN |
| PPE-1 | 135.12 | 1121.3 | 0.73 |
| PPE-1-3X | 768 | 18331.7 | 0.32 |

Example 2

Activity and Specificity of Ad5PPE-1/Luciferase In-Vitro

The PPE-1/Luciferase, PPE-1-3X/Luciferase, PPE-1/GFP and PPE-1-3X/GFP were also ligated into the Ad5 plasmid to produce Ad5PPE-1/Luc and Ad5PPE-1-3X/luc, Ad5PPE-1/GFP and Ad5PPE-1-3X/GFP (Varda-Bloom et al., (2001) Gene therapy 8:819-827). These constructs were assayed separately as detailed hereinbelow.

In order to test the activity of the Ad5PPE-1/luc, transfections of B2B (Human bronchial epithelial), BAEC (Bovine Aortic Endothelial Cells) and HUVEC (Human Umbilical Vein Endothelial Cells) were undertaken. These three cell lines express the endothelin gene and were chosen to indicate levels of expression of the tested construct in an endothelial cell. The RIN (Rat Insulinoma) cell line, which does not express endothelin, was employed as a negative control and transfected with the same construct. Ad5CMVLuc (Luciferase under the control of CMV promoter) was used as non-endothelial-specific control in all cell lines.

Figure 2:
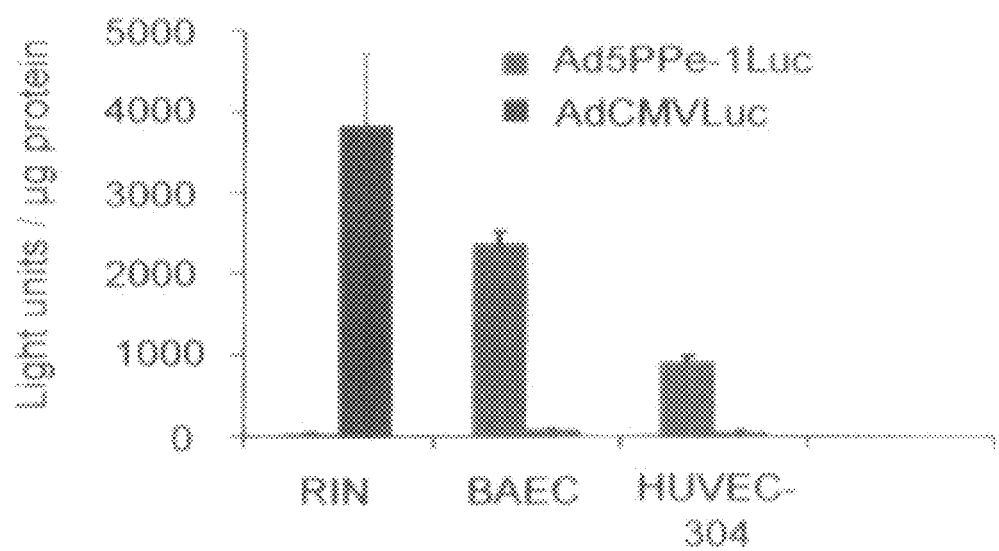

FIG. 2 clearly illustrates that higher Luciferase expression was achieved in endothelial BAEC and HUVEC cell lines with the PPE-1 promoter than with the CMV promoter. In the RIN cells, which are not of endothelial origin, the CMV promoter produced more Luciferase activity than the PPE-1 promoter. These results demonstrate the endothelial specificity of the un-modified PPE-1 promoter.

Example 3

Activity and Specificity of Ad5PPE-3XLuc and Ad5PPE-3XGFP

The Ad5PPE-3X/Luciferase and Ad5PPE-3X/GFP constructs were used to transfect the cell lines described hereinabove in Example 2 in order to ascertain the impact of the 3X element on specificity and expression levels. As in example 2, Ad5CMVLuc was used as a non-endothelial-specific control. Higher Luciferase expression in BAEC and HUVEC cell lines was detected under the control of the PPE-3X promoter as compared to the CMV promoter.

FIG. 3A is a photomicrograph illustrating GFP expression under the control of Ad5PPE-1-3X in the BAEC cell line. FIG. 3B is a photomicrograph illustrating GFP expression of Ad5CMV in the BAEC line. As is clearly shown by these Figures, the PPE-1-3X promoter is more active in endothelial cells. These results clearly indicate that the 3X element does not detract from the endothelial specificity of the PPE-1 promoter. Relative activities of the PPE-1 and PPE-1-3X promoters in cell culture are presented in example 6 hereinbelow.

Example 4

In-Vitro Assay of Pro-Apoptotic Activity of the p55 Gene

Following sub cloning of P55 (TNFR1, GenBank accession number M75866) into PACPPE3X (containing the PPE-1-3X promoter), and into PACCMV, co-transfection of these plasmids and GFP (pEGFP-C1 vector; CLONTECH, Palo Alto, Calif.). was performed as described hereinabove. Briefly, the gene was subcloned downstream to the PPE-1 promoter (instead of the luciferase gene) into the NotI restriction site, by T4 DNA ligase, following by transforming it into DH5α competent cells. Twenty four hours post-transfection, small and rounded apoptotic cells were visually discernible from normal cells. Electron microscopy of cells transfected with the pro-apoptotic plasmids showed typical appearance of apoptosis, confirming the visual evaluation.

Under the control of the PPE-1-3X promoter, apoptosis was induced by p55 only in endothelial cells (FIG. 4), whereas the CMV promoter did not show any cell specific activity. Luciferase under the control of PPE-1-3X did not induce apoptosis in any tested cell lines. These results indicate that by employing the PPE-1-3X promoter, it is feasible to induce apoptosis specifically in endothelial cells.

Example 5

Hypoxia Responsive Element (HRE) can Enhance Target Gene Expression in Hypoxic Sensitive Endothelial Cells Hypoxia is an important regulator of blood vessels' tone and structure. It has also been shown to be a potent stimulus of angiogenesis (in both ischemic heart diseases and cancer (Semenza, G. L. et al. (2000) Adv Exp Med Biol.; 475:123-30; Williams, K. J. (2001) Breast Cancer Res. 2001: 3; 328-31 and Shimo, T. (2001) Cancer Lett. 174; 57-64). Further, hypoxia has been reported to regulate the expression of many genes including erythropoietin, VEGF, glycolytic enzymes and ET-1. These genes are controlled by a common oxygen-sensing pathway, an inducible transcription complex termed hypoxia inducible factor-1 (HIF-1). The HIF-1 complex mediates transcriptional responses to hypoxia by binding the cis acting hypoxia responsive element (HRE) of target genes. The HRE is a conserved sequence located in the promoters of few genes that respond to hypoxia including: VEGF, Nitric Oxide Syntase-2, erytropoietin and others including endothelin-1, ET-1. The ET-1 promoter contains an inverted hypoxia response element at position −118 bp upstream of the transcription start site, the element contain 7 base pairs and is located between the GATA-2 and AP1 sites 5' GCACGTT 3'-50 base-pairs. (SEQ ID NO: 5.)

The preproendothelin-1 (PPE-1) promoter contains an hypoxia responsive element (HRE) that has the potential to increase its expression in the hypoxic microenvironment of tumor or ischemic tissues, thus making it "tumoral tissue specific" and/or "ischemic tissue specific". In order evaluate the actual function of this HRE, assays of the PPE-1 promoter and PPE-1-3X promoter in conjunction with a Luciferase or GFP reporter gene and delivered by an adenoviral vector were undertaken.

Luciferase activity under the control of the PPE-1 promoter or the PPE-1-3X promoter was compared in BAEC cells under normoxic and hypoxic conditions (0.5% $O_2$ for 16 h). The Luciferase activity under the control of PPE-1 promoter was 5 times higher when exposed to hypoxia (FIGS. 5 and 6). Further, the Luciferase activity under the control of PPE-1-3X promoter was 2.5 times higher under hypoxic conditions. In summary, introduction of the 3X element into the PPE 1 promoter is till capable of increasing expression levels of a downstream gene in response to hypoxia, even though the normoxic levels of expression with the PPE-1-3X gene are higher than those observed with the unmodified PPE-1 promoter.

Example 6

Further Evaluation of PPE-1-3X and PPE-1 Promoter Activity in Endothelial Cell Lines FIG. 7 summarizes the results from B2B, HUVEC and BAEC transfection experiments using pPPE-1/Luciferase and pPPE-1-3X/Luciferase. Higher Luciferase expression (30, 8.5 and 1.5 times more) was observed under the control of the PPE-1-3X promoter than under the PPE-1 promoter in B2B, HUVEC and BAEC, respectively. These results confirm those presented hereinabove and serve to establish that PPE-1-3X is well suited to directing high level expression specifically to endothelial cells. In the context of future in-vivo delivery, the higher levels of expression achieved with the PPE-1-3X construct translate into administration of smaller amounts of DNA. This, in turn, will serve to increase specificity even further.

Example 7

Efficiency, Specificity and Stability of Ad5PPE-1Luc In-Vivo

In order to confirm that the endothelial specificity of expression observed in examples 2 through 6 was not an artifact of cell culture, the Ad5PPE-1/Luciferase construct was injected into C57BL/6 mice as described hereinabove in "Tissue gene expression in normal mice". As in the in-vitro studies, Ad5CMV/Luciferase was employed as a negative control.

Following injection of adenoviral vectors, the specific activity and stability of Luciferase in vascularized and non-vascularized tissues was assayed. Results are summarized in FIG. 8 (Luciferase expression relative to expression in liver) and Table 2 (Luciferase expression as a percentage of total expression in the body). As expected, in Ad5CMV/Luciferase treated mice most of the Luciferase activity (>80% of the total body expression) was found in the liver. Luciferase activity controlled by the PPE-1 promoter was lower in the liver (37-54% of the total body expression). The PPE-1 derived expression was much higher in the aorta (23-33% of the total body expression 5 and 14 days post injection, respectively), compared to Ad5CMV/Luciferase. Treated mice (up to 1.8% of total body expression; Table 2). These results confirm the endothelial specificity observed in cell culture. It should be remembered that the liver is a highly vascularized organ. Therefore examination of cellular expression within organs was undertaken, as detailed hereinbelow.

TABLE 2

Luciferase expression in organs 5 and 14 days post injection of PPE-1 and CMV based constructs

| | Day post injection | | | |
|---|---|---|---|---|
| | 5 Light units/μg protein | | 14 Light units/μg protein | |
| Organ | PPE-1 | CMV | PPE-1 | CMV |
| Aorta | 13.0 ± 2.9 (32.7%) | 1.4 ± 0.5 (0.56%) | 10.6 ± 2.4 (12.6%) | 1.3 ± 0.3 (1.1%) |

TABLE 2-continued

Luciferase expression in organs 5 and 14 days post injection of PPE-1 and CMV based constructs

| | Day post injection | | | |
|---|---|---|---|---|
| | 5 Light units/μg protein | | 14 Light units/μg protein | |
| Organ | PPE-1 | CMV | PPE-1 | CMV |
| Heart | 0.2 ± 0.1 (0.5%) | 1 ± 0.6 (0.4%) | 1.5 ± 0.3 (1.7%) | 1.8 ± 0.6 (1.6%) |
| liver | 22.7 ± 4.5 (57%) | 219 ± 111.5 (88.6%) | 34.9 ± 7.8 (41.6%) | 52.8 ± 10.6 (46.8%) |
| lung | 0.2 ± 0.1 (0.5%) | 2.3 ± 1.0 (0.9%) | 3.6 ± 0.8 (4.3%) | 2.0 ± 0.9 (1.8%) |
| muscle | 0.3 ± 0.1 (0.7%) | 0.8 ± 0.2 (0.3%) | 1.2 ± 0.3 (1.4%) | 1.5 ± 0.5 (1.3%) |
| spleen | 1.3 ± 0.8 (3.2%) | 1.6 ± 0.9 (0.6%) | 2.0 ± 0.4 (2.4%) | 2.3 ± 0.9 (2.0%) |
| pancreas | 2 ± 0.6 (5.0%) | 20.1 ± 6.8 (8.1%) | 26.4 ± 5.9 (31.5%) | 45.2 ± 24.5 (40.1%) |
| kidney | 0.1 ± 0 (0.25%) | 0.9 ± 0.6 (0.4%) | 0.6 ± 0.1 (0.71%) | 0.8 ± 0.3 (0.7%) |

FIGS. 30A and 30 B demonstrate the absolute Luciferase activity (light units/μg protein) in the aortas (A) and livers (B) of the 110 injected mice. Luciferase activity was measured 1 (n=13), 5 (n=34), 14 (n=32), 30 (n=20) and 90 (n=11) days post injection. The results in the aorta represent the promoters (PPE-1 or CMV) activity mostly in endothelial cells, while the results in the livers represent their activity mostly in hepatocytes.

Example 8

Assays of Efficiency, Specificity and Stability of Ad5PPE-1 In-Vivo—in BALB/C Mice The experiments of example 7 were repeated in 12 week old BALB/C mice (n=10 for each group) in order to demonstrate that the observed results were not an artifact of a particular strain of animals.

Because Absolute results with the adenoviral vectors were lower in BALB/C mice than in C57BL/6 mice, the Luciferase expression is expressed as percentage of the total Luciferase activity in all tissues.

The highest relative Luciferase expression 5 days post injection was observed in the spleens of Ad5PPE-1 (90.9%), and in the livers of Ad5CMV (86.2%) injected mice. A significant increase in the relative Luciferase activity in the aortas of Ad5PPE-1 injected mice 14 days post injection (32.9%), compared to its activity five days post injection (1.75%) was also observed (FIGS. 31A and 31B; Ad5PPE-1Luc—open bars; Ad5CMVLuc-black bars).

These results confirm that regardless of mouse strain, the tissue specificity of the PPE-1 promoter is sufficiently strong to effectively eliminate hepatocyte expression, despite preferential uptake of injected DNA by hepatocytes.

Example 9

Cellular Localization of Gene Delivered by Ad5PPE-1 In-Vivo

In order to ascertain cellular expression sites of the gene expressed by PPE-1 in-vivo, Green Fluorescent Protein (GFP) delivered by the adenoviral vector Ad5PPE-1-GFP was used. Ad5CMVGFP (Quantum, Canada) was used as non-endothelial-cell-specific negative control. Five days post-intravenous injection the mice were sacrificed and their tissues were analyzed by fluorescent microscopy.

In the mice injected with Ad5CMVGFP vector, most of the expression was detected in the hepatocytes, and no expression was detected in endothelial cell in the liver (FIG. 9A). In sharp contrast, Ad5PPE-1-GFP injected mice (FIG. 9B), showed no expression in hepatocytes, but significant expression in endothelial cells in the blood vessels of the liver. Similar results were obtained in other tissues where practically all the PPE-1 derived expression was detected in the endothelium, while none of the CMV derived expression was endothelial. These results indicate endothelial specificity is preserved even within an organ containing endothelial and non-endothelial cells. This finding has important implications for prevention of angiogenesis in growing tumors.

Example 10

Assays of Efficiency and Endothelial Specificity of Ad5PPE-1-3X Luc and Ad5PPE-1-3X GFP In-Vitro In order to determine the relative efficacy of Ad5PPE-1 and Ad5PPE-1-3X in driving expression of the reporter genes Luciferase and green fluorescent protein (GFP) in cells, specific activity in endothelial cells was tested in-vitro using cell lines described hereinabove. Ad5CMVLuc and Ad5CMVGFP were employed as non-tissue specific controls. Ad5PPE-1Luc and Ad5PPE-1GFP were employed to ascertain the relative change in expression level caused by addition of the 3X sequence.

Results, summarized in FIGS. 10 and 11, indicate that Luciferase activities under the control of the PPE-1-3X promoter were 5-10 times higher in EC lines (Bovine Aortic Endothelial Cells—BAEC) compared to activity in non-endothelial cells—Rat Insulinoma—RIN, HeLA, HePG2 and normal skin fibroblasts (NSF) (FIGS. 10 and 11).

FIG. 10 shows Luciferase activity as light units/μg protein in B2B, BAEC and RIN cells transduced by Ad5PPE-1Luc, Ad5PPE-1-3XLuc, and Ad5CMVLuc Highest Luciferase expression was observed in RIN cells transduced by Ad5CMVLuc, however this construct was poorly expressed in BAEC and B2B cells. The next highest level of Luciferase expression was observed in BAEC cells transduced by Ad5PPE-1-3XLuc. Ad5PPE-1Luc was expressed at lower levels in BAEC cells. In the B2B cell line Ad5PPE-1Luc and Ad5PPE-1-3XLuc were expressed at nearly identical levels.

Overall, Luciferase activity in the endothelial cell lines under the control of PPE-1-3X promoter was 23 times higher than under the control of PPE-1 promoter and 23-47 times higher than under the control of the CMV promoter at the same infection conditions (moi=10). This is despite the fact that Luciferase expression in non-endothelial RIN cells was 3000 times higher under the control of the CMV promoter (FIG. 10).

In order to establish that PPE-1 and PPE-1-3X are inactive in other non-endothelial cell lineages HeLA, HepG2, NSF cell lines were transduced. BAEC was employed as an endothelial control. FIG. 11 shows Luciferase activity as light units/μg protein in HeLa, HepG2, NSF and BAEC cells transduced by Ad5PPE-1Luc, Ad5PPE-1-3XLuc and Ad5CMVLuc. Transduction with Ad5CMVLuc caused high levels of Luciferase expression in HeLA, HepG2 and NSF cells. These cell lines failed to express Luciferase under the control of PPE-1 and expressed Luciferase at low levels with the PPE-1-3X promoter. As expected, BAEC cells transduced with Ad5PPE-1Luc or Ad5PPE-1-3XLuc exhibited high Luciferase expression.

Taken together these results indicate that introduction of the 3X sequence into the PPE-1 promoter caused higher levels of expression in endothelial cell lines while preventing unwanted expression in non-endothelial cells.

Addition of the 3X sequence to the PPE-1 promoter also increased levels of Green fluorescent protein expression in EC lines (Bovine Aortic Endothelial Cells—BAEC) as indicated in FIGS. 12 A-C which depicts GFP expression in BAEC transduced by moi=1. No expression of GFP was observed using a CMV promoter in this experiment.

In FIG. 12, panel A indicates Ad5PPE-1-3XGFP transduced cells, panel B indicates Ad5PPE-1GFP transduced cells and panel C indicates Ad5CMVGFP. Again, introduction of the 3X sequence into the PPE-1 promoter significantly increased expression of the reporter gene. This result indicates that the ability of the 3X sequence to function as an endothelial specific enhancer is not a function of the downstream gene being transcribed.

Moreover, Ad5PPE-1-3X-GFP and Ad5PPE-1GFP transduction resulted in no GFP expression in non-endothelial cells SMC, HeLa, HePG2 and normal skin fibroblasts (NSF) compared to the high expression under the CMV promoter as summarized in FIGS. 13-16.

FIG. 13 shows GFP expression in SMC transduced by moi=1 of either Ad5PPE-1-3XGFP (panel A) or Ad5CMVGFP (panel B). While high level GFP expression resulted from Ad5CMVGFP transduction, no GFP expression resulted from transduction with Ad5PPE-1-3XGFP transduction.

FIG. 14 shows results of a similar experiment conducted in HeLa cells. As in the previous Figure, panel A indicates cells transduced with Ad5PPE-1-3XGFP and panel B indicates cells transduced with Ad5CMVGFP. Again, while high level GFP expression resulted from Ad5CMVGFP transduction, no GFP expression resulted from transduction with Ad5PPE-1-3XGFP transduction.

FIG. 15 shows results of a similar experiment conducted in HepG2 cells. As in the previous Figure, panel A indicates cells transduced with Ad5PPE-1(3X) GFP and panel B indicates cells transduced with Ad5CMVGFP. Again, while high level GFP expression resulted from Ad5CMVGFP transduction, no GFP expression resulted from transduction with Ad5PPE-1-3XGFP.

FIG. 16 shows results of a similar experiment conducted in NSF cells. As in the previous figure, panel A indicates cells transduced with Ad5PPE-1-3XGFP and panel B indicates cells transduced with Ad5CMVGFP. Again, while high level GFP expression resulted from Ad5CMVGFP transduction, very low GFP expression resulted from transduction with Ad5PPE-1-3XGFP.

These results, taken together, indicate a high level of endothelial specificity and a high level of endothelial expression is obtained by using a modified PPE-1 promoter containing the 3X sequence of SEQ ID NO.: 7.

Example 11

Cellular Localization of a Reporter Gene Delivered by Ad5PPE-1-3X In-Vivo

In order to determine the cellular localization pattern of a reporter gene expressed under the control of the PPE-1-3X promoter in-vivo, Ad5PPE-1-3XGFP and Ad5PPE-1GFP were injected into mice as described hereinabove. Five days post-intravenous injection, the mice were sacrificed and their tissues were analyzed by a fluorescent microscopy.

Significantly higher GFP activity was observed in the endothelial cells of the liver, kidney and spleen blood vessels of Ad5PPE-1-3XGFP injected mice compared to the Ad5PPE-1GFP injected mice. FIGS. 17 A-B show representative results.

FIG. 17A shows low level GFP expression in endothelial cells lining a blood vessel of a mouse injected with the Ad5PPE-1GFP. FIG. 17B shows the much higher level of GFP expression resulting from addition of the 3X sequence to the construct.

Despite the high expression in the lining of the blood vessels, no expression was detected in the hepatocytes, glomerulii, epithelial cells and splenocytes (FIGS. 18 and 19).

FIG. 18 shows representative results from kidney tissue of injected mice. Ad5CMVGFP injected mice (FIG. 18A), Ad5PPE-1GFP (FIG. 18b) and Ad5PPE-1-3XGFP (FIG. 18C) injected mice all exhibited low GFP activity in kidney cells. In FIG. 18B, slightly higher GFP expression is visible in the blood vessel wall (indicated by arrow).

FIG. 19 shows representative results from spleen tissue of injected mice. Ad5CMVGFP injected mice (FIG. 19A), Ad5PPE-1GFP injected mice (FIG. 19B) and Ad5PPE-1-3XGFP injected mice (FIG. 19 C) all exhibited low level GFP activity in cells of the spleen. Higher GFP activity is visible in the blood vessels of Ad5PPE-1-3XGFP injected mice (indicated by arrow).

These results confirmed that both the PPE-1 and the PPE-1-3X promoter are endothelial cell specific in-vivo. They further suggest that activity of both promoters was limited in non-proliferating endothelial tissue (i.e. blood vessels of healthy organs. Therefore, assays in a tumor angiogenic model were undertaken.

Example 12

Assays of the Ad5PPE-1 Construct in Tumor Neovascularization In-Vivo

In order to ascertain the ability of AD5PPE to specifically direct expression of a reporter gene to angiogenic blood vessels in a tumor, the murine LLC model (described hereinabove in materials and methods) was employed.
In a one experiment, Luciferase expression in tumor neovascularization was tested five days post systemic injections of Ad5PPE-1Luc or Ad5CMVLuc ($10^{10}$ pfu/ml each).

In this experiment, systemic injection of Ad5CMVLuc to both primary and metastatic tumor models resulted in minimal expression in the primary tumor or in the metastatic lung. This level of expression was similar to the minimal expression of Luciferase directed by CMV in naive normal lungs (FIG. 35; black bars; n=12). In sharp contrast, under the control of PPE-1 promoter (FIG. 35; open bars; n=9), the highly angiogenic lung metastases were associated Luciferase activity which was about 200 times higher than the Luciferase activity in the poorly-vascularized primary tumor and the naive lungs.

The Luciferase expression in non-metastatic tissues such as the liver, kidney, heart and pancreas was minimal. The expression level in the aorta was about 30% of the levels in the metastatic lungs.

In an additional experiment in the LLC model Ad5PPE-1GFP and Ad5CMVGFP constructs were employed to localize reporter gene expression in the primary tumor and metastatic lungs.

Ad5PPE-1GFP injected mice, showed high levels of GFP specific expression in the blood vessels of the primary tumor (FIG. 36C), although no expression was detected in the tumor cells themselves. This observation is consistent with the results of the LLC cell culture model presented in example 20. In lung metastases, high levels of GFP expression were detected in both big arteries and small angiogenic vessels of the metastatic foci (FIG. 36A). No expression was detected in the normal lung tissue. The endothelial cell localization was demonstrated by co-localization of the GFP expression (FIG. 16A) and the CD31 antibody immunostaining (FIG. 16B). In striking contrast, in Ad5CMVGFP injected mice, no GFP activity was detectable in both the primary tumor and lung metastasis.

FIG. 36C illustrates GFP expression in blood vessels of a primary tumor following intra tumoral injection of Ad5PPE-1GFP. FIG. 36D is a phase contrast image of the same filed as panel C illustrating the tumor and its blood vessels.

These results indicate that while PPE-1 does not drive high level expression in tumor cells per se, the promoter does drive high level expression in vascular endothelia within the tumor, especially in rapidly proliferating angiogenic vessels.

Intra-tumor injection of Ad5CMV into primary subcutaneous tumor model resulted in high Luciferase expression in the tumor tissue and moderately levels of expression liver (10% of the amount expressed in the tumor; FIG. 42). No expression was detected in the metastatic lungs. On the other hand, when injected intra-tumoral, Luciferase expression under the control PPE-1 promoter resulted in similar Luciferase levels of expression in the primary tumor and the metastatic lungs and no expression was detected in the liver.

Example 13

Assays of the Ad5PPE-1 Construct in a Carcinoma Cell Culture System

In order to assay the efficiency of Ad5PPE-1 and Ad5CMV to drive Luciferase expression in cancerous cells, the D122-96 Lewis Lung Carcinoma cell line was employed.

In-vitro transduction at varying multiplicities of infection (moi) was performed. The results indicate that both adenoviral vectors are able to transduced the Luciferase gene to these cells (Table 3). Nevertheless, Luciferase activity directed by the PPE-1 promoter was much lower in the LLC cells than the activity detected in endothelial cells, 50 vs. 1000-2500 light units/μg protein, respectively.

TABLE 3

In-vitro transduction of Lewis lung carcinoma cell line (D122-96) with Ad5PPE-1Luc and Ad5CMVLuc.

|  | MOI = 1 | MOI = 5 | MOI = 10 |
| --- | --- | --- | --- |
| Ad5PPE-1 | 8.1 ± 0.06 | 33.95 ± 7.0 | 50.7 ± 5.0 |
| Ad5CMV | 9.3 ± 1.1 | 47.3 ± 4.0 | 88.13 ± 10.1 |

Example 14

Assay of the Effect of the 3X Sequence in Tumor Angiogenic Blood Vessels In-Vivo In order to ascertain the effect of the 3X sequence on the PPE-1 promoter in angiogenic blood vessels, the Lewis Lung Carcinoma (LLC) metastases model (described hereinabove in material and methods) was employed. Five days post IV injection of $10^{10}$ infectious units of Ad5PPE-1GFP, Ad5PPE-1-3XGFP or Ad5CMVGFP, the mice were sacrificed and their tissues were analyzed as described in material and methods.

FIGS. 20 A-D summarize the GFP expression in metastatic lungs of control mice injected with Saline (FIG. 20A), mice injected with Ad5CMVGFP (FIG. 20 B), mice injected with Ad5PPE-1GFP (FIG. 20 C) and mice injected with Ad5PPE-1-3XGFP (FIG. 20D). Anti-CD31 immunostaining (FIGS. 20C' to 20D') confirm the location of the GFP expression in each metastatic tissue. The results show that while no GFP expression was detected in control—saline injected mice (FIG. 20A), there was a slight expression around the epithelial bronchi of the CMV injected mice, but not in the angiogenic blood vessels of the metastatic lung of these mice (FIG. 20B). Low GFP expression was observed in metastatic lungs of Ad5PPE-1GFP injected mice (FIGS. 20C and 20C'), while high and specific expression was observed in the new blood vessels of Ad5PPE-1-3XGFP injected mice (FIGS. 20D and 20 D').

These results explain the apparent disparity between the in-vivo results of example 10 and the in-vitro results of examples 2, 3 and 6. Both the PPE-1 and the PPE-1-3X promoter are endothelial specific. However, the 3X sequence greatly increases the level of expression in rapidly proliferating endothelial tissue, such as newly forming blood vessels in a growing tumor.

Example 15

Effect of the 3X Element on the PPE-1 Promoter in Tumor Angiogenic Blood Vessels In order to study the effect of the 3X element of the present invention on efficacy and specific activity of the PPE-1 promoter in tumor angiogenic blood vessels, the LLC metastases model was employed. Five days post i.v. injection of $10^{10}$ pfu/ml of Ad5PPE-1Luc, Ad5PPE-1-3XLuc, Ad5CMVLuc, Ad5PPE-1GFP, Ad5PPE-1-3X-GFP or Ad5CMVGFP, the mice were sacrificed and their tissues were analyzed for Luciferase or GFP expression as described hereinabove.

FIG. 37 is a histogram comparing Luciferase expression in normal lungs versus that in metastatic lungs following systemic injection of Ad5PPE-1-3Xluc, Ad5PPE-1Luc or Ad5CMVLuc. Experimental groups were Ad5CMVLuc (n=7; black bars), Ad5PPE-1Luc (n=6; gray bars) and Ad5PPE-1-3XLuc (n=13; brown bars). Activity is expressed as light units/µg protein.

Luciferase expression under the control of the PPE-1-3X promoter was 35 fold greater in the metastatic lungs relative to its activity in normal lungs and 3.5 fold higher than expression driven by the PPE-1 promoter without the 3X element (p<0.001). Very low Luciferase activity was detected in other tissues of mice injected with Ad5PPE-1-3XLuc. Calculating the Luciferase expression in the lungs as percentage from the liver of each injected animal revealed that the activity increased 10 fold in the metastatic lung compared to the activity in normal lung (FIG. 38).

In order to localize reporter gene expression to specific cell types, GFP constructs were employed. FIG. 39 A-B show the GFP expression (FIG. 39A) in metastatic lungs of Ad5PPE-1-3XGFP injected mice. Immunostaining by CD31 antibody (FIG. 39B) confirm the location of the GFP expression in the new blood vessels. No GFP expression was detected in control—saline injected mice. Low level expression around the epithelial bronchi of the CMV injected mice, but not in the angiogenic blood vessels of the metastatic lung. In summary, these results indicate that large increases in expression level resulted from introduction of a 3X element into Ad5PPE-1 constructs and that this increased expression was specific to the angiogenic blood vessels of tumors. Potentially, the observed effect may be coupled with the hypoxia response described hereinabove to further boost expression levels of a sequence of interest.

Example 16

Further Characterization of the PPE-1 Hypoxia Response

In order to further characterize the effect of hypoxia on the murine PPE-1 promoter activity, bovine aortic endothelial cells (BAEC) were transfected by a DNA plasmid (pEL8; FIG. 26A). The pEL8 plasmid contains the murine PPE-1 promoter (1.4 kb) (red), the luciferase gene (1842 bp), the SV40 poly A sites and the first intron of the endothelin-1 gene, all termed the PPE-1 promoter cassette was digested and extracted by BamHI restriction enzyme as described in material and methods. Following transfection, cells were subjected to hypoxic conditions.

Luciferase expression in transfected BAEC subjected to 18 hours of hypoxia (0.5% O2) was eight times higher than Luciferase expression in cells grown in a normoxic environment (FIG. 21). FIG. 21 shows that Luciferase activity (light units/µg protein) in BAEC transfected by a plasmid containing the murine PPE-1 promoter was significantly higher when transfected cells were incubated in a hypoxic environment. Equivalent transfection efficiencies were confirmed by co-transfection with a β-galactosidase reporter vector and assays of LacZ activity.

In order to determine whether murine PPE-1 promoter delivered by adenoviral vector is also up-regulated by hypoxia, BAEC were transduced by Ad5PPE-1Luc. Ad5CMVLuc was used a non specific control in this experiment. Results are summarized in FIG. 22. Hypoxia Luciferase activity in BAEC transduced by Ad5PPE-1Luc. In stark contrast, no significant difference between normoxia and hypoxia was detected in the Ad5CMV transduced cells (FIG. 22).

To understand whether the enhancement of the PPE-1 promoter activity is specific to endothelial cells, different cell lines (BAEC, B2B, CHO, RIN and Cardiac Myocytes) were transduced by Ad5PPE-1 (moi=10) and were subjected to hypoxia (0.5% O2) or normoxia environment. Results are summarized in FIG. 23. Luciferase expression was slightly increased in B2B cells and significantly increased in BAEC cells cultured in a hypoxic environment. Luciferase expression in other cell lines was reduced by the hypoxic environment, compared to normoxia. These results confirm that hypoxic induction of the PPE-1 promoter occurs primarily in endothelial cell lineages.

Example 17

Effect of the 3X Sequence on the PPE-1 Hypoxia Response

In order to ascertain the effect of the 3X sequence on the PPE-1 hypoxia response, BAEC were transduced by Ad5PPE-1Luc and Ad5PPE-1(3X) Luc. Following transduction, the BAEC cells were incubated either in a hypoxic or a normoxic environment as detailed hereinabove. Results are summarized in FIG. 24. Luciferase expression using the Ad5PPE-1Luc construct significantly increased (seven folds)

in response to hypoxia (2578 in hypoxia and 322.1 in normoxia). In contrast, the Ad5PPE-1(3X) Luc construct exhibited only 1.5 fold increase in response to hypoxia (from 2874.5 in normoxia to 4315 in hypoxia conditions). These results indicate that the high normoxic level of expression observed when the 3X sequence is added to the PPE-1 promoter serves to mask the hypoxic response to some extent.

Example 18

Assays of the PPE-1 Response to Hypoxia in a Transgenic Mouse Model

In order to examine the murine PPE-1 promoter activity in tissues subjected to regional hypoxia/ischemia, mPPE-1-Luc transgenic mice, described hereinabove in materials and methods, were employed. The mice were induced to regional hind limb ischemia as previously described (Couffinhal T. et al. (1998) Am. J. Pathol. 152; 1667-1679). In brief, animals were anesthetized with pentobarbital sodium (40 mg/kg, IP). Unilateral ischemia of the hind limb was induced by ligation of the right femoral artery, approx. 2 mm proximal to the bifurcation of the saphenous and popliteal arteries. To verify the induction of functional change in perfusion, ultrasonic imaging was performed on days 4 and 14 by Synergy ultrasound system (GE) equipped with a 7.5 MHz transducer and angiographic software Animals were housed under conventional conditions for up to 18 days.

Luciferase expression was assayed 2, 5, 10 and 18 days post ligation in the ischemic muscle, in the normal non-ligated muscle, in the liver, lung, and aorta.

Results, summarized in FIG. 25, show that while no significant difference was detected in the liver, lung and aorta during the days post ligation, Luciferase gene expression increased following the femoral ligation in both in the normal non-ligated and in the ischemic muscle. While peak Luciferase expression in the ischemic muscle was detected five days post ligation, peak Luciferase expression in the non-ligated muscle was detected ten days post femoral artery ligation. This indicates that the hypoxic response of the PPE-1 promoter is functional in an in-vivo system. Luciferase expression in the non-ischemic muscle did not change during the days tested, compared to its expression in the control non-operated tissue (day=0). In contrast, Luciferase expression in the ischemic muscle was significantly higher on day 5 than at other time points.

On day 5, PPE-1 driven expression of Luciferase was 2.5 times higher than in control non-operated mice and compared to the ischemic muscle in days 10 and 18 (FIG. 40).

Expression of Luciferase in other non-ischemic tissues including liver, lungs and aorta of the transgenic mice subjected to regional ischemia revealed no significant changes within 18 days post ischemic induction in the Luciferase expression in these tissues (FIG. 41).

Further, these results confirm that Luciferase expression was higher in tissues containing a high percentage of endothelial tissue (lung and aorta) than in those tissues containing a low percentage of endothelial tissue (liver and non-ischemic muscle).

Example 19

Effect of Level of Cellular Proliferation on Ad5PPE-1Luc Activity in Endothelial Cells In order to ascertain the effect of level of cellular proliferation on efficiency and specific activity of Ad5PPE-1Luc, an angiogenic model of endothelial cells (BAEC), was tested in-vitro. Transduced BAEC were either induced to quiescence by serum deprivation or grown in 10% FCS for normal proliferation. Briefly, cells were transduced for 48 hours either as quiescent cells—72 hours post serum deprivation or as proliferating cells—in normal media (10% FCS). Luciferase activity is expressed as light unit/μg protein, to normalize for the difference in cell amount. The results presented are an average of triplicate test from four representative independent experiments.

Luciferase expression under the control of PPE-1 promoter (open bars; FIG. 28) was 4 times higher in normal proliferating BAEC than in quiescent cells, and 25 times higher in normal proliferating BAEC than Luciferase expression under control of the CMV promoter (Black bars; FIG. 28). Further, in proliferating cells, the activity under the control of PPE-1 promoter was 10 times higher than that under the CMV promoter control.

In order to simulate angiogenic conditions in-vitro, Ad5PPE-1Luc activity was tested in BAEC induced to rapid proliferation by addition of 40 ng/ml vascular endothelial growth factor (VEGF). Activity under these conditions was compared activity in normal proliferating cells and quiescent cells as described hereinabove. Luciferase expression in BAEC induced to cell proliferation with VEGF was 44 times higher than in normal proliferating cells, and 83 times higher than in quiescent cells (FIG. 29).

Together, these experiments indicate that the level of activity of a sequence of interest under transcriptional control of the PPE-1 Promoter is a function of the level of cellular proliferation, with rapid proliferation causing higher levels of expression.

Example 20

Assays of the PPE-1 Promoter in Atherosclerosis Induced Mice

In order to test the efficiency and specificity of the Ad5PPE-1 vector in atherosclerotic blood vessels, $10^{10}$ pfu/ml of the viral vectors were systemically injected to 6 month old ApoE deficient mice (Plump, A. S. et al. Cell; 1991; 71:343-353).

As ApoE deficient mice age, they develop high cholesterol values and extensive atherogenic plaques with no induction of lipid reach diet. FIG. 32 is a picture of an aorta dissected from an ApoE deficient mouse colored by Sudan—IV. Note that the thoracic aorta contains less red stained atherosclerotic lesions while the abdominal region is highly atherosclerotic. (FIG. 32 adapted from Imaging of Aortic atherosclerotic lesions by 125I-HDL and 125I-BSA. A. Shaish et al, Pathobiology—submitted for publication).

FIG. 33 summarizes Luciferase expression observed 5 days post systemic injections of Ad5PPE-1Luc (open bars; n=12) and Ad5CMVLuc (black bars; n=12) to ApoE deficient mice. Results are presented as absolute Luciferase expression in the thoracic area that contains less atherosclerotic lesion, and the abdominal aorta that is rich atherosclerotic lesion.

Luciferase expression controlled by the PPE-1 promoter was 6 fold higher in the highly atherosclerotic abdominal, and 1.6 fold higher in the slightly atherosclerotic thoracic aorta as compared to expression under the control CMV promoter.

No significant difference was observed between the two aorta regions in the Ad5PPE-1Luc injected mice, while higher Luciferase expression was observed in thoracic aorta of the Ad5CMVLuc injected group compared to low expression in the abdominal aorta that contain lesion.

These results indicate that while a constitutive promoter (CMV) has a tendency to shut down in areas where atherosclerosis is most severe, the PPE-1 promoter is relatively unaffected by disease progression.

Example 21

Assays of the PPE-1 Promoter in a Wound Healing Model

In order to test the Ad5PPE-1 constructs efficiency and specific activity in directing Luciferase expression to healing wound blood vessels, a murine wound healing as described hereinabove in Material and Methods was employed.

As in other experiments, Ad5CMVLuc was used as a non-tissue specific control. Luciferase activity under the PPE-1 promoter (FIG. 34; open bars) control was higher both in the normal (6.8±3.2) and in healing wound region (5±1.6) compared to the activity observed under the CMV control (FIG. 34; black bars).

Because both the CMV and PPE-1 promoter exhibited reduced expression levels in the healing wound, these results are difficult to interpret. Despite this unexpected observation, it is clear that the PPE-1 promoter drives higher levels of expression than the CMV promoter in both normal and healing tissue. The presence of necrotic scar tissue may account for the reduced expression levels observed with both promoters in the healing wound.

Example 22

Targeted Expression of VEGF and PDGF-B to Ischemic Muscle Vessels

In-vivo induction of angiogenesis oftentimes results in a primitive vessel network consisting of endothelial cells. These nascent vessels rupture easily, prone to regression and leakiness and poorly perfused. To overcome these limitations localized, timed and dose-controlled delivery of various angiogenic factors, capable of recruiting endothelial cells as well as periendothelial cells (i.e., pericytes in small vessels or smooth muscle cells in larger vessels) is desired.

The modified preproendothelin-1 promoter, PPE-1-3X was used to express in the endothelium of ischemic limb muscles either VEGF or PDGF-B, an endothelial secreted factor which recruits smooth muscle cells towards the origin of secretion thereby preventing hyper permeability of newly formed vessels.

To determine expression of VEGF and PDGF-B in ischemic tissues, in-situ hybridization was performed. As shown in FIGS. 43A-C, while a significant expression of VEGF mRNA could be detected in ischemic muscle sections from Ad5PPE-1-3XVEGF treated mice, essentially no signal could be seen in muscle sections of Ad5CMVVEGF or saline-treated mice. Similarly, the presence of mRNA of PDGF-B was detected in ischemic limb muscles of mice treated with Ad5PPE-1-3XPDGF-B, but not in Ad5CMVPDGF-B or saline-treated mice (FIGS. 43E-G). Interestingly, the pattern of the signal in FIGS. 1A and 1E resembled vascular structure. Notably, representative liver sections from the various treatment groups demonstrated massive expression of VEGF or PDGF-B in Ad5CMV treated animals (FIGS. 43D and 43H), while no expression was detected in the livers of Ad5PPE-1-3X vectors treated mice (data not shown).

Altogether, the assay indicates that the Ad5PPE-1-3X vectors mediate measurable expression of angiogenic factors in a target organ, while the constitutive Ad5CMV vectors expressed their transgene almost exclusively in hepatic tissues.

Example 23

Enhanced Angiogenesis by PPE-Mediated VEGF Expression

The therapeutic effect of Ad5PPE-1-3XVEGF was compared to that of previously reported Ad5CMVVEGF. $10^9$ PFUs of either therapeutic vectors, as well as reporter vector Ad5CMVluciferase and equivalent volume of saline as control were systemically administered to mice, 5 days following femoral artery ligation. Ultrasonic (US) images of the medial aspect of both limbs were taken in angiographic mode. As shown in FIGS. 27A-D, 21 days following ligation, the signal of perfusion was diminished and truncated in the control animals; however, continuous, enhanced signal was seen in the US images of both Ad5PPE-1-3XVEGF and Ad5CMVVEGF treated mice. The mean intensity of perfusion on the $21^{st}$ day in the two VEGF treatment groups was over 3 times higher than that of the control group (p<0.01), and similar to that recorded from the normal, contralateral limbs of the animals (FIG. 27E) Immunohistochemistry analysis done 21 days following femoral artery ligation and using anti CD-31, an endothelial specific marker, showed a mean of 546 CD31+ cells/mm$^2$ in the ischemic muscle sections of Ad5PPE-1-3XVEGF treated mice, comparing to 585 and 485 CD31+ cells/mm$^2$ in the Ad5CMVVEGF and control groups, respectively (FIG. 27F). This data shows that in the short term treatment with Ad5PPE-1-3XVEGF is as effective as the treatment with the potent CMV promoter of Ad5CMVVEGF. Furthermore, liver sections of the mice stained in H&E showed no indications for hepatitis or other pathological chronic changes (data not shown), thereby ruling out adenovirus tropic effect on hepatocytes.

Example 24

Prolonged Effect of VEGF Gene Therapy by PPE-Regulated Expression

Tissue specific expression versus constitutive expression of pro-angiogenic factors was addressed with respect to the induction of angiogenesis. The effects of PPE-regulated and CMV-regulated VEGF expression on perfusion and angiogenesis were tested in 70 days long experiments. Mice with ischemic limb were treated as above (see Example 23). US imaging revealed significant improvement in perfusion in both treatment groups beginning 1-2 weeks following virus administration, while minor changes were detected in the control group (data not shown). The long-term effect of the Ad5PPE-1-3XVEGF treatment was detected 50 and 60 days following femoral artery ligation. Perfusion was significantly increased in the Ad5PPE-1-3XVEGF treated mice, as compared to Ad5CMVVEGF or saline-treated mice. The difference in perfusion between Ad5CMVVEGF and control treated animals decreased over that time interval. On the $50^{th}$ day, mean intensity of perfusion in the Ad5PPE-1-3XVEGF treated group was about 50% higher than in the Ad5CMVVEGF or saline treated mice, and similar to that of the contralateral normal limb (p<0.01, FIG. 44A). Upon sacrifice of the animals on the $70^{th}$ day, the capillary density in the muscle sections of Ad5PPE-1-3XVEGF treated mice was 747 CD31+ cells/mm$^2$, which is 57% and 117% higher than in the Ad5CMVVEGF (474 CD31+ cells/mm$^2$) and control (342 CD31+ cells/mm$^2$) groups, respectively (p<0.01, FIG. 44B).

Example 25

Enhanced Angiogenesis by PPE-Promoter Endothelial-Specific PDGF-B Expression

PDGF-B is a paracrine endothelial secreted factor, which has been shown to be involved in vessel maturation by recruitment of smooth muscle cells, and probably also in angiogenesis [Edelberg, J. M. et al. *Circulation* 105, 608-13. (2002); Hsu et al. *J Cell Physiol* 165, 239-45. (1995); Koyama, N. et al. *J Cell Physiol* 158, 1-6. (1994)]. It has also been shown that PDGF-B is involved in intimal thickening [Sano, H. et al. *Circulation* 103, 2955-60. (2001); Kaiser, M., et al. *Arthritis Rheum* 41, 623-33. (1998)] and in fibroblast proliferation [Nesbit, M. et al. *Lab Invest* 81, 1263-74. (2001); Kim, W. J. et al. *Invest Ophthalmol Vis Sci* 40, 1364-72. (1999).]. The ability of PDGF-B to induce angiogenesis under endothelial specific regulation was tested in vitro and in-vivo.

Ad5PPE-1-3XPDGF-B vector induced angiogenic changes in endothelial cells in-vitro, like Ad5PPE-1-3XVEGF (data not shown). Transduction of endothelial cells cultured on fibrin coated cultureware with 10 MOI of Ad5PPE-1-3XPDGF-B resulted in the formation of 2-dimensional circular structures and fibrin degradation.

For in-vivo effect, mice were systemically treated with $10^9$ PFUs of Ad5PPE-1-3XPDGF-B, 5 days following femoral artery ligation. 30 days following ligation the mean intensity of perfusion in the Ad5PPE-1-3XPDGF-B treated mice was about 90% higher than that in the control group (FIG. 45A). 80 days following ligation the intensity of perfusion in the Ad5PPE-1-3XPDGF-B treated group was 60% higher than in the control group (FIG. 45B)

Capillary density was measured 35 and 90 days following ligation. In the short time interval, the mean capillary density in ischemic muscle sections of the Ad5PPE-1-3XPDGF-B treated mice was 516 CD31+ cells/mm$^2$, while in the saline-treated group it was 439 (FIG. 45C). 90 days following ligation the mean capillary density in Ad5PPE-1-3XPDGF-B treated mice increased slightly to 566 CD31+ cells/mm$^2$, while a moderate decrease was detected in the control group (378 CD31+ cells/mm$^2$, FIG. 45D)

The results indicate that Ad5PPE-1-3XPDGF-B vector by itself is a potent angiogenic treatment, which not only induces angiogenesis in the short term following administration, but is capable of retaining a therapeutic effect for a long period of time. No chronic changes were detected in the livers of the mice treated with Ad5PPE-1-3XPDGF-B.

Example 26

Vessel Maturation by PDGF-B Expression in Endothelial Cells

Figure 46A:
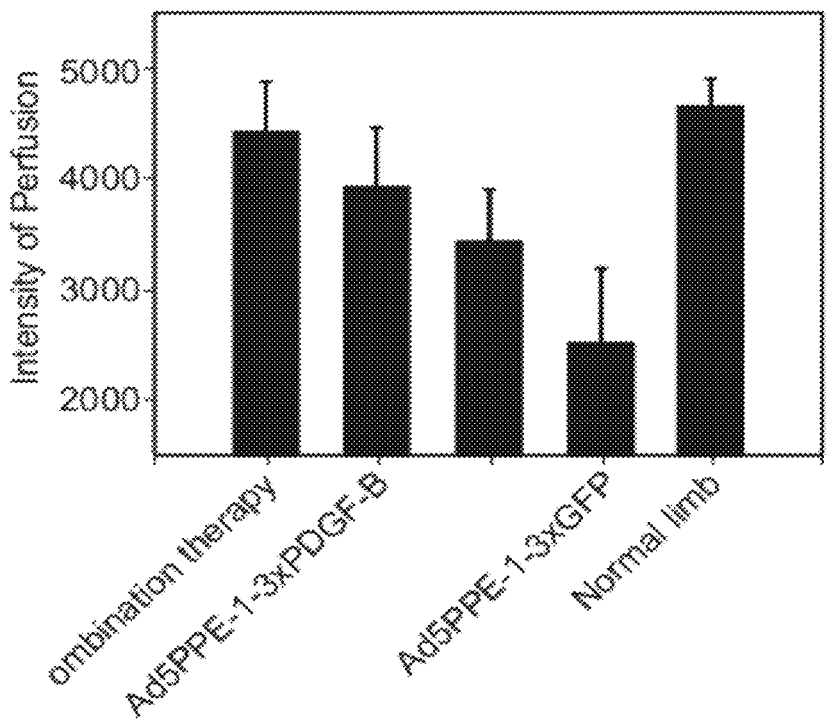
Figure 46B:
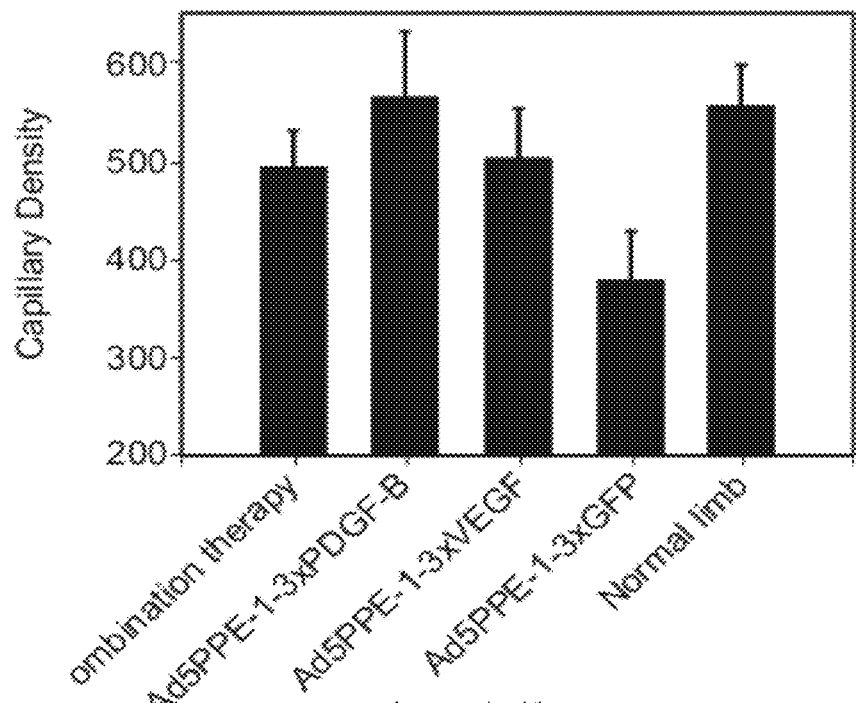
Figure 46C:
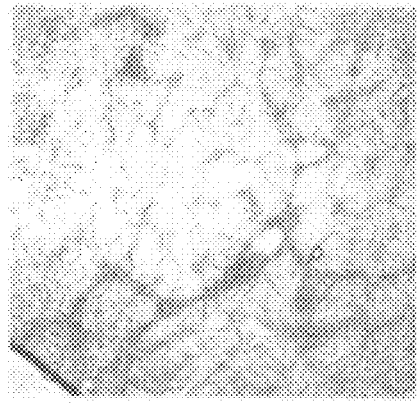
Figure 46D:
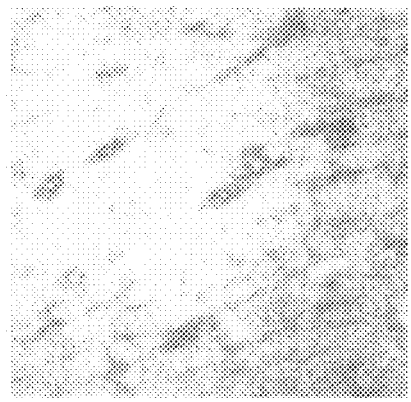
Figure 46E:
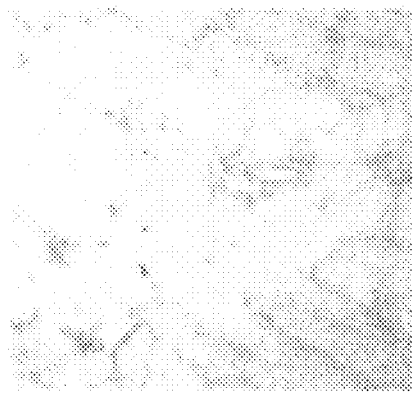
Figure 46F:
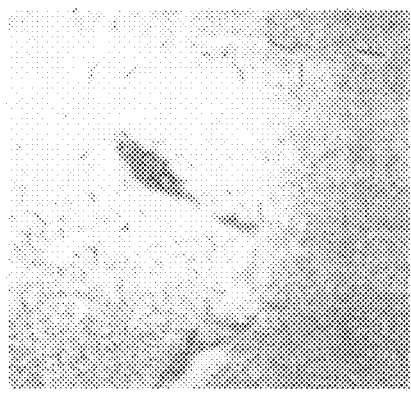
Figure 46G:
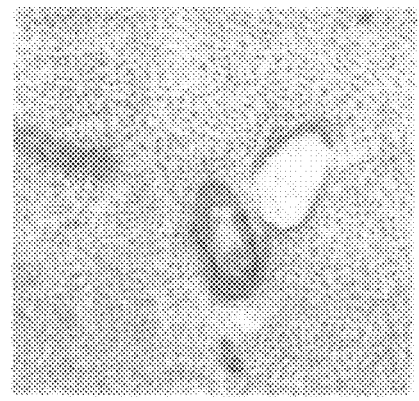

The assumption that further enhancement of angiogenesis and maturation of vasculature can be achieved by utilizing both VEGF and PDGF-B in a combination therapy was tested using two modalities of treatment: (i) single administration of $10^9$ PFUs of Ad5PPE-1-3XVEGF and of Ad5PPE-1-3XPDGF-B; (ii) administration of similar dose of Ad5PPE-1-3XPDGF-B 5 days following administration of Ad5PPE-1-3XVEGF. Both modalities yielded the same results, and therefore are referred to as one. 90 days following ligation, both the combination therapy and the Ad5PPE-1-3XVEGF treated mice exhibited significantly higher capillary density as compared to the control, Ad5PPE-1-3XGFP treated mice, but there was no significant difference among the various therapeutic groups (FIG. 46B). However, the mean intensity of perfusion in US imaging in the combination therapy group was up to 42% higher than the Ad5PPE-1-3XVEGF treated group (FIG. 46A). This can be explained by maturation of small vessels in the ischemic muscles of the combination therapy groups and Ad5PPE-1-3XPDGF-B treated mice. Significant staining for vascular smooth muscle cells was seen in muscle sections from mice treated with the combination therapy or Ad5PPE-1-3XPDGF-B, immunostained for α-SMactin (FIGS. 46C-D). Sparse staining could be seen in control and Ad5PPE-1-3XVEGF treated mice (FIGS. 46E-F). In the normal limb muscles there was prominent staining around larger arterioles and venules (FIG. 46G). Similar results were obtained as early as 35 days following ligation in mice treated with Ad5PPE-1-3XPDGF-B (data not shown). No chronic changes were apparent in liver sections of treated mice 35 days following ligation.

These results were further substantiated in a separate experiment, which addressed the effect of PDGF-B alone and in combination therapy on blood perfusion 50 days following ligation. As shown in FIG. 47, 50 days following ligation, blood perfusion intensity in the combination therapy group resembled completely that of normal limb. This effect was PPE-3X dependent, as constitutive expression (CMV promoter) of both growth factors resulted in only half perfusion capacity. Interestingly, PPE-3X dependent expression of PDGF-B alone could mediate nearly the same perfusion (i.e., 77%) as induced by the combination therapy. However, such results were not apparent using a constitutive promoter.

These results corroborate that the PPE-1-3X promoter is capable of strong enough activation of the therapeutic genes, in spite of the systemic administration, without compromising the preferential expression in angiogenic endothelial cells. Furthermore, these results substantiate PDGF-B as a pro-angiogenic factor which can mediate its angiogenic action without further addition of well established angiogenic growth factors, such as VEGF.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A method of inhibiting angiogenesis in endothelial cells of a subject in need thereof, the method comprising administering to the subject a nucleic acid construct comprising:
   (a) a promoter which comprises a cis-acting regulatory element comprising the complementary sequence of SEQ ID NO:8; and
   (b) a nucleic acid sequence encoding a cell toxin or an apoptosis inducing factor under the control of said promoter.

2. The method of claim 1, wherein the cis-acting regulatory element further comprises at least one copy of the complementary sequence of SEQ ID NO:6.

3. The method of claim 1, wherein the cis-acting regulatory element further comprises two copies of the complementary sequence of SEQ ID NO: 6.

4. The method of claim 1, wherein the cis-acting regulatory element is the complementary sequence of SEQ ID NO: 7.

5. The method of claim 1, wherein the promoter comprises an endothelial cell specific promoter.

6. The method of claim 5, wherein the endothelial cell specific promoter comprises a PPE-1 promoter.

7. The method of claim 1, wherein the promoter further comprises a hypoxia response element.

8. The method of claim 7, wherein the hypoxia response element comprises at least one copy of the sequence as set forth in SEQ ID NO: 5.

9. The method of claim 1, Wherein the promoter is a PPE-1-3X promoter.

10. The method of claim 1, wherein the cell toxin or the apoptosis inducing factor is selected from a pro-apoptotic gene product, a Herpes simplex thymidine kinase (HSV-tk), angiostatin, endostatin, or an angiostatin-endostatin chimera.

11. The method of claim 10, wherein the cell toxin is HSV-tk.

12. The method of claim 1, wherein the cell toxin is an angiogenesis regulator.

13. The method of claim 1, wherein the administering comprises administering an adenovirus vector comprising the nucleic acid construct.

14. The method of claim 13, wherein the adenovirus vector is an adenovirus serotype 5 vector.

15. The method of claim 1, wherein the subject is a human.

16. The method of claim 1, wherein the cell toxin or the apoptosis inducing factor, when expressed in the endothelial cells, reduces the size of a tumor or a metastasis thereof.

17. A method of inhibiting angiogenesis in endothelial cells of a subject in need thereof, the method comprising administering to the subject a vector comprising:
   (a) a promoter which comprises a cis-acting regulatory element comprising the complementary sequence of SEQ ID NO:8; and
   (b) a nucleic acid sequence encoding a HSV-tk polypeptide under the control of the promoter.

18. The method of claim 17, wherein the cis-acting regulatory element further comprises at least one copy of the complementary sequence of SEQ ID NO: 6.

19. The method of claim 17, wherein the cis-acting regulatory element further comprises two copies of the complementary sequence of SEQ ID NO 6.

20. The method of claim 17, wherein the cis-acting regulatory element comprises the complementary sequence of SEQ ID NO: 7.

21. The method of claim 17, wherein the promoter comprises an endothelial cell specific promoter.

22. The method of claim 21, wherein the endothelial cell specific promoter comprises a PPE-1 promoter.

23. The method of claim 17, wherein the promoter further comprises a hypoxia response element.

24. The method of claim 23, wherein the hypoxia response element comprises at least one copy of the sequence set forth in SEQ ID NO: 5.

25. The method of claim 17, wherein the promoter comprises a PPE-1-3X promoter.

26. The method of claim 17, wherein the vector is an adenovirus vector.

27. The method of claim 26, wherein the adenovirus vector is an adenovirus serotype 5 vector.

28. The method of claim 17, wherein the subject is a human.

29. The method of claim 17, wherein the HSV-tk polypeptide, when expressed in the endothelial cells, reduces the size of a tumor or a metastasis thereof.

30. A method of inhibiting angiogenesis in endothelial cells of a subject in need thereof, the method comprising administering to the subject a recombinant adenovirus vector comprising:
   (a) a promoter which comprises a cis-acting regulatory element comprising the complementary sequence of SEQ ID NO: 8 and at least one copy of the complementary sequence of SEQ ID NO: 6;
   (b) a nucleic acid sequence encoding a cell toxin under the control of the promoter; and
   (c) a hypoxia response element as set forth in SEQ ID NO: 5,
   wherein the adenovirus vector is an Ad serotype 5 vector.

31. The method of claim 30, wherein the cell toxin comprises a HSV-tk polypeptide.

32. The method of claim 30, wherein the promoter is a PPE-1-3X promoter.

33. The method of claim 30, wherein the subject is a human.

34. The method of claim 30, wherein the cell toxin, when expressed in the endothelial cells, reduces the size of a tumor or a metastasis thereof.

* * * * *